(12) United States Patent
Bennett et al.

(10) Patent No.: US 9,011,153 B2
(45) Date of Patent: Apr. 21, 2015

(54) SYSTEMS AND METHODS FOR USER-SPECIFIC MODULATION OF NUTRIENT INTAKE

(71) Applicant: Good Measures, LLC, Boston, MA (US)

(72) Inventors: George B. Bennett, Brookline, MA (US); Daniel R. Ries, Belmont, MA (US); Stefany A. Shaheen, Portsmouth, NH (US); Chesley M. Chen, Concord, MA (US); Emily P. Stone, Cambridge, MA (US); Robert V. Mathews, Somerville, MA (US)

(73) Assignee: Good Measures, LLC, Boston, MA (US)

( * ) Notice: Subject to any disclaimer, the term of this patent is extended or adjusted under 35 U.S.C. 154(b) by 0 days.

(21) Appl. No.: 13/768,997

(22) Filed: Feb. 15, 2013

(65) Prior Publication Data
US 2013/0216982 A1     Aug. 22, 2013

Related U.S. Application Data

(60) Provisional application No. 61/600,448, filed on Feb. 17, 2012.

(51) Int. Cl.
*G09B 5/00*     (2006.01)
*G06F 19/00*     (2011.01)

(52) U.S. Cl.
CPC .............. *G09B 5/00* (2013.01); *G06F 19/3475* (2013.01)

(58) Field of Classification Search
CPC .................... G06F 19/3475; G06F 30/0631

USPC ..................... 434/127, 238; 705/14.55, 14.66
See application file for complete search history.

(56) References Cited

U.S. PATENT DOCUMENTS

| | | | |
|---|---|---|---|
| 5,412,560 | A | 5/1995 | Dennison |
| 5,640,774 | A | 6/1997 | Goldman |
| 5,704,350 | A | 1/1998 | Williams, III |
| 5,730,654 | A | 3/1998 | Brown |
| 5,819,735 | A | 10/1998 | Mansfield et al. |
| 5,954,640 | A | 9/1999 | Szabo |
| 6,283,914 | B1 | 9/2001 | Mansfield et al. |
| 6,341,295 | B1 | 1/2002 | Stotler |

(Continued)

OTHER PUBLICATIONS

"Diet Optimization Methods Can Help Translate Dietary Guidelines into a Cancer Prevention Food Plan," Masset, et al., American Society for Nutrition, The Journal of Nutrition:Nutrient Requirements and Optimal Nutrition, Jun. 17, 2009, pp. 1541-1548.

(Continued)

*Primary Examiner* — Bruk Gebremichael
(74) *Attorney, Agent, or Firm* — Ropes & Gray LLP

(57) ABSTRACT

This disclosure relates generally to nutritional analysis and recommendations, including systems and methods that provide personalized approaches for analyzing nutrient intake levels and for generating recommendations that are responsive to a user's current nutritional intake and the user's nutrition-related goals. The systems and methods also provide personalized analysis and recommendation for other areas or activities, including applications to exercise adherence, sleep adherence, mediation adherence, and general wellness assessment. Each of these areas or activities can be assessed alone or in combination with one or more other areas or activities.

30 Claims, 59 Drawing Sheets

(56) References Cited

U.S. PATENT DOCUMENTS

| | | | |
|---|---|---|---|
| 6,356,940 | B1 | 3/2002 | Short |
| 6,370,513 | B1 | 4/2002 | Kolawa et al. |
| 6,553,386 | B1 | 4/2003 | Alabaster |
| 6,556,963 | B1 | 4/2003 | Tetzlaff |
| 6,585,516 | B1 | 7/2003 | Alabaster |
| 6,652,455 | B1 | 11/2003 | Kocher |
| 6,817,863 | B2 | 11/2004 | Bisogno |
| 6,872,077 | B2 | 3/2005 | Yeager |
| 6,953,342 | B2 | 10/2005 | Bisogno |
| 7,090,638 | B2 | 8/2006 | Vidgen |
| 7,110,994 | B1 | 9/2006 | Herdman |
| 7,297,109 | B2 | 11/2007 | Brown |
| 7,413,438 | B2 | 8/2008 | Bisogno |
| 7,558,788 | B1 | 7/2009 | Herdman |
| 7,680,690 | B1 | 3/2010 | Catalano |
| 7,778,843 | B2 | 8/2010 | Ishikawa et al. |
| 7,788,113 | B2 | 8/2010 | Fuhrman et al. |
| 7,853,626 | B2 | 12/2010 | Jung et al. |
| 7,882,150 | B2 | 2/2011 | Badyal |
| 7,957,985 | B2 | 6/2011 | Kashani et al. |
| 7,959,567 | B2 | 6/2011 | Stivoric et al. |
| 7,974,856 | B2 | 7/2011 | Jung et al. |
| 7,974,881 | B2 | 7/2011 | Culver et al. |
| 8,021,681 | B2 | 9/2011 | Cincotta |
| 8,036,912 | B2 | 10/2011 | Jensen et al. |
| 8,053,007 | B2 | 11/2011 | Innocenzi |
| 2002/0099274 | A1* | 7/2002 | Isomura et al. ............... 600/300 |
| 2003/0208409 | A1* | 11/2003 | Mault ............................. 705/26 |
| 2005/0075934 | A1* | 4/2005 | Knight et al. .................. 705/15 |
| 2006/0122468 | A1* | 6/2006 | Tavor ............................ 600/300 |
| 2007/0179359 | A1* | 8/2007 | Goodwin ...................... 600/300 |
| 2007/0191689 | A1* | 8/2007 | Elitok ........................... 600/300 |
| 2007/0218107 | A1* | 9/2007 | Schnur et al. ................. 424/439 |
| 2009/0055199 | A1* | 2/2009 | Yusuf ................................ 705/1 |
| 2009/0075242 | A1* | 3/2009 | Schwarzberg et al. ....... 434/127 |
| 2009/0144081 | A1* | 6/2009 | Harlan ............................. 705/2 |
| 2009/0148818 | A1* | 6/2009 | Li et al. ......................... 434/127 |
| 2009/0275002 | A1 | 11/2009 | Hoggle |
| 2010/0080875 | A1* | 4/2010 | Miller-Kovach et al. ..... 426/232 |
| 2010/0293006 | A1* | 11/2010 | Ishikawa et al. .................. 705/2 |

OTHER PUBLICATIONS

"Meal Planning Software—Meal Planning—Recipe Analysis," http://www.ncconcepts.com/index.html, retrieved on Feb. 15, 2013.

"Application of Fuzzy Systems Theory to Setting Nutrient Requirements," Wirsam, Bernd: Washington Apr. 1996, Internet Edition Linden Jun. 1996.

"Computer-planned Menus for Patients with Diabest Mellitus," Wheeler et al, Diabetes Care, 3:6, Nov.-Dec. 1980, pp. 663-667.

"Context-Aware Personal Diet Suggestion System," Huang et al., 8th International Conference on Smart Homes and Health Telematics, ICOST Jun. 22-24, 2010, pp. 76-84.

"Diet planning for humans using mixed-integer linear programming," Sklan et al., British Journal of Nutrition, vol. 70, pp. 27-35, Jul. 1993.

"Diet Problem and Nutrient Requirement using Fuzzy Linear Programming Approach," Mamat, et al., Asian Journal of Applied Sciences, 5(1):52-59, 2012.

"Fuzzy sets and fuzzy decision making in nutrition," Wirsam et al., European Journal of Clinical Nutrition (1997) 51, 286-296.

"Health and Wellness Analysis and Programs—Inside Tracker," http://www.insidetracker.com/, retrieved on Feb. 15, 2013.

intelli-Diet is a best iPhone diet app, weight loss app, and calorie counter app! Now available for iPhone, iPod & iPad! Http://intelli-diet.com, retrieved on Feb. 15, 2013.

"Linear Programming Analysis of Constraints Upon Human Diets," Henson, Spencer, Journal of Agricultural Economics, vol. 42, Issue 3, pp. 380-393, Sep. 1991.

"Linear programming and pediatric dietetics," Colavita, et al., British Journal of Nutrition (1990) 64, pp. 307-317.

"Linear Programming Dietary Optimization (Maximum Calories and Minimal Cost)," http://www.ozgrid.com/Services/linear-dietary.htm; retrieved on Feb. 15, 2013.

"Linear Programming Module of NutriSurvey", www.nutrisurvey.de/Ip;Ip.htm, retrieved on Feb. 15, 2013.

"Linear Programming Techniques for the Construction of Palatable Human Diets," Fletcher et al, J. Opl Res. Soc. vol. 45, No. 5, May 1994, pp. 489-496.

"The Better Way to Plan Meals and Save Money," http://www.foodonthetable.com, retrieved on Feb. 15, 2013.

"Modifying diets to satisfy nutritional requirements using linear programming," Soden et al., British Journal of Nutrition (1992), 68, 565-572.

"Nutrient menu planning for clinical research centers," Wheeler et al, Journal of the American Dietetic Association, 67:4, Oct. 1975, pp. 346-350.

"Nutrition Surveys and Calculations", www.nutrisurvey.de, retrieved on Feb. 15, 2013.

"Nutritionist: Your health is in your hands", https://www.facebook.com/NutritionistApp, retrieved on Feb. 15, 2013.

"Vitabot: Online Meal Planning," http://www.vitabot.com/web/, retrieved on Feb. 15, 2013.

Nutritional Requirements to Prevent Chronic Diseases using Linear Programming and Fuzzy Multi-objective Linear Programming, Noor, et al., ICCIT 2012, pp. 565-570.

"Diabetes-Specific Nutrition Algorithm: A Transcultural Program to Optimize Diabetes and Prediabetes Care," Mechanick, Jeffrey, et al, Curr Diab Rep 12:180-194, published online Feb. 10, 2012.

"International Diabetes Center Treatment of Type 2 Diabetes Glucose Altorithm," Simonson, Gregg et al, Future Medicine, Diabetes Manage. (2011) 1(2), 175-189.

"Prevention and management of type 2 diabetes:dietary components and nutritional strategies," Ley, Sylvia, et al, www.thelancet.com, vol. 383, Jun. 7, 2014, pp. 1999-2007.

* cited by examiner

| 132 | | | | |
|---|---|---|---|---|
| FOOD CONSUMED | SERVINGS | MEAL | DATE | BARCODE ID |
| 1578 | 1 | DINNER | 10-11-10 | 12482 |
| 352 | 2 | DINNER | 10-11-10 | 54687 |
| 6548 | 1.5 | SNACK | 10-11-10 | 84654 |

FIG. 2A

| 134 | |
|---|---|
| MEAL | FOOD CONSUMED |
| 10-11-10-DINNER | {1578, 352} |
| 10-11-10-SNACK | {6548} |

136, 138

FIG. 2B good measures
beta
my account | my profile | friends | help | contact us | logout good measures index
71 my profile   my foods | nutrient goals | personal info | friends

My Name

Thank you for sharing your wellness goals (*please check all that apply*):

- ☐ Feel better
- ☐ Maintain weight
- ☐ Lose weight
- ☐ Gain weight
- ☐ Manage my stress level
- ☐ Feel more energetic
- ☐ Sleep better

- ☐ Increase my physical strength
- ☐ Improve my flexibility
- ☐ Try new fitness activities
- ☐ Exercise more frequently
- ☐ Enhance my appearance
- ☐ Learn a new exercise routine
- ☐ Train for an Upcoming athletic event

- ☐ Manage medical conditions
- ☐ Meet my Nutrient needs
- ☐ Try new foods
- ☐ Eat more fruits and vegetables
- ☐ Manage dietary restrictions

*use this space to add more goals*

* Date of Birth [Apr ▼] [1 ▼] [1970 ▼]     * = required

* Gender [Female ▼]

* Height feet: [5]   Inches: [4]

* Current Weight (lbs) [130]    * Desired Weight (lbs) [130]

* Activity Level [Lightly Active ▼]   What is my Activity level?

[update profile ⊙]   [cancel]

FIG. 15 my profile | my foods | nutrient goals | personal info | friends nutrient goals

Your nutrient goals inform your needs profile and are based on your personal info

|  |  | Daily Goal |
|---|---|---|
| Macronutrients | | |
| Calories | | 1200 cal |
| Protein | 15% of cals | 45 g |
| Carbohydrates | 55% of cals | 165 g |
| Total Fat | 30% of cals | 40 g |
| Saturated Fat | less than 7% of cals | less than 9 g |
| Fiber | | 16 g |
| Cholesterol | | less than 300 mg |
| Omega-3 | | 1100 mg |
| Vitamins | | |
| Vitamin A | | 700 mcg RAE |
| Vitamin B1 (Thiamin) | | 1.1 mg |
| Vitamin B2 (Riboflavin) | | 1.1 mg |
| Vitamin B3 (Niacin) | | 14 mg |
| Pantothenic Acid | | 5 mg |
| Vitamin B6 | | 1.5 mg |
| Folate | | 400 mcg |
| Vitamin B12 | | 2.4 mcg |
| Vitamin C | | 75 mg |
| Vitamin D | | 800 IU |
| Vitamin E | | 15 mg |
| Vitamin K | | 90 mcg |
| Minerals | | |
| Calcium | | 1200 mg |
| Copper | | 900 mcg |
| Iron | | 8 mg |
| Magnesium | | 320 mg |
| Manganese | | 1.8 mg |
| Phosphorus | | 700 mg |
| Potassium | | 4700 mg |
| Selenium | | 55 mcg |
| Sodium | | less than 2300 mg |
| Zinc | | 8 mg |

FIG. 16

Create Combination
Food combinations allow you to group foods you normally eat together.

Combination Name:
chicken and broccoli

| Ingredients | Find Food | | FIND |
| --- | --- | --- | --- |
| Food | Qty | Unit | Calories |
| Chicken Leg | 1 | cup, chopped 01 ▼ | 325 🗑 |
| Broccoli | 1 | stalk, large (11"- ▼ | 98 🗑 |
| | | Total : | 423 |

Can these foods be recommended separately?
⊙ Yes
○ No

CANCEL    SAVE

FIG. 19 good measures
beta my account | my profile | friends | help | contact us | logout good measures index
67

[ log >> ] [ live >> ] [ learn >> ]

Week of January 29, 2012

| Sun 01/29 | Mon 01/30 | Tue 01/31 | Wed 02/01 | Thu 02/02 | Fri 02/03 | Sat 02/04 |

Fri, Feb 3, 2012

Breakfast | Find Food | FIND

| ▼ | Food | | Qty | Unit | Calories |
|---|------|---|-----|------|----------|
| ☐ | Bananas | ℓ | 1 | medium ▼ | 105 |
| ☐ | Bran Flakes | ℓ | 2 | cup ▼ | 256 |
| ☐ | Skim Milk | ℓ | 1 | cup ▼ | 83 |
| | | | | Total: | 444 |

Lunch | Find Food | FIND

Dinner | Find Food | FIND

Snacks | Find Food | FIND

Exercise | Find Exercise | FIND or ADD CALORIES FROM EXERCISE

| Calories | |
|---|---|
| Calorie Goal | 1200 |
| Today's Exercise + | 0 |
| Needs = | 1200 |
| Today's Food − | 444 |
| Under = | 756 |

Macronutrient Summary

| | | % Daily Calories | |
|---|---|---|---|
| | Today | Goal | Actual |
| Carbs | 103 g | 55% | 82% |
| Fat | 2 g | 30% | 4% |
| Protein | 17 g | 15% | 14% | terms & conditions
privacy policy
contact us
about good measures
good measures home
my profile
my account log live
your menu only better
new foods to try learn
needs profile
nutrients on target

FIG. 23

| log ≫ | live ≫ | learn ≫ |

← Week of January 29, 2012

| Sun 01/29 | Mon 01/30 | Tue 01/31 | Wed 02/01 | Thu 02/02 | Fri 02/03 | Sat 02/04 |

Fri, Feb 3, 2012

Breakfast | Find Food | FIND

| ↓ | Food | | Qty | Unit | Calories |
|---|---|---|---|---|---|
| ☐ | Bananas | 🔖 | 1 | medium ▼ | 105 |
| ☐ | Bran Flakes | 🔖 | 2 | cup ▼ | 256 |
| ☐ | Skim Milk | 🔖 | 1 | cup ▼ | 83 |
| | | | | | Total: 444 |

Lunch | Find Food | FIND

| ↓ | Food | | Qty | Unit | Calories |
|---|---|---|---|---|---|
| ☐ | Sandwich, hot chicken | 🔖 | 1.0 | 1 sandwic ▼ | 443 |
| | | | | | Total: 443 |

Dinner | Find Food | FIND

Snacks | Find Food | FIND

Exercise | Find Exercise | FIND or ADD CALORIES FROM EXERCISE

| Calories | | |
|---|---|---|
| Calorie Goal | | 1200 |
| Today's Exercise | + | 0 |
| Needs | = | 1200 |
| Today's Food | − | 887 |
| Under | = | 313 |

| Macronutrient Summary | | | |
|---|---|---|---|
| | | % Daily Calories | |
| | Today | Goal | Actual |
| Carbs | 135 g | 55% | 58% |
| Fat | 19 g | 30% | 18% |
| Protein | 56 g | 15% | 24% |

FIG. 26

| log »  | live » | learn » |

Week of January 29, 2012

| Sun 01/29 | Mon 01/30 | Tue 01/31 | Wed 02/01 | Thu 02/02 | Fri 02/03 | Sat 02/04 |

Fri, Feb 3, 2012

Breakfast | Find Food | FIND

| ▼ | Food | Qty | Unit | Calories |
|---|---|---|---|---|
| Combine | nas | 1 | medium ▼ | 105 |
| Delete | Flakes | 2 | cup ▼ | 256 |
| ✓ | Skim Milk | 1 | cup ▼ | 83 |

Total: 444

Lunch | Find Food | FIND

| ▼ | Food | Qty | Unit | Calories |
|---|---|---|---|---|
| ☐ | Sandwich, hot chicken | 1.0 | 1 sandwic ▼ | 443 |

Total: 443

Dinner | Find Food | FIND

Snacks | Find Food | FIND

Exercise | Find Exercise | FIND or ADD CALORIES FROM EXERCISE

| Calories | | |
|---|---|---|
| Calorie Goal | | 1200 |
| Today's Exercise | + | 0 |
| Needs | = | 1200 |
| Today's Food | - | 887 |
| Under | = | 313 |

| Macronutrient Summary | | % Daily Calories | |
|---|---|---|---|
| | Today | Goal | Actual |
| Carbs | 135 g | 55% | 58% |
| Fat | 19 g | 30% | 18% |
| Protein | 56 g | 15% | 24% |

FIG. 27

| log >> | live >> | learn >> |

Week of January 29, 2012

| Sun 01/29 | Mon 01/30 | Tue 01/31 | Wed 02/01 | Thu 02/02 | Fri 02/03 | Sat 02/04 |

Fri, Feb 3, 2012

| Breakfast | Find Food | | | FIND |

| | Food | Qty | Unit | Calories |
|---|---|---|---|---|
| ☐ | Bran Flakes, milk and banana | 1.0 | Serving ▼ | 444 |
| | | | Total: | 444 |

| Lunch | Find Food | | | FIND |

| | Food | Qty | Unit | Calories |
|---|---|---|---|---|
| ☐ | Sandwich, hot chicken | 1.0 | 1 sandwich ▼ | 443 |
| | | | Total: | 443 |

| Dinner | Find Food | FIND |
| Snacks | Find Food | FIND |
| Exercise | Find Exercise | FIND or ADD CALORIES FROM EXERCISE |

Calories

| Calorie Goal | | 1200 |
|---|---|---|
| Today's Exercise | + | 0 |
| Needs | = | 1200 |
| Today's Food | − | 887 |
| Under | = | 313 |

Macronutrient Summary

| | | % Daily Calories | |
|---|---|---|---|
| | Today | Goal | Actual |
| Carbs | 135 g | 55% | 58% |
| Fat | 19 g | 30% | 18% |
| Protein | 56 g | 15% | 24% |

FIG. 29

Week of January 29, 2012

| Sun 01/29 | Mon 01/30 | Tue 01/31 | Wed 02/01 | Thu 02/02 | Fri 02/03 | Sat 02/04 |

Fri, Feb 3, 2012

Find Exercise swim  [FIND EXERCISE] or [ADD CALORIES FROM EXERCISE]

- Swimming laps, freestyle, fast, vigorous effort
- Swimming laps, freestyle, light/moderate effort
- Swimming, backstroke, general
- Swimming, breaststroke, general
- Swimming, butterfly, general
- Swimming, leisurely, general
- Swimming, sidestroke, general
- Swimming, synchronized
- Swimming, treading water, fast/vigorous
- Swimming, treading water, moderate effort

| Under | = | 313 | Protein | 56 g | 15% | 24% |

Fri, Feb 3, 2012

| Breakfast | Find Food | | | FIND |
|---|---|---|---|---|
| ⬇ Food | | Qty | Unit | Calories |
| ☐ ⁂Bran Flakes, milk, and banana 🖉 | | 1 | Serving ▼ | 444 |
| | | | | Total: 444 |

| Lunch | Find Food | | | FIND |
|---|---|---|---|---|
| ⬇ Food | | Qty | Unit | Calories |
| ☐ Sandwich, hot chicken 🖉 | | 1 | 1 sandwic ▼ | 443 |
| | | | | Total: 443 |

| Dinner | Find Food | FIND |
|---|---|---|
| Snacks | Find Food | FIND |

| Exercise | Find Exercise | FIND | or | ADD CALORIES FROM EXERCISE |
|---|---|---|---|---|
| ⬇ Exercise | | Duration | Unit | Calories |
| ☐ Swimming laps, freestyle, light/moderate effort | | 60 | Min | 472 |
| ☐ Calories Entered Directly | | | | 200 |

| Calories | | |
|---|---|---|
| Calorie Goal | | 1200 |
| Today's Exercise | + | 672 |
| Needs | = | 1872 |
| Today's Food | − | 887 |
| Under | = | 985 |

| Macronutrient Summary | | | |
|---|---|---|---|
| | | % Daily Calories | |
| | Today | Goal | Actual |
| Carbs | 135 g | 55% | 58% |
| Fat | 19 g | 30% | 18% |
| Protein | 56 g | 15% | 24% |

FIG. 33 good measures
beta my account | my profile | friends | help | contact us | logout good measures index
67

[ log >> ] [ live >> ] [ learn >> ]

your menu only better

Your Menu Only Better highlights the foods that best meet your personal needs. This report will be ready once you have logged enough food for the Good Measures Contextual Nutrition Analytic Engine to make a calculation. Please continue to log your meals and check back frequently to see how you can improve your index with the foods you already eat.

new foods to try

Semolina
Semolina, unenriched
Nutrition information for one cup

Calories 601

| | | | |
|---|---|---|---|
| Protein | 21 g | Carbohydrates | 122 g |
| Fat | 2 g | Fiber | 7 g |
| Saturated Fat | 0 g | Sugars | – |
| Trans Fat | – | Vitamin A | 0 mcg RAE |
| Cholesterol | 0 mg | Vitamin C | 0 mg |
| Sodium | 2 mg | Calcium | 28 mg |

[ SEE MORE FOODS TO TRY ]

Good Measures provides information that can help you make nutritional choices, but you are responsible for the food you eat and exercise you undertake. Always ask a health care provider if you have questions about your food, exercise, or unique needs. Good Measures is not a health care provider, and our nutritional information is no substitute for dietary or medical advice. To view Terms and Conditions, click here.

terms & conditions   home            log    live                      learn
privacy policy       my profile              your menu only better    needs profile
contact us           my account              new foods to try         nutrients on target
about good measures
good measures

FIG. 34

| | DAILY | WEEKLY | For 01/28/2012 to | 02/03/2012 ▼ |

TARGET

54

Food Sources of Magnesium from your 01/28 - 02/03 meals
Target: at Least 310 mg
Actual: 55 mg

*Looking for more Magnesium?*

TRY THIS

| Date | Meal | Food | | Qty | Unit | Contribution |
|------|------|------|---|-----|------|--------------|
| 02/03/2012 | Breakfast | Milk, nonfat, fluid, with added vitamin A and vitamin D (fat fr | 🛈 | 1 | cup | 27 mg |
| 02/03/2012 | Breakfast | Cereals ready-to-eat, KELLOGG'S, SPECIAL K Vanilla Alm | 🛈 | 1 | cup | 20 mg |
| 02/03/2012 | Lunch | Rolls, dinner, plain, commercially prepared (includes brow | 🛈 | 1 | roll | 7 mg |

Good Measures provides information that can help you make nutritional choices, but you are responsible for the food you eat and exercise you undertake. Always ask a health care provider if you have questions about your food, exercise, or unique needs. Good Measures is not a health care provider, and our nutritional information is no substitute for dietary or medical advice. To view Terms and Conditions, Click here.

FIG. 36C nutrients on target
You have met your goals for the following nutrients:

Macronutrients
        Saturated Fat ✓
        Cholesterol ✓

Vitamins
        Vitamin B2 ✓
        Vitamin B3 ✓
        Vitamin B12 ✓

Minerals
        Iron ✓
        Manganese ✓
        Phosphorus ✓
        Selenium ✓
        Sodium ✓

Good Measures provides information that can help you make nutritional choices, but you are responsible for the food you eat and exercise you undertake. Always ask a health care provider if you have questions about your food, exercise, or unique needs. Good Measures is not a health care provider, and our nutritional information is no substitute for dietary or medical advice. To view Terms and Conditions, Click here.

| terms & conditions | home | log | live | learn |
|---|---|---|---|---|
| privacy policy | my profile | | your menu only better | needs profile |
| contact us | my account | | new foods to try | nutrients on target |
| about good measures | | | | |

 good measures

FIG. 37

SYSTEMS AND METHODS FOR USER-SPECIFIC MODULATION OF NUTRIENT INTAKE

CROSS REFERENCE TO RELATED APPLICATIONS

This application claims the benefit of U.S. Provisional Application No. 61/600,448, filed on Feb. 17, 2012, which is hereby incorporated herein by reference in its entirety. This application is related to co-pending PCT Application No. PCT/US2013/026468 filed Feb. 15, 2013, which is hereby incorporated herein by reference in its entirety.

TECHNICAL FIELD

This disclosure relates generally to nutritional analysis and recommendations including, without limitation, systems and methods that provide personalized approaches for analyzing nutrient intake levels and for generating recommendations that are responsive to a user's current nutritional intake and the user's nutrition-related goals. The systems and methods also provide personalized analysis and recommendations for other areas or activities, including application to exercise adherence, sleep adherence, mediation adherence, and general wellness assessment. Each of these areas or activities can be assessed alone or in combination with one or more other areas or activities.

BACKGROUND

Individuals often find it frustrating to improve their overall nutrition and health. Currently available strategies often result in limited or no success, in part because they rely on inadequate information about the person and his or her objectives. One common approach is to consult with physicians who provide general guidelines and advice, such as instructions to consume less salt and more fruits and vegetables, exercise more, or avoid certain foods such as red meats. However, given the complexities and individual variations in human metabolism, it can be very difficult for physicians to provide guidelines that are effective, and very difficult for people to implement the guidelines.

Multiple nutritional computer programs exist that provide guidelines by analyzing a person's consumption. These programs typically identify nutrients that are deemed to be deficient for the person, then recommend foods high in the identified nutrients. For example, if a person is found to be deficient in potassium, a program may suggest that the person consume a banana because of the high potassium level of bananas. However, suggesting a food because of its high level of one nutrient does not necessarily lead to an improvement in a person's overall nutrition. For example, the person may have already consumed an excessive amount of other nutrients, such as carbohydrates, so suggesting that the person eat a banana may increase the person's potassium level at the expense of the person's carbohydrate level, in some cases to the person's detriment. When multiple nutrients are at issue, it can be particularly difficult to make recommendations that address deficiencies and excesses in some nutrients without harmfully changing the levels of nutrients that are already in balance. This problem is particularly challenging for meal-planning and diet and exercise routine development, where a typical diet may include hundreds of foods with a multitude of different variations between ingredients and portion sizes.

Some researchers have proposed the use of a single dietary program for a particular population group that is sensitive to food costs and existing consumption patterns within that group (see, e.g., Masset et. al, 2009). The goal of these programs is to change the average existing consumption pattern of the group as little as possible while staying within a safe range of nutrients. But this "one-size fits all" approach does not help individuals set meaningful goals for diet and exercise or track progress toward these goals, let alone help the individual improve their own personal nutritional or exercise profile.

SUMMARY

Accordingly, systems and methods are disclosed herein for providing personalized nutritional analysis and recommendations that are responsive to a user's current nutritional intake and the user's nutrition-related goals. The systems and methods can be adapted to provide tailored analysis and recommendation in other areas including for exercise adherence, sleep adherence, mediation adherence and a general wellness assessment, among others. Generally, the systems and methods determine a deviation between a target (such a desired level of a nutrient) and an attained amount (such as a consumed amount of the nutrient) and provide an indication of an alignment between a goal (as may be defined by one or more targets) and an attainment (as may be defined by consumed amounts of one or more nutrients) based on the deviation. Deviation as used herein may refer to a comparison between a specific target (which may or may not include a range) to a specific amount or level. A deviation can be determined for a specific component of the goal (e.g., a single nutrient) or for multiple components (e.g., multiple nutrients compared on a nutrient-by-nutrient basis). Other suitable mechanisms, algorithms, or devices may be used for determining the deviation. Example suitable ways to determine a deviation may include subtracting one value from another value to obtain a difference, computing a ratio between two values, statistical approaches such as a standard deviation or statistical variance, pattern comparison and recognition, correlation approaches such as by comparing a curve or graph of one set of values to a corresponding curve or graph or another set of values, comparisons based on derived properties of the data sets, such as by regression-based or line-fitting approaches, error estimation methods such as root-mean-squared. When multiple values of targets or attained levels are used, the data set may correspond to various nutrients, time periods, individuals, groups of people, or any other suitable parameter. An alignment can be determined based on one or more deviations to provide an indication of compliance between the goal and an overall attainment as both relate to the activity being assessed.

One aspect relates to a method for assessing a person's diet, the method performed by a computer system including a communications port and at least one computer processor in communication with at least one non-transitory computer readable medium storing at least one electronic database. As discussed in detail below, the computer system may be a single computer or may include multiple computers communicating over any network, such as in a distributed architecture. The at least one processor may be housed in one, some, or all of the computers in the computer system, and may be in communication with at least one an electronic database stored on the same computer or on a different computer within the computer system. The computer system may include a cloud-based set of computing systems operated by the same, related, or unrelated entities. The computer system receives data representative of an amount of a first nutrient consumed by the person during a first predetermined time period. A target level of the first nutrient is received from at least one electronic database. The computer system assigns a first numeric weight to the first nutrient based on a comparison between the amount of the first nutrient and the target level of the first nutrient, and an assessment of the person's diet based on the first numeric weight is provided via the communications port. Similar methods are anticipated for personalizing a person's exercise routine, either alone or in combination with his or her nutritional progress. Similar techniques can also be applied with respect to a group of people, for example, a family, in group meal and exercise planning. The assessment can then be communicated to the person for reasons or purposes of recommending a future food, for group meal planning, for use in developing a diet or exercise program, for an assessment of adherence to a sleep regimen, for an assessment of adherence to a medication regimen, for general wellness assessment, and other desired applications either individually or in combination.

In some implementations, a user-selected dietary program selected from a plurality of dietary programs is received, and the target level is determined based on the user-selected dietary program. The user-selected dietary program can include at least one each of a weight goal and a nutrition goal for the person. Assigning the first numeric weight can include selecting from a plurality of nutrient-specific weights for the first nutrient determined based on the weight goal or the nutritional goal.

In some implementations, a target level of a second nutrient and an amount of the second nutrient consumed by the person are received. A second numeric weight is assigned to the second nutrient based on a comparison between the consumed amount of the second nutrient and the target level of the second nutrient. The assessment of the person's diet is provided based on the first and second numeric weights. Providing an assessment of the person's diet can include providing a first indicator of an alignment between the target level of the first nutrient and the consumed amount of the first nutrient, and providing a second indicator of an alignment between the target level of the second nutrient and the consumed amount of the second nutrient. Providing an assessment of the person's diet includes providing a nutritional index representative of an aggregate alignment between the user-selected dietary program and person's diet based on the respective alignments of the first and second nutrients. The first and second indicators are graphical indicators, each graphical indicator indicating whether the person's consumption of the respective nutrient is in deficit or in excess of the respective target level.

In some implementations, a recommendation is provided for the person to consume a recommended food selected from one or more foods based on a predicted change in the nutritional index. The recommended food is selected to change the first indicator and to simultaneously reduce a negative impact on the alignment of the second nutrient. This is a result of an intelligent use of knowledge regarding nutrient distribution in the various foods known to the systems and methods described herein, and recognition by these implementations of the importance (and challenge) of simultaneity when multiple nutrients are at issue. In particular, a major pitfall of known nutritional recommendation systems is that the systems tend to define the problem to be solved as one of recommending foods to correct exclusively deficiencies in one or more nutrients without also curbing at the same time excesses in nutrients that may be harmful when consumed in excess, and without taking into account nutrients that are already in balance. At best, this approach results in separate recommendations for each problem (i.e., one set of foods for deficiencies, and another set of foods for excesses) that may collectively throw out of balance other nutrients that are already in balance. By simultaneously selecting a recommended food to improve the deviation for one nutrient while simultaneously reducing a negative impact on a second nutrient, these implementations avoid this pitfall. Several examples for accomplishing this result are discussed below, including, for example, computing a weighted function over all target nutrients alone or in combination applying a weight selection mechanism that allows even nutrients without deviations to impact the calculation.

In some implementations, the assessment is based on respective consumed amounts and target levels of three or more nutrients, including first and second nutrients. Providing the nutritional index includes calculating, for each of the three or more nutrients, a deviation for the respective nutrient by comparing the consumed amount of that nutrient to the target level for that nutrient. The recommended food is selected to simultaneously reduce the deviation for each of at least two of the three or more nutrients.

In some implementations, the recommended food is selected from one or more foods previously consumed by the person. Providing the recommendation includes providing a recommended amount of a recommended food and a recommended calendar date for the person to consume the recommended food, the recommended amount preferably being different from a previously consumed amount of the recommended food.

In some implementations, the recommended food is selected from one or more foods not previously consumed by the person. The method includes selecting a recommended food from the one or more foods not previously consumed by the person in response to determining that one or more foods previously consumed by the person does not substantially improve the nutritional index.

In some implementations, the method includes receiving data representative of a medical condition of the person and modifying the target level of the first nutrient or the first numeric weight based on one or more dietary restrictions associated with the medical condition. The one or more dietary restrictions includes a desired distribution of a plurality of nutrients during the first predefined time period. The desired distribution corresponds to two or more nutrients selected from the group consisting of calories, carbohydrates, proteins, fat, and fiber.

In some implementations, the method includes generating the target level of the first nutrient based on an actual or estimated amount of exercise performed (at least hypothetically) by the person during the first predetermined time period.

Another aspect relates to a non-transitory computer readable medium storing computer-executable instructions that, when executed by at least one computer processor, causes a computer system to perform a method for assessing a person's diet. The method includes receiving a first data input representative of a selected dietary program for the person and a second data input representative of one or more foods consumed by the person including one or more calendar dates on which each food was consumed, wherein the selected dietary program is selected from a plurality of dietary programs stored in an electronic database in communication with the at least one processor. The method includes determining based on the one or more foods and the calendar dates a consumed amount of a first nutrient for a first time period and determining based on the one or more foods and the calendar dates a consumed amount of a second nutrient for a second time period. User data profile data is received, the user data profile data representative of target amounts for the first nutrient and the second nutrient, the target amounts determined based on the selected dietary program, a nutritional goal specific to the person, and health information associated with the person. The consumed amount of the first nutrient is compared to the target amount for the first nutrient to obtain a first result, and the consumed amount of the second nutrient is compared to the target amount for the second nutrient to obtain a second result. The method includes outputting an indicator of an alignment between the person's diet and the selected dietary program based on a weighted function of the first and second results.

In some implementations, the first time period is different from the second time period.

In some implementations, generating the indicator includes selecting a weight for each of the first and second nutrients based on a comparison between the amount of the respective nutrient and the target amount of the respective nutrient.

In some implementations, the indicator includes an aggregate nutritional score that provides, based on the weighted function, a quantitative measure of the alignment between the person's diet and the selected dietary program over a third time period having a duration equal to or greater than each of the first and the second time period.

In some implementations, a recommendation is provided for the person to consume a recommended food based on a predicted change in the alignment. Providing the recommendation includes selecting the recommended food from the one or more foods previously consumed by the person, providing a recommended amount of the recommended food, and providing a recommended date for the user to consume the recommended food. An additional recommendation is provided for the person to consume an additional recommended food that is selected from a plurality of foods not previously consumed by the person.

Another aspect relates to a computer system for aligning a person's diet with specific dietary goals. The system includes a processing system including one or more processors, one or more electronic databases, and one or more communications ports. The processing system is configured to receive data representative of one or more meals that may be or has been consumed by the person, with the information for each meal indicating a specified portion of one or more foods and nutrient levels included within each specified portion. The system is also configured to determine a target nutritional profile associated with the person, the target nutritional profile including target levels for first and second nutrients. The processing system is configured to generate a meal recommendation based on a meal selected from the one or more meals, the meal recommendation including a modified portion size for at least one of the one or more foods, such that the meal recommendation simultaneously improves an alignment between nutrient levels of the first and second nutrients in the selected meal and the target nutritional profile, and output via at least one of the one or more communications ports data representative of the meal recommendation. The alignment can be done, for example, by comparing respective nutrient levels in a consumed food or meal to respective target nutrient levels in the target nutritional profile, to define a deviation for each of the nutrients, selecting one or more foods or meals from the database that will lower those deviations (or otherwise adjust them in a desired fashion), and identifying that food or meal to the person (or optionally identifying the impact on the person's index or other predetermined measure of health or wellness).

In some implementations, the processing system is configured to receive, from a user device or from one or more electronic databases, data representative of a user-selected dietary program selected from a plurality of dietary programs. The processing system is configured to output a nutritional index indicative of an alignment between the person's diet over a predetermined time period and the selected dietary program. The processing system is configured to output data representative of a predicted change in the nutritional index based on the meal recommendation.

In some implementations, the processing system is configured to generate the meal recommendation by selecting, for each of the one or more meals, a recommended number of servings of each of the one or more foods in the meal, the recommended number of servings selected as the modified portion size to reduce a deviation between the nutrient levels of the selected meal and the target nutritional profile.

In some implementations, the modified portion size is based on a constraint associated with a desired distribution of the first and second nutrients over a predetermined period of time or within the selected meal. The desired distribution includes a per-meal constraint for each of a plurality of nutrients including the first and second nutrients. The first and second nutrients are selected from the group consisting of carbohydrates, fats, protein, and fiber. The desired distribution is based on a history of a distribution of the first and second nutrients across the one or more meals eaten during a predetermined time period.

In some implementations, the constraint includes a requirement that the recommended number of servings of a food be less than or equal to a predetermined multiple of a maximum number of servings of the food previously consumed by the person.

In some implementations, a nutritional index is generated by selecting a specific weight for each of the first and second nutrients and applying a weighted function to those weights, the specific weight being based on a comparison between an amount of each of the first and second nutrients in the selected meal and the target level of the respective nutrient. Each of the one or more meals corresponds to a classification selected from the group consisting of breakfast, brunch, lunch, dinner, and snack. The processing system may be configured to generate the meal recommendation by modifying the selected meal based on a caloric allowance associated with the classification of the selected meal. Each of the one or more meals may correspond to the same classification.

In some implementations, the processing system is configured to output a consumption profile for the person, including a first consumed nutrient indicator for the first nutrient and a second consumed nutrient indicator for the second nutrient, wherein each of the first and second consumed nutrient indicators is indicative of an excess or a deficit determined based on the target levels of the first and second nutrients and the one or more meals.

Another aspect relates to a system for aligning a person's diet with specific dietary goals. The system includes a first data port configured to receive first input data representative of a dietary program for the person and second input data representative of a plurality of foods consumed by the person during a first time period include a plurality of days, each of the one or more foods associated with a calendar date within the first time period and a second data port configured to communicate with a processing system, the processing system including: a server, one or more electronic databases configured to store data representative of target levels of first and second nutrients in each of one or more dietary programs, and data representative of amounts of the first and second nutrients in each of the plurality of foods. The system includes processing circuitry, in communication with the first and second data ports, configured to output the first and second input data to the processing system over a communication network. The processing circuitry is also configured to receive, from the processing system, a nutritional index representative of an alignment between the person's diet during the first time period and a dietary program identified by the server from a plurality of dietary programs based on the first input data, the nutritional index based on the amounts of the first and second nutrients in the plurality of foods and the target levels of the first and second nutrients in the dietary program, receive, from the server, a recommendation for a food and a recommended amount of the food to be consumed during a second time period based on the nutritional index and the dietary program, and output the nutritional index and the recommendation to the user interface device via the first data port.

In some implementations, the processing system is configured to modify the selected dietary program based on two or more of a nutritional goal, a weight goal, an exercise goal, or a medical condition for the person. The one or more electronic databases are configured to store information indicative of meals previously consumed by the person, each meal including a combination of the plurality of foods, and wherein the processing system is configured to provide the recommendation by selecting one of the meals.

In some implementations, the processing system is configured to provide data representative of a graphical nutrient profile for the person, the graphical nutrient profile including a graphical indicator for each of the first and the second nutrients, each graphical indicator indicating whether the person's consumption of the respective nutrient during the first time period is in deficit or excess of the respective target level for that nutrient.

In some implementations, the one or more electronic databases are part of a distributed database including a first electronic database configured to store the data representative of target levels of first and second nutrients in each of the plurality of dietary programs, a second electronic database configured to store data representative of amounts of the first and second nutrients in each of the plurality of foods, and a third electronic database configured to store data representative of meals previously consumed by the person, each meal including a combination the one or more foods.

In some implementations, the processing circuitry, the first data port, and the second data port are housed in a user interface device. The user interface device includes a GPS-enabled mobile device, and wherein the first data port is configured to receive a third input data representative of one or more locations detected using the GPS over a predefined period of time. The first data port is configured to receive the second input data in response to a prompt provided to the user to identify one or more foods consumed at the one or more locations.

Another aspect relates to a method for providing a menu recommendation to a visitor of a restaurant, which the visitor can use to decide what menu options to order in order to comply with the visitor's nutritional goals. The method includes receiving, in one or more computers, a plurality of menu options for dishes, foods, or meals served by the restaurant. The menu options may be organized within a database of a computer or on a network accessible by a computer and are characterized into a plurality of option types for example, appetizers, entrees, beverages, side dishes, lunch menu items, vegetarian items, meat items, or any other suitable type of an item on a restaurant menu. The method also includes receiving data in the computer that is indicative of the visitor's desired meal configuration, including one or more option types selected from the plurality of option types. The method also includes providing, on an output port of the one or more computers, one or more combinations of menu options generated based on the desired meal configuration, each combination including at least one menu option corresponding to the one or more option types in the desired meal configuration, and providing, simultaneously with each of the one or more combinations, a predicted index impact of the respective combination on a nutritional index for the visitor, wherein the nutritional index corresponds to an aggregate alignment between the visitor's diet over a first time period, a user-selected dietary program, and a goal or condition for the visitor.

In some implementations, the method includes providing the nutritional index, simultaneously with providing the one or more combinations and the respective predicted index impacts. The method includes receiving a selection of one or more of the combinations of menu options, storing the one or more selected combinations in at least one electronic database in communication with the one or more computers, and updating the nutritional index to reflect the selected combination as a consumed meal.

In some implementations, the method includes receiving a target nutritional profile for the visitor. The target nutritional profile includes target levels of a first nutrient and a second nutrient (or more nutrients), the target levels being determined based on the user-selected dietary program and the goal or condition. The method also includes a step of receiving data indicative of consumed amounts for the first and second nutrients during the first time period, and generating the nutritional index based on deviations between the consumed amounts and the respective target levels for each of the first and second nutrients.

In some implementations, providing the one or more combinations includes receiving nutritional information for the plurality of menu options, including an amount of each of the first and second (or more) nutrients in the menu option and generating a plurality of candidate combinations. Candidate combinations may include any combination of items on the menu. Each candidate combination may include a plurality of candidate menu options based on the option types in the desired meal configuration. A candidate menu option may be a menu of an option type such as an appetizer, an entrée, a dessert, or a beverage, for example. Providing the one or more combinations includes determining, for each candidate combination, a total candidate amount of each of the first and second nutrients in the candidate menu options. A candidate deviation from the target level for each of the first and the second nutrients is preferably determined based on the consumed amounts, the total candidate amounts, and the target level for the respective first and second nutrients. As an example, a candidate deviation may include a difference or a ratio (or any of the other ways of determining a deviation described herein, used alone or in combination with others) between the target level of a nutrient and an amount of that nutrient in the food(s) of the candidate combination. The target level of the nutrient may be based on a previously consumed amount of that nutrient to account for foods previously consumed by the user. A candidate index impact is preferably determined based on the nutritional index, wherein the candidate index impact is based on a weighted function of the candidate deviations.

In some implementations, providing the one or more combinations includes selecting from the candidate combinations a set of combinations of foods, dishes, or meals, that each (because of its particular nutritional content) correspond to an index impact greater than or equal to a threshold and providing, on the output port, the set of combinations in an order corresponding to the index impact. Those combinations represent candidates of foods, dishes, or meals (including serving sizes or portion sizes) that would be ordered by the person. Generating that list of candidate combinations may include at least one menu option with a modified portion size, as compared to the serving size provided by the restaurant. The method may provide, simultaneously with the one or more combinations, an electronic signal or other indicator of the modified portion size.

In some implementations, the plurality of menu options to be recommended to the person includes two or more option types selected from the group of appetizer, entree, salad, beverage, dessert, and side dish.

In some implementations, the one or more computers includes a GPS-enabled mobile device in communication with a processing system that provides location-based information for a plurality of restaurants geographically near where a person is located or plans to eat. The method includes a step of automatically detecting, based on the location of the mobile device, that the visitor has entered a restaurant, and in response to that detecting step, automatically prompting the visitor to provide his or her desired meal configuration.

Another aspect relates to a method of aligning a person's exercise routine with the person's exercise, nutritional, or other health related goals. The method may be performed by one or more computers with an electronic database and a communications port. The method includes the steps of receiving, by the one or more computers, a first data input indicative of an amount of exercises performed by the person over a first time period, wherein the exercises include a plurality of exercise types, receiving from the at least one electronic database a second data input indicative of an exercise program selected based on one or more health-related goals for the person, and specifying target amounts for the plurality of exercise types, the exercise program including a desired distribution over time for the plurality of exercise types. An exercise type can be defined in any number of ways. For example, an exercise type defined broadly based on the kind of physical or mental benefit that the physical activity is intended to provide (e.g., aerobic exercises, flexibility exercises, balance exercises, strength training, endurance training, etc.), based on the part of the body intended be benefited (e.g., leg exercises, abdominal exercises, shoulder exercises, etc.), based on a specific physical activity (e.g., running, biking, swimming, walking, lunges, weight-lifting, tennis, etc.), or based on a combination of any two or more of the foregoing. In some implementations, the exercise types include at least two exercise types selected from the group strength exercises, flexibility exercises, aerobic exercises, endurance exercises, balance exercises, and any suitable combination thereof. In some implementations, the target amounts for the plurality of exercise types include a parameter selected from duration, intensity, frequency, anatomical focus, and any suitable combination thereof. For each of the plurality of exercise types, the method may include (1) generating a deviation for the exercise type based on comparing the amount of the exercise type to the target amount associated with the exercise type and the desired distribution, and (2) determining a numeric weight associated with the exercise type. The method may also output on the communications port output data indicative of an alignment between the exercises performed and the exercise program, based on the respective deviation and numeric weight for each of the exercise types.

In some implementations, the output data includes an aggregate exercise index generated based on a weighted function of the deviations and numeric weights. Determining the numeric weight for each exercise type may include assigning to the exercise type a first numeric weight if the amount of the exercise type exceeds the target amount, and assigning to the exercise type a second numeric weight if the amount of the exercise type does not exceed the target amount. The first data input may be received from an exercise monitoring device associated with the person, such as a mobile device, an activity level tracker, or a physiological monitoring device.

In some implementations, the method provides a recommended exercise to be performed by the person to change the alignment between the person's exercise routine with the person's exercise, nutritional, or other health related goals. The recommended exercise may be selected by taking into account one or more factors specific to the user, such as age, gender, medical condition, physical injuries, historic level of physical activity, available exercise equipment, geographic location of the user, user-specified preferences, etc. In such cases, the recommended exercise may be selected to reduce a deviation associated with the person's exercise and the exercise routine. For example, the recommended exercise may be selected to reduce a deviation associated with each of at least two or more exercise types. In some implementations, the recommended exercise is selected from exercises previously performed by the person. In other implementations, the recommended exercise is not selected from the plurality of exercises previously performed by the person.

In some implementations, the method outputs on the communications port a nutritional index indicative of an alignment between amounts of a plurality of nutrients consumed by the person during the first time period and a target nutritional profile, wherein the target nutritional profile includes a plurality of target amounts for the plurality of nutrients. In other aspects, the nutritional and exercise analyses can be used in combination, to provide a combined index. In order to provide the nutritional index, methods are provided that receive information indicative of a person's nutritional goals, including target nutrient levels or target foods, dishes, or meals that satisfy those goals, information indicative of nutrients, foods, dishes, or meals to be consumed by the person, information indicative of the person's exercise targets, and information indicative of the person's exercise goals. The method can also include providing to the person a wellness index based on the exercise index and the nutritional index, either alone or simultaneously with the exercise index, the nutritional index, or both. The method may include generating the wellness index using any one of the approaches described herein, alone or in combination with others. For example, the method may include generating the wellness index as a weighted function of the nutritional index and the exercise index by selecting a numeric nutrition weight for the nutritional index and a numeric exercise weight for the exercise index based on the one or more health-related goals for the person.

Another aspect relates to a system for assessing a person's diet. The system includes means for receiving data representative of an amount of a first nutrient that has been or may be consumed by the person during a first predetermined time period, and means for receiving a target level of the first nutrient. The system also includes means for assigning a first numeric weight to the first nutrient based on a comparison between the amount of the nutrient and the target level of that nutrient, and a means for providing an assessment of the person's diet based on the first numeric weight.

In some implementations, the system includes means for receiving a user-selected dietary program selected from a plurality of dietary programs, and wherein the target level is determined based on the user-selected dietary program. The user-selected dietary program may include at least one each of a weight goal and a nutrition goal for the person. The means for assigning the first numeric weight may include means for selecting from a plurality of nutrient-specific weights for the first nutrient, where the nutrient-specific weights are determined based on the weight goal or the nutritional goal.

Of course, the system can be applied to a plurality of nutrients to help the person align her diet, exercise, and other health practices with her goals. In some implementations, the system includes means for receiving a target level of a second nutrient and means for receiving an amount of the second nutrient consumed by the person. The system also includes means for assigning a second numeric weight to the second nutrient based on a comparison between the consumed amount of the second nutrient and the target level of the second nutrient, wherein providing the assessment of the person's diet includes providing the assessment based on the first and second numeric weights. The means for providing an assessment of the person's diet may include means for providing a first indicator of an alignment between the target level of the first nutrient and the consumed amount of the first nutrient, means for providing a second indicator of an alignment between the target level of the second nutrient and the consumed amount of the second nutrient, and means for providing a nutritional index representative of an aggregate alignment between the user-selected dietary program and person's diet based on the respective alignments of the first and second nutrients. The first and second indicators may be graphical indicators, each graphical indicator indicating whether the person's consumption of the respective nutrient is in deficit or in excess of the respective target level. The system may include means for providing a recommendation for the person to consume a recommended food selected from one or more foods based on a predicted change in the nutritional index. The recommended food may be selected to change the first indicator and to simultaneously reduce a negative impact on the alignment of the second nutrient.

In some implementations, the means for providing the assessment includes means for providing the assessment based on respective consumed amounts and target levels of three or more nutrients. The means for providing the nutritional index may include means for calculating, for each of the three or more nutrients, a deviation for each nutrient based on the consumed amount of that nutrient and its target level. The recommended food may be selected to simultaneously reduce the deviation for each of the three or more nutrients. In certain implementations, the system processes nutrient levels and target nutrient levels for up to 10, up to 20, up to 100, up to 1000, or up to 10,000 nutrients and combinations of nutrients. In doing so, the system determines an index based on those nutrients by assessing the deviation of each in relation to its respective target level, and making recommendations for foods, dishes, or meals that will change that index to better align the person's meals with the goals.

In some implementations, the recommended food is selected from one or more foods previously consumed by the person. The means for providing the recommendation includes means for providing a recommended amount of the recommended food and a recommended calendar date for the person to consume the recommended food, the recommended amount being different from a previously consumed amount of the recommended food.

In some implementations, the recommended food is selected from one or more foods not previously consumed by the person. The system includes means for selecting a recommended food from the one or more foods not previously consumed by the person in response to determining that selecting from the one or more foods previously consumed by the person does not provide a substantial improvement in the nutritional index.

In some implementations, the system includes means for receiving data representative of a medical condition of the person and means for modifying the target level of the first nutrient or the first numeric weight based on one or more dietary restrictions associated with the medical condition. The one or more dietary restrictions may include a desired distribution of a plurality of nutrients during the first predefined time period. The desired distribution may correspond to two or more nutrients selected from the group consisting of calories, carbohydrates, proteins, fat, and fiber.

In some implementations, the system includes means for generating the target level of the first nutrient based on an actual or estimated amount of exercise performed by the person during the first predetermined time period.

Another aspect relates to a system for providing a menu recommendation to a visitor of a restaurant. The system includes means for receiving a plurality of menu options for the restaurant, the menu options characterized into a plurality of option types and means for receiving data indicative of the visitor's desired meal configuration, including one or more option types selected from the plurality of option types. The system includes means for providing one or more combinations of menu options generated based on the desired meal configuration, each combination including at least one menu option corresponding to the one or more option types in the desired meal configuration, and means for providing, simultaneously with each of the one or more combinations, a predicted index impact of the respective combination on a nutritional index for the visitor, wherein the nutritional index corresponds to an aggregate alignment between the visitor's diet over a first time period, a user-selected dietary program, and a goal or condition for the visitor.

In some implementations, the system includes means for providing, simultaneously with the one or more combinations and the respective predicted index impacts, the nutritional index. The system includes means for receiving a selection of one of the combinations of menu options, means for storing the selected combination in at least one electronic database in communication with the one or more computers, and means for updating the nutritional index to reflect the selected combination as a consumed meal.

In some implementations, the system includes means for receiving for the visitor a target nutritional profile including target levels of a first nutrient and a second nutrient, the target levels determined based on the user-selected dietary program and the goal or condition, means for receiving consumed amounts for the first and second nutrients during the first time period, and means for generating the nutritional index based on a deviation between the consumed amounts and the target level for each of the first and second nutrients. The means for providing the one or more combinations includes means for receiving nutritional information for the plurality of menu options, including an amount of each of the first and second nutrients in the menu option, means for generating a plurality of candidate combinations, each candidate combination including a plurality of candidate menu options based on the option types in the desired meal configuration, and means for determining, for each candidate combination, a total candidate amount of each of the first and second nutrients in the candidate menu options, a candidate deviation from the target level for each of first and the second nutrient based on the consumed amounts, the total candidate amounts, and the target level for the respective first and second nutrients, and a candidate index impact on the nutritional index, wherein the candidate index impact is based on a weighted function of the candidate deviations. In some implementations, the means for providing the one or more combinations includes means for selecting from the candidate combinations a set of combinations that each correspond to an index impact greater than or equal to a threshold, and means for providing the set of combinations in an order corresponding to the index impact. The means for generating the candidate combinations may include means for generating at least one candidate combination that includes at least one menu option having a modified portion size from the serving size provided by the restaurant. The system may include means for providing, simultaneously with the one or more combinations, an indicator of the modified portion size.

In some implementations, the plurality of options types includes two or more option types selected from the group consisting of appetizer, entree, salad, beverage, dessert, and side dish.

In some implementations, the system includes a GPS-enabled mobile device that provides location-based information for a plurality of restaurants, means for automatically detecting, based on the location of the mobile device, that the visitor has entered a restaurant, and in response to the detecting, means for prompting the visitor to provide the desired meal configuration.

Another aspect relates to a system including means for receiving a first data input indicative of amounts of exercises performed by the person over a first time period, wherein the exercises include a plurality of exercise types and means for receiving a second data input indicative of an exercise program selected based on one or more health-related goals for the person and specifying target amounts for the plurality of exercise types, the exercise program including a desired distribution over time for the plurality of exercise types. For each of the plurality of exercise types, the system includes (1) means for generating a deviation for the exercise type based on comparing the amount of the exercise type to the target amount associated with the exercise type and the desired distribution, and (2) means for determining a numeric weight associated with the exercise type. The system includes means for outputting data indicative of an alignment between the exercises performed and the exercise program based on the respective deviation and numeric weight for each of the exercise types.

In some implementations, the output data includes an aggregate exercise index generated based on a weighted function of the deviations and numeric weights. The means for determining the numeric weight for each exercise type may include means for assigning to the exercise type a first numeric weight if the amount of the exercise type exceeds the target amount, and means for assigning to the exercise type a second numeric weight if the amount of the exercise type does not exceed the target amount. The means for receiving the first data input may include means for receiving the first data input from an exercise monitoring device associated with the person. The exercise monitoring device may include a mobile device, an activity level tracker, or a physiological monitoring device.

In some implementations, the system includes means for providing a recommended exercise to be performed by the person to change the alignment. The recommended exercise is selected to reduce the deviation for each of at least two of the plurality of exercise types. In some implementations, the recommended exercise is selected from the plurality of exercises previously performed by the person. In other implementations, the recommended exercise is not selected from the plurality of exercises previously performed by the person.

In some implementations, the target amounts for the plurality of exercise types include a parameter selected from the group consisting of duration, intensity, frequency, anatomical focus, and any suitable combination thereof.

In some implementations, the plurality of exercise types include at least two of strength exercises, flexibility exercises, aerobic exercises, endurance exercises, balance exercises, and any suitable combination thereof.

In some implementations, the system includes means for outputting a nutritional index indicative of an alignment between amounts of a plurality of nutrients consumed by the person during the first time period and a target nutritional profile, wherein the target nutritional profile includes a plurality of target amounts for the plurality of nutrients. The system includes means for providing to the person, simultaneously with the exercise index and the nutritional index, a wellness index generated based on the exercise index and the nutritional index. The system may include means for generating the wellness index as a weighted function of the nutritional index and the exercise index by selecting a numeric nutrition weight for the nutritional index and a numeric exercise weight for the exercise index based on the one or more health-related goals for the person.

Another aspect relates to a system for assessing a person's diet. The system includes means for receiving data representative of an amount of each of three or more nutrients consumed by the person, means for receiving a target level for each of the three or more nutrients, means for assigning a plurality of numeric weights to the three or more nutrients such that each of the nutrients is assigned a numeric weight determined based on a comparison between the amount of the respective nutrient and the target level of the respective nutrient, and means for providing an assessment of the person's diet based on the plurality of numeric weights.

In some implementations, the system includes means for receiving a user-selected dietary program selected from a plurality of dietary programs, and wherein the target level for each of the three or more nutrients is determined based on the user-selected dietary program. The means for assigning the plurality of numeric weights may include means for assigning the numeric weight for each of the nutrients from a nutrient-specific set of numeric weights determined based on one or more goals associated with the person.

In some implementations, the three or more nutrients include a first nutrient and a second nutrient. The means for providing an assessment of the person's diet includes means for providing a first indicator of an alignment between the amount of the first nutrient and the target level of the first nutrient, means for providing a second indicator of an alignment between the amount of the second nutrient and the target level of the second nutrient, and means for providing a nutritional index representative of an aggregate alignment between the user-selected dietary program and the person's diet based on the respective alignments of the first and second nutrients. The system may include means for providing a recommendation for the person to consume a recommended food selected from one or more foods based on a predicted change in the nutritional index. The recommended food may be selected to change the first indicator and to simultaneously reduce a negative impact on the alignment of the second nutrient.

In some implementations, the means for providing the nutritional index includes means for calculating, for each of the three or more nutrients, a deviation for the nutrient based on the consumed amount of the nutrient and the target level of the nutrient. The recommended food may be selected to simultaneously reduce the deviation for each of at least two of the three or more nutrients.

In some implementations, the system includes means for selecting the recommended food based on a desired consumption distribution of the three or more nutrients over a predetermined time period. The recommended food may be selected from one or more foods previously consumed by the person. The means for providing the recommendation may include means for providing a recommended amount of the recommended food and a recommended calendar date for the person to consume the recommended food, the recommended amount being different from a previously consumed amount of the recommended food. The recommended food may be selected from one or more foods not previously consumed by the person.

In some implementations, the system includes means for generating the target level of at least one of the three or more nutrients based at least in part on an actual or estimated amount of exercise performed by the person during a predetermined time period. The system may include means for storing a set of nutrient-specific weights for each of the three or more nutrients, each nutrient-specific weight corresponding to a different time period for the nutrient and means for selecting the plurality of numeric weights from the nutrient-specific weights based on a first predetermined time period for which the assessment is provided.

Another aspect relates to a method for providing a meal recommendation to a group including two or more members. A computer system, including a communications port and at least one computer processor in communication with at least one non-transitory computer-readable medium storing an electronic database, receives first data input indicative of a plurality of target nutritional profiles including a plurality of nutrients including a first nutrient, each target nutritional profile being associated with at least one member of the group and including a target level of the first nutrient determined, based on one or more selected dietary programs, for the at least one member. The computer system receives second data input indicative of a plurality of priority weights, including a priority weight for each member of the group, the priority weight indicative of an importance of a nutritional goal of the member relative to that of other members of the group. The method includes assigning, for each member of the group, a first nutrient-specific weight to the first nutrient, the first nutrient-specific weight determined based on (1) the nutritional goal of the respective member and (2) a comparison of an amount of the first nutrient consumed by the respective member to the target level of the first nutrient for the respective member. A recommendation is provided via the communications port, the recommendation including at least one recommended meal to be consumed by the group, the recommended meal selected based on the first nutrient-specific weights and the plurality of priority weights.

In some implementations, the method includes receiving by the computer system third data input indicative of a nutrient consumption profile for each member of the group, each nutrient consumption profile including an amount of at least one nutrient in the subset of nutrients in the member's target profile consumed by the member during a predetermined time period. Providing the recommendation may include selecting the at least one recommended meal to change a first alignment between the nutrient consumption profile and the target nutritional profile for a first member of the group. Providing the recommendation may include selecting the at least one recommended meal to improve the first alignment between the nutrient consumption profile and the target nutritional profile for the first member and to simultaneously maintain or improve a second alignment for a second member of the group.

In some implementations, the method includes generating, for each member of the group, a deviation profile based on comparing the target nutritional profile for the member to a nutrient consumption profile for the member such that each deviation profile includes, for each nutrient in the target profile for the member, an excess or a deficit indicator for the nutrient. The method may include generating an aggregate deviation as a function of a weighted combination of each deviation profile with the priority weight for the respective member, such that the aggregate deviation reflects a relative importance of the deviation profiles in accordance with the priority weights. Providing the recommendation may include selecting the at least one recommended meal to minimize the aggregate deviation generated based on combining the deviation profiles.

In some implementations, the method includes providing a group nutritional index representative of a collective alignment between the consumption profile for each member and the target nutritional profile for the respective member. Providing the group index includes applying, for each member in the group, the priority weight associated with the member to the deviation profile for the respective member to obtain a weighted deviation and combining the weighted deviations to obtain the group nutritional index. The at least one recommended meal may be selected to change the group nutritional index while simultaneously reducing a negative impact on the alignment between the consumption profile for each member and the target nutritional profile for the respective member.

In some implementations, providing the recommendation includes detecting an incompatibility between the plurality of deviation profiles and determining, based on the incompatibility, a minimum plurality of distinct meals to recommend as the at least one recommended meal.

In some implementations, the method includes providing via the communications port an indicator of an index impact on a nutritional index for at least one member of the group, wherein the nutritional index is indicative of an alignment between the consumption profile for the at least one member and the target nutritional profile for the respective member, and the index impact is indicative of a predicted change to the nutritional index if the member consumes the at least one recommended meal. Providing the indicator of the index impact may include providing a plurality of indicators of the index impact including at least one index impact for each member of the group. The method may include providing via the communications port an indicator of the nutritional index for the at least one member.

In some implementations, the method includes generating a plurality of candidate meals, each candidate meal including one or more candidate foods and selecting the at least one recommended meal from the plurality of candidate meals based on a comparison between an amount of the first nutrient in each candidate meal and a deviation for the first nutrient in at least one deviation profile. The at least one recommended meal may be selected based on a parameter associated with each candidate meal, the parameter selected from the group consisting of: a number of dishes, a number of foods, an amount of preparation time, a level of complexity of preparation, cost of ingredients, and availability of ingredients.

Another aspect relates to a system for providing a meal recommendation to a group including two or more members. The system includes means for receiving first data input indicative of a plurality of target nutritional profiles including a plurality of nutrients including a first nutrient. Each target nutritional profile is associated with at least one member of the group and includes a target level of the first nutrient determined, based on one or more selected dietary programs, for the at least one member. The system also includes means for receiving second data input indicative of a plurality of priority weights, including a priority weight for each member of the group, the priority weight indicative of an importance of a nutritional goal of the member relative to that of other members of the group. The system also includes means for assigning, for each member of the group, a first nutrient-specific weight to the first nutrient, the first nutrient-specific weight determined based on (1) the nutritional goal of the respective member and (2) a comparison of an amount of the first nutrient consumed by the respective member to the target level of the first nutrient for the respective member. The system includes means for providing a recommendation including at least one recommended meal to be consumed by the group, the recommended meal selected based on the first nutrient-specific weights and the plurality of priority weights.

In some implementations, the system includes means for receiving third data input indicative of a nutrient consumption profile for each member of the group, each nutrient consumption profile including an amount of at least one nutrient in the subset of nutrients in the member's target profile consumed by the member during a predetermined time period. The means for providing the recommendation may include means for selecting the at least one recommended meal to change a first alignment between the nutrient consumption profile and the target nutritional profile for a first member of the group. The means for providing the recommendation may include means for selecting the at least one recommended meal to improve the first alignment between the nutrient consumption profile and the target nutritional profile for the first member and to simultaneously maintain or improve a second alignment for a second member of the group.

In some implementations, the system includes means for generating, for each member of the group, a deviation profile based on comparing the target nutritional profile for the member to the nutrient consumption profile for the member such that each deviation profile includes, for each nutrient in the target profile for the member, an excess or a deficit indicator for the nutrient. The system may include means for generating an aggregate deviation as a function of a weighted combination of each deviation profile with the priority weight for the respective member, such that the aggregate deviation reflects a relative importance of the deviation profiles in accordance with the priority weights. The means for providing the recommendation may include means for selecting the at least one recommended meal to minimize the aggregate deviation generated based on combining the deviation profiles.

In some implementations, the system includes means for providing a group nutritional index representative of a collective alignment between the consumption profile for each member and the target nutritional profile for the respective member. The means for providing the group index may include means for applying, for each member in the group, the priority weight associated with the member to the deviation profile for the respective member to obtain a weighted deviation and means for combining the weighted deviations to obtain the group nutritional index. The recommended meal may be selected to change the group nutritional index while simultaneously reducing a negative impact on the alignment between the consumption profile for each member and the target nutritional profile for the respective member.

In some implementations, the means for providing the recommendation includes means for detecting an incompatibility between the plurality of deviation profiles and means for determining, based on the incompatibility, a minimum plurality of distinct meals to recommend as the at least one recommended meal.

In some implementations, the system includes means for providing an indicator of an index impact on a nutritional index for at least one member of the group, wherein the nutritional index is indicative of an alignment between the consumption profile for the at least one member and a target nutritional profile for the respective member, and the index impact is indicative of a predicted change to the nutritional index if the member consumes the at least one recommended meal. The means for providing the indicator of the index impact may include means for providing a plurality of indicators of the index impact including at least one index impact for each member of the group. The system may include means for providing via the output port an indicator of the nutritional index for the at least one member.

In some implementations, the system includes means for generating a plurality of candidate meals, each candidate meal including one or more candidate foods and means for selecting the at least one recommended meal from the plurality of candidate meals based on a comparison between an amount of the first nutrient in each candidate meal and a deviation for the first nutrient in at least one deviation profile. The at least one recommended meal may be selected based on a parameter associated with each candidate meal, the parameter selected from the group consisting of: a number of dishes, a number of foods, an amount of preparation time, a level of complexity of preparation, cost of ingredients, and availability of ingredients.

Another aspect relates to a method for rating a food recommendation provided by the user or a third party. According to this aspect, the user can, for example, receive an assessment of a recommendation provided by diet service that takes into account the user's nutrition, exercise, wellness, and other health goals. One advantage of such a rating feature is that the user can monitor their nutritional intake using a single system without being required to adhere to a single source of a dietary regimen. Thus, the user can obtain from a single source an assessment of whether specific food(s) recommended by several third-party services (e.g., Jenny Craig™, Weight Watchers™, Lean Cuisine™, etc.) would be consistent with the user's goals and constraints or conditions. This is an especially useful aspect that may be used alone or in combination with the recommendations provided by the method based on the user's nutritional index. By providing an option for the user to receive ratings on foods recommended by third parties, the user is able to apply a consistent rating standard or mechanism to recommendations from multiple sources without taking on the arduous task of providing of specifying consistent goals or requirements across multiple platforms. The method includes receiving, by a computer system including a communications port and at least one computer processor in communication with at least one non-transitory computer readable medium storing at least one electronic database, first input data representative of a food recommendation to a person. The food can include be meal, or other combination of one or more foods, and the recommendation can include a suggested portion size, and an amount of each of a first and a second nutrient in the suggested portion size. The computer system receives second input data representative of a nutrient consumption profile for the person. The second input data includes an indicator of a consumed amount for the first and second nutrients over a predetermined time period. The method also includes receiving from the at least one electronic database third input data representative of a target nutrition profile for a person. The target nutrition profile includes target levels of the first and second nutrients. For each nutrient, the target level is indicative of a suggested or required amount of the nutrient over the predetermined time period and is determined according to a user-specified nutritional goal. A first numeric weight is assigned to the first nutrient, the first numeric weight being determined based on (1) the user-specified nutritional goal and (2) a comparison of the consumed amount of the first nutrient to the target level of the first nutrient. A second numeric weight is assigned to the second nutrient, the second numeric weight being determined based on (1) the user-specified nutritional goal and (2) a comparison of the consumed amount of the second nutrient to the target level of the second nutrient. Based on the first and second numeric weights, a suitability rating is generated, where the suitability rating is representative of an alignment between the food recommendation and the nutritional goal, and the suitability rating for the food recommendation is provided via the communications port.

In some implementations, the method includes receiving, over a communications network, the first input data from a user device or from a remote computer system. The method can generate an index impact of the food recommendation based on a nutritional index associated with the person, wherein the nutritional index is indicative of an alignment between the consumption profile and the target nutritional profile, and the index impact is indicative of a predicted change to the nutritional index from following the food recommendation. The computer system may be programmed to include a plurality of threshold ranges, and wherein providing the suitability rating includes providing on the communications port in which selected range of the threshold ranges the index impact lies.

In some implementations, providing the suitability rating includes providing a color-coded indicator corresponding to the selected range. Providing the suitability rating may include providing the index impact simultaneously with the color-coded indicator. The threshold ranges may include at least three ranges including a cautionary range. Thus, in some examples, the method generates using the computer system an index impact, then selects from one of the threshold ranges based on the value on the index impact. The threshold range may be mapped to a specific color (e.g., green for approved, yellow to signify caution, and red to signify an incompatibility with a goal or condition for the person).

In some implementations, the method includes generating a deviation profile including, for each of the first and second nutrients, an excess or a deficit indicator for the nutrient determined based on comparing the consumed amount of the nutrient to a target level for the respective nutrient. The method also includes providing the suitability rating based on the deviation profile and the first and second numeric weights.

In some implementations, assigning the first numeric weight to the first nutrient includes selecting from a first plurality of nutrient-specific weights associated with the first nutrients including one or more numeric weights selected in response to detecting an excess of the first nutrient and one or more numeric weights selected in response to detecting a deficit of the first nutrient. Assigning the first numeric weight to the first nutrient may include selecting from a second plurality of nutrient-specific weights associated with the first nutrient based on the predetermined time period. The second plurality of nutrients may include a per-meal weight, a weekly weight, and a daily weight for the first nutrient.

In some implementations, the target level for each of the first and second nutrients is determined according to an additional one of a weight goal and a medical condition associated with the person. The method may include receiving a user-selected dietary program selected from a plurality of dietary programs stored in the at least one electronic database. The target level for each of the first and second nutrients is determined based on the selected dietary program.

In some implementations, the method includes providing a substitute food recommendation based on the suitability rating. Providing the substitute food recommendation includes recommending a modified version of the combination of one or more foods. The modified version of the combination may include a modified suggested portion size. The modified version of the combination may include inclusion of an additional food not included in the combination. The modified version of the combination may include removing at least one of the one or more foods from the combination.

In some implementations, a system includes at least one computer processor, a communications port, and at least one non-transitory computer readable medium storing an electronic database. The system is adapted to perform any of the methods described herein.

Another aspect relates to a system for rating a recommended food provided by the user or a third-party service or system. The food may be recommended for a user by a third party, and the system provides an assessment of an impact on an alignment between the user's diet and the user's dietary goals. The system includes means for receiving first input data representative of a food recommendation to a person, including a combination of one or more foods, a suggested portion size, and an amount of each of a first and a second nutrient in the suggested portion size. The system also includes means for receiving second input data representative of a nutrient consumption profile for the person. The second input data includes an indicator of a consumed amount for the first and second nutrients over a predetermined time period. The system includes means for receiving third input data representative of a target nutrition profile for a person. The target nutrition profile includes target levels of the first and second nutrients, and the target level for each nutrient is indicative of a suggested or required amount of the nutrient over the predetermined time period. The target level is determined according to a user-specified nutritional goal. The system includes means for assigning to the first nutrient a first numeric weight determined based on (1) the user-specified nutritional goal and (2) a comparison of the consumed amount of the first nutrient to the target level of the first nutrient, and means for assigning to the second nutrient a second numeric weight determined based on (1) the user-specified nutritional goal and (2) a comparison of the consumed amount of the second nutrient to the target level of the second nutrient. The system includes means for generating based on the first and second numeric weights a suitability rating representative of an alignment between the food recommendation and the nutritional goal and means for providing the suitability rating for the food recommendation.

In some implementations, the means for receiving the first input data representative of the food recommendation includes means for receiving, over a communications network, the first input data from a user device or from a remote computer system. The means for generating the suitability rating may include means for generating an index impact of the food recommendation on a nutritional index associated with the person. The nutritional index is indicative of an alignment between the consumption profile and the target nutritional profile, and the index impact is indicative of a predicted change to the nutritional index from following the food recommendation. The means for providing the suitability rating may include means for providing in which selected range of a plurality of threshold ranges the index impact lies. The means for providing the suitability rating may include means for providing a color-coded indicator corresponding to the selected range. The means for providing the suitability rating may include means for providing the index impact simultaneously with the color-coded indicator. The plurality of threshold ranges includes at least three ranges including a cautionary range.

In some implementations, the system includes means for generating a deviation profile including, for each of the first and second nutrients, an excess or a deficit indicator for the nutrient determined based on comparing the consumed amount of the nutrient to a target level for the respective nutrient and means for providing the suitability rating based on the deviation profile and the first and second numeric weights.

In some implementations, the means for assigning the first numeric weight to the first nutrient includes means for selecting from a first plurality of nutrient-specific weights associated with the first nutrients including one or more numeric weights selected in response to detecting an excess of the first nutrient and one or more numeric weights selected in response to detecting a deficit of the first nutrient.

In some implementations, the means for assigning the first numeric weight to the first nutrient includes means for selecting from a second plurality of nutrient-specific weights associated with the first nutrient based on the predetermined time period. The second plurality of nutrients may include a per-meal weight, a weekly weight, and a daily weight for the first nutrient.

In some implementations, the target level for each of the first and the second nutrients is determined according to an additional one of a weight goal and a medical condition associated with the person.

In some implementations, the system includes means for receiving a user-selected dietary program selected from a plurality of dietary programs, and the target level for each of the first and second nutrients is determined based on the selected dietary program.

In some implementations, the system includes means for providing a substitute food recommendation based on the suitability rating. The means for providing the substitute food recommendation may include means for recommending a modified version of the combination of one or more foods. The modified version of the combination may include a modified suggested portion size. The modified version of the combination may include inclusion of an additional food not included in the combination. The modified version of the combination may include removing at least one of the one or more foods from the combination.

Another aspect relates to a method for assessing a person's diet. The method is performed by a computer system including at least one computer processor and a communications port. The method includes receiving by the computer system data representative of an amount of each of three or more nutrients consumed by the person and receiving from at least one electronic database a target level for each of the three or more nutrients. The method includes assigning by the computer system a plurality of numeric weights to the three or more nutrients such that each of the nutrients is assigned a numeric weight determined based on a comparison between the amount of the respective nutrient and the target level of the respective nutrient, and providing via the communications port an assessment of the person's diet based on the plurality of numeric weights.

In some implementations, the method includes receiving a user-selected dietary program selected from a plurality of dietary programs, and wherein the target level for each of the three or more nutrients is determined based on the user-selected dietary program. Assigning the plurality of numeric weights includes assigning the numeric weight for each of the nutrients from a nutrient-specific set of numeric weights determined based on one or more goals associated with the person. The three or more nutrients include a first nutrient and a second nutrient. Providing an assessment of the person's diet includes providing a first indicator of an alignment between the amount of the first nutrient and the target level of the first nutrient, providing a second indicator of an alignment between the amount of the second nutrient and the target level of the second nutrient, and providing a nutritional index representative of an aggregate alignment between the user-selected dietary program and the person's diet based on the respective alignments of the first and second nutrients.

In some implementations, the method includes providing a recommendation for the person to consume a recommended food selected from one or more foods based on a predicted change in the nutritional index. The recommended food is selected to change the first indicator and to simultaneously reduce a negative impact on the alignment of the second nutrient. Providing the nutritional index includes calculating, for each of the three or more nutrients, a deviation for the nutrient based on the consumed amount of respective nutrient and the target level of the respective nutrient. The recommended food may be selected to simultaneously reduce the deviation for each of at least two of the three or more nutrients. The method may include selecting the recommended food based on a desired consumption distribution of the three or more nutrients over a predetermined time period. In some implementations, the recommended food is selected from one or more foods previously consumed by the person. Providing the recommendation may include providing a recommended amount of the recommended food and a recommended calendar date for the person to consume the recommended food, the recommended amount being different from a previously consumed amount of the recommended food. In other implementations, the recommended food is selected from one or more foods not previously consumed by the person.

In some implementations, the method includes generating the target level of at least one of the three or more nutrients based at least in part on an actual or estimated amount of exercise performed by the person during a predetermined time period.

In some implementations, the at least one electronic database is configured to store a set of nutrient-specific weights for each of the three or more nutrients, each nutrient-specific weight corresponding to a different time period for the nutrient, the method including selecting the plurality of numeric weights from the nutrient-specific weights based on a first predetermined time period for which the assessment is provided.

Another aspect relates to a system for aligning a person's diet with specific dietary goals. The system includes a processing system including one or more computer processors, at least one non-transitory computer readable medium storing one or more electronic databases, and one or more communications port. The processing system is configured to receive data representative of one or more meals consumed by the person, each meal including a specified portion of one or more foods and determine a target nutritional profile associated with the person, the target nutritional profile including target levels for first and second nutrients. The processing system is configured to generate a meal recommendation based on a selected meal from the one or more meals, the meal recommendation including a modified portion size for at least one of the one or more foods such that the meal recommendation simultaneously improves an alignment between nutrient levels of the first and second nutrients in the selected meal and the target nutritional profile and output via at least one of the one or more communications ports data representative of the meal recommendation.

In some implementations, the processing system is configured to receive, from a user device or from the one or more electronic databases, data representative of a user-selected dietary program selected from a plurality of dietary programs. The processing system is configured to generate the meal recommendation by selecting, for each of the one or more meals, a recommended number of servings of each of the one or more foods in the meal, the recommended number of servings selected as the modified portion size to reduce a deviation between the nutrient levels of the selected meal and the target nutritional profile. The modified portion size may be based on a desired distribution of the first and second nutrients over a predetermined period of time or within the selected meal. The desired distribution may include a per-meal constraint for each of a plurality of nutrients including the first and second nutrients.

In some implementations, the data representative of one or more meals includes data representative of a plurality of meals consumed over a predetermined period of time, each meal being associated with a calendar date. The processing system is configured to output data representative of an index representative of an alignment between the nutrient levels of the meal recommendation and the target nutritional profile. The processing system is configured to generate the index by applying to a weighted function a specific weight for each of the first and second nutrients, the specific weight being based on a comparison between an amount of each nutrient in the selected meal and the target level of the respective nutrient.

Another aspect relates to a system for aligning a person's diet with specific dietary goals. The system includes a first data port configured to receive first input data representative of a dietary program for the person and second input data representative of one or more foods consumed by the person and a second data port configured to communicate with a processing system, the processing system including a server, one or more electronic databases configured to store data representative of target levels of first and second nutrients in each of one or more dietary programs, and data representative of amounts of the first and second nutrients in each of a plurality of foods. The system includes a processor in communication with the first and second data ports. The processor is configured to output the first and second input data to the processing system over a communication network and receive, from the processing system, an index representative of an alignment between the person's diet and a dietary program identified by the server from the one or more dietary programs using the first input data, wherein the index is based on the amounts of the first and second nutrients and the target levels of the first and second nutrients in the dietary program. The processor is configured to receive, from the server, a recommendation for a food to be consumed based on the index and output the index and the recommendation to the user interface device via the first data port.

In some implementations, the first input data includes a user-specific parameter selected from the group consisting of a nutritional goal, a weight goal, an exercise goal, and a medical condition, and wherein the dietary program is identified based on the user-specific parameter. The one or more databases are configured to store information indicative of meals previously consumed by the person, each meal including a combination of foods, and wherein the processing system is configured to determine the recommendation by selecting a meal from the meals previously consumed by the person. The processor may be configured to provide data representative of a graphical nutrient profile for the person, the graphical nutrient profile including a graphical indicator for each of a plurality of nutrients in the selected dietary program, each graphical indicator indicating whether the person's consumption of the nutrient is in deficit or excess of the target levels. The index may be representative of the alignment between the person's diet and the dietary program over a predefined time period between 3 days to 10 days.

In some implementations, the processor, the first data port, and the second data port are housed in a user interface device. The user interface device may include a GPS-enabled mobile device, and wherein the first data port is configured to receive a third input data representative of one or more locations detected using the GPS over a predefined period of time. The first data port is configured to receive the second input data in response to a prompt provided to the user to identify one or more foods consumed at the one or more locations.

BRIEF DESCRIPTION OF THE DRAWINGS

The above and other features of the present disclosure, including its nature and its various advantages, will be more apparent upon consideration of the following detailed description, taken in conjunction with the accompanying drawings in which:

FIGS. 2A-2B are example data structures stored on one or more electronic database, according to an illustrative implementation.

FIG. 15 is an example display of a personal information screen for the user to select from a list of dietary programs or goals, according to an illustrative implementation.

FIG. 16 is an example screen that displays the user's target profile, according to an illustrative implementation.

FIGS. 18-20 are example screens that display how a user may create combinations of multiple foods, according to an illustrative implementation.

FIGS. 23-26 are example screens that display how a user may create a log entry to indicate that a hot chicken sandwich was consumed for lunch, according to an illustrative implementation.

FIGS. 27-29 are example screens that display how a user may create a combination of foods already logged, according to an illustrative implementation.

FIGS. 31-33 are example screens that display how a user may log exercise, according to an illustrative implementation.

FIG. 34 is an example screen that displays a new food suggestion for the user, corresponding to a food that is not in the consumed foods database for the user, according to an illustrative implementation.

FIG. 36C is an example screen that displays which foods a user has consumed that contribute to a consumed level of a nutrient, according to an illustrative implementation.

FIG. 37 is an example screen that displays a list of nutrients for which the user consumption levels are within a range close to the target profile, according to an illustrative implementation.

DETAILED DESCRIPTION

Described herein are nutrition analysis and recommendation systems and methods that provide a tailored approach to analyzing nutrient intake levels and to generating recommendations that are responsive to both a specific user's current nutritional intake and the user's nutrition-related goals. To provide an overall understanding, certain illustrative implementations will now be described, including a system for suggesting foods to help a user modulate his or her nutrient consumption to meet personalized goals. However, it will be understood by one of ordinary skill in the art that the systems and methods described herein may be adapted and modified as is appropriate for the application being addressed and may be employed in other suitable applications, and that such other additions and modifications will not depart from the scope thereof.

Figure 1A:
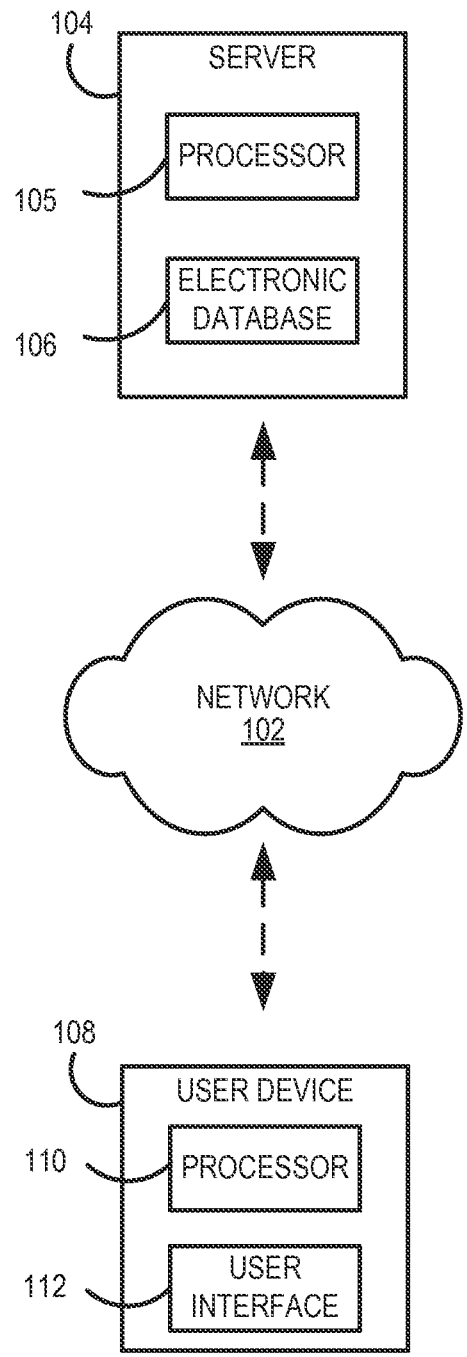
FIGS. 1A-1C are block diagrams of computerized systems for providing tailored nutrition analysis and recommendations, according to an illustrative implementation.
Figure 1B:
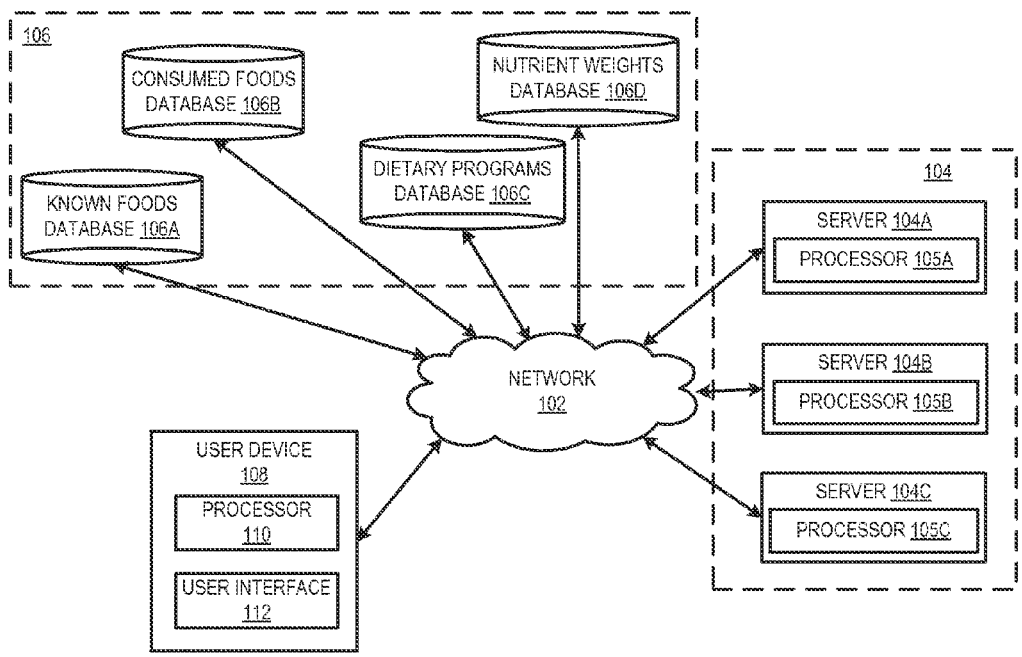
Figure 1C:
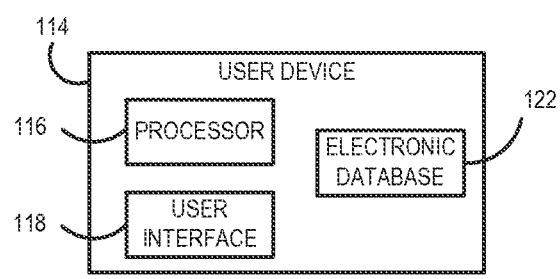

FIGS. 1A-1C depict examples of network and database structures that may be used to implement the systems and methods disclosed herein. FIG. 1A is a block diagram of a computerized system 100 for modulating a person's diet to align with the person's specific dietary goals, according to an illustrative implementation. The system 100 includes a server 104 and a user device 108 connected over a network 102 to the server 104. The server 104 includes a processor 105 and an electronic database 106, and the user device 108 includes a processor 110 and a user interface 112. As used herein, the term "processor" or "computing device" refers to one or more computers, microprocessors, logic devices, servers, or other devices configured with hardware, firmware, and software to carry out one or more of the computerized techniques described herein. Processors and processing devices may also include one or more memory devices for storing inputs, outputs, and data that is currently being processed. An illustrative computing device 1300, which may be used to implement any of the processors and servers described herein, is described in detail below with reference to FIG. 13. As used herein, "user interface" includes, without limitation, any suitable combination of one or more input devices (e.g., keypads, touch screens, trackballs, voice recognition systems, etc.) and/or one or more output devices (e.g., visual displays, speakers, tactile displays, printing devices, etc.). As used herein, "user device" includes, without limitation, any suitable combination of one or more devices configured with hardware, firmware, and software to carry out one or more of the computerized techniques described herein. Examples of user devices include, without limitation, personal computers, laptops, and mobile devices (such as smartphones, blackberries, PDAs, tablet computers, etc.). Only one server and one user device are shown in FIG. 1A to avoid complicating the drawing; the system 100 can support multiple servers and multiple user devices, as described in additional detail below with reference to FIG. 1B and throughout this disclosure.

A user provides one or more inputs, such a selected dietary program or a nutritional goal and information relating to specific foods the user has consumed (including, e.g., type of food and quantity), to the system 100 via the user interface 112. Food includes any substance consumed to provide nutritional support for the body, and typically includes nutrients that are absorbed by the body to stimulate growth, maintain life, or provide energy. Food may include substances of man-made or natural origin, and may be consumed in their naturally occurring form (e.g., an apple, an orange, a potato, beef) or in prepared or packaged forms including one or more other foods (e.g., a meal, an energy bar, or a beverage). A dietary program may codify a set of nutritional or other health-related goals, and each goal may include a set of nutrients and an acceptable target range or target value for each nutrient. A dietary program can be personalized for a user based on various factors, including, without limitation, to achieve a desired physiological outcome (e.g., lose weight, maintain weight, gain weight, more strength, prevent cancer, etc.), to conform to current medical thinking for specific demographic groups (e.g., female of child-bearing age, teenager, toddler, adult over 50, etc.), or to take into account specific constraints, such as a medical condition or dietary restriction of the user. A nutrient includes any source of nourishment, typically found in food, but may also be found in other sources or produced internally by the body. Examples of nutrients include calories; proteins or their building blocks, such as amino acids; water; carbohydrates including monosaccharides such as glucose, disaccharides such as sucrose, and oligosaccharides and polysaccharides such as starch, glycogen, and cellulose; lipids, fatty acids, and other fats; fiber; cholesterol; omega-3; vitamins and dietary or nutritional supplements; potassium; calcium; magnesium; nitrates; phosphates; iron; zinc; other elements such as copper; sodium; minerals; or any other nutrient. The processor 110 may process the data corresponding to the user inputs before transmitting the user inputs to the server 104 over the network 102. For example, the processor 110 may package the information with a timestamp or encode the information using specific pre-defined food or dietary program codes. The electronic database 106 stores the user inputs and also stores additional data including data indicative of previously consumed foods that were previously input into the user interface 112 by the user. The amount of each of the various nutrients in each food is stored in the electronic database 106. For example, a banana identified in the database would be associated with a predetermined content label identifying, for example, the calories and the grams of carbohydrate, fat, protein, starch, fiber, potassium, salt, water, and other nutrients contained, on a per-serving or per-item (e.g., per single banana) basis. An example of these nutrient levels is shown in column G of Table 1 below (see page 12).

The processor 105 is configured to determine an index based on the nutrient content of the consumed food ("the consumption profile") and target nutrient levels (the "target profile"). As used herein, the phrase "based on" means "based at least in part on". The target profile is determined according to the user's goals and/or selected dietary program. The index is representative of how much the consumption profile (determined by the nutrient levels in the consumed food) deviates from the target profile. The index may be a numeric index (such as a number between 1 and 100 or 0 and 1), an alphabetical index (such as a grade from F to A+), a color selected from a color gradient that represents the range of the index, a graphical icon that indicates progress towards the target profile, a combination of these, or any other visible or audible indicator that communicates a degree of deviation between the consumption profile and the target profile. The form of the index may also be determined based on demographic features of the user, such as age and gender. For example, a child may be more responsive to an index that takes the form of a visual icon that changes as the child's consumed nutrition approaches a target nutrient profile (e.g., an animated dog that grows more active as the index increases or gold stars that increase in size and/or number as the index increases). The processor 105 also determines and recommends, based on historic consumption levels, a food stored in the electronic database 106 that, if consumed by the user, would cause the index to increase, indicating that user's consumption profile would better match the user's target profile.

The components of the system 100 of FIG. 1A may be arranged, distributed, and combined in any of a number of ways. For example, FIG. 1B is a block diagram of a computerized system 120 that distributes the components of system 100 over multiple processing and storage devices connected via the network 102. Such an implementation may be appropriate for distributed computing over multiple communication systems including wireless and wired communication systems that share access to a common network resource. In some implementations, system 120 is implemented in a cloud computing environment in which one or more of the components are provided by different processing and storage services connected via the Internet or other communications system. Like the system 100 of FIG. 1A, the system 120 includes the user device 108, the electronic database 106 and the server 104. The user device 108 includes a processor 110 and a user interface 112. The server 104 is a distributed system of servers that includes server instances 104A, 104B and 104C, each including processor instances 105A, 105B and 105C, respectively. The server instances 104A, 104B and 104C may be, for example, virtual servers instantiated in a cloud computing environment.

The database 106 is a distributed system of databases that includes a "known foods" database 106A and a "consumed foods" database 106B, or may be combined into a common database. The known foods database 106A is a dictionary of foods known to system 120 and may include, for each food item contained in the database, name variants for the food, nutritional content of the food (e.g., on a per-serving or per-unit-mass basis), and tags describing other characteristics of the food (e.g., vegetarian, whole grain, meat, kosher, nut). The known foods database 106A may be populated by any suitable means, including by manual updates or by importing from other foods databases such as the USDA National Nutrient Database and other similar sources of food information. The known foods database 106A preferably includes a vast majority of foods known to humans, but need not contain every possible known food. While the known foods database 106A is preferably to be universal, the consumed foods database 106B may be limited to storing only foods previously indicated as being consumed by at least one user of the system 120. Although the consumed foods database 106B may be stored in a database that is part of a distributed architecture, in some implementations the consumed foods database may be stored locally on the user device 108 or on a server. Where the consumed foods database 106B is stored locally, the database may be limited to storing data regarding foods consumed by one or more users associated with the user device. The average person typically consumes approximately 200 foods out of the about 23,000 foods. Thus, the known foods database 106A may contain the set of all 23,000 foods, while the consumed foods database 106B may contain just the 200 foods that the user consumes and is substantially easier to parse than the known foods database 106A. Since a majority of the database searches performed will involve searching for items among consumed foods, and can begin with this smaller set of foods. Thus, storing the foods that the user consumes separately makes parsing the foods database much more efficient when, for example, determining an appropriate food for recommendation.

In addition, the foods in either database may be tagged with certain data specific to the foods and pertaining to certain characteristics of the food. For example, the tags may indicate that a food contains a certain ingredient, such as peanuts. In this case, a user who is allergic to peanuts may wish to view only recommendations of foods that do not contain peanuts. By labeling the foods in a database with tags including such information, the processor 105 can efficiently parse through the set of foods in the database by limiting a set of candidate foods for recommendation based on the tagged data. In general, the foods may be tagged with any special data or preferences associated with one or more users, including whether the food contains an ingredient that is a common (or generally known) allergen, whether the food has glycemic characteristics or medicinal properties, or whether the food is consistent with a special diet such as vegetarian, kosher, vegan, or any other suitable diet. By labeling foods with such data and filtering the foods with a set of preferences provided by a user, appropriate food recommendations may be efficiently provided to the user.

The components of the system 120 are connected over a communications network 102. The arrangement and numbers of components shown in FIG. 1B are merely illustrative, and any suitable configuration may be used. Database 106 further includes dietary programs database 106C, which stores various levels of nutrients (both relative amounts and absolute amounts for different dietary programs (e.g., the Atkins diet, vegetarian diet, ketogenic diet). Database 106 also includes nutrient weights database 106D, which stores weights applied to each nutrient in the target profile. Although the nutrient weights may be stored locally in the user device 108, in preferred implementations, the nutrient weights are stored in a database that is part of system that employs a distributed architecture. The improved availability associated with using such architecture for the nutrient weights advantageously facilitates continuous refinement of the nutrient weights to account for current dietary or medical thinking, and also facilitates inputs from various physicians or dieticians.

Although FIGS. 1A and 1B depict network-based systems for modulating a person's diet to align with the person's specific dietary needs, the functional components of the system 100 or the system 120 may be implemented as one or more components included with or local to the user device 108. For example, FIG. 1C depicts a user device 114 that includes a processor 116, a user interface 118, and an electronic database 122. The processor 116 may be configured to perform any or all of the functions of processors 105 and 110 of FIGS. 1A and 1B, the electronic database 122 may be configured to store any or all of the data stored in database 106 of FIGS. 1A and 1B, and the user interface 118 may be configured to perform any of the input and output functions described herein for the user interface 112 of FIGS. 1A and 1B. Additionally, the functions performed by each of the components in the systems of FIGS. 1A-1C may be rearranged. In some implementations, the processor 110 (FIG. 1A) may perform some or all of the functions of the processor 105 as described herein. For example, the processor 110 may compute the index, and/or may determine an appropriate food in a database of foods to recommend to the user. For ease of discussion, the remainder of this disclosure will often describe index determination and food recommendation techniques with reference to the system 100 of FIG. 1A. However, any of the systems of FIGS. 1A-1C may be used, as well as any suitable variations of these systems.

FIGS. 2A and 2B depict examples of data storage structures that may be used in database 106 (FIG. 1A) to store records of the foods that a user has consumed. FIG. 2A depicts a first data structure 132 for records in a consumed food database (such as consumed food database 106B of FIG. 1B), which corresponds to a list of foods consumed by one or more users. In this example, the data structure 132 includes three records of consumed foods, and for ease of illustration, the records for only a single user are shown. Each record in the data structure 132 includes a "food consumed" field whose values include identification numbers for foods listed in a known foods database, such as the known foods database 106A of FIG. 1B. Each record in the data structure 132 also includes a field for the number of servings of the consumed food, one or more meal type classifications (e.g., breakfast, brunch, lunch, dinner, or snack), a date the food was consumed, and a barcode identifier (if applicable). The barcode identifier field may be stored in a data structure such as the data structure 132 for enabling an efficient parsing of a database to locate one or more database entries corresponding to foods that a user has consumed. For example, the user device 108 may be equipped with barcode scanning capabilities, such that that barcode scanning may be used to log consumed food entries. The data structure 132 may also be sorted according to the barcode identifiers, which would further increase the efficiency of parsing the database and logging foods.

In some implementations, for a food that the user consumes more than once, the same record in the data structure 132 may include multiple values in the fields for the dates that the user consumed the food, which meal type classification was selected when the user consumed the food, the number of servings that was consumed, or any other suitable field. In some implementations, the data structure 132 stores or tracks foods that the user has consumed during a fixed time period, such as during the most recent week, month, two months, or any other suitable time period. In this case, the data structure 132 may simply store a count of how many times the food was consumed (or a total amount that the food was consumed) during the time period and/or the most recent date on which the user consumed the food. In some implementations, when the user consumes the same food multiple times, a new record in the data structure 132 may be created each time the user consumes the food. Other fields, such as a user ID field or a food rating field, may also be included.

FIG. 2B depicts a second data structure 134 for records in a consumed food database (such as consumed foods database 106B of FIG. 1B), but instead of being organized according to separate records of consumed foods, the data structure 134 is organized by meals consumed by one or more users. As used herein, the term "meal" refers to one or more foods that are consumed at a designated time of day (e.g., breakfast in the morning, lunch at mid-day, and dinner in the evening) or groups of one or more foods that are consumed within the same sitting (which may or may not correspond to a particular time of day). Because people typically consume certain foods in certain combinations at certain times of day, using information about which foods are eaten together at different times may improve the food recommendations provided by the system 100 (as described in detail below). For example, using this approach, a user who consumes most of his or her caloric allowance during breakfast is likely to receive meal recommendations that include a larger proportion of the user's caloric intake allowance in a breakfast recommendation. Data structure 134 includes two records of meals, each of which has a meal label field (which includes the date and a meal type) and a list of the foods consumed at that meal (by identification number). For example, the first record 136 corresponds to the foods that were consumed for dinner on Oct. 11, 2010, and the second record 138 corresponds to the foods that were consumed as a snack on the same date. The data structures 132 and 134 are different ways of representing the same consumed food data, with different instantiations used for different purposes within the system 100. In some implementations, the user device 108 may store the consumed food database locally (e.g., in electronic database 122 of FIG. 1C), or the consumed food electronic database may be stored on the server 104 (e.g., in electronic database 106 of FIG. 1A) or in a separate database accessible to the server 104 (e.g., as shown in FIG. 1B).

Figure 3:
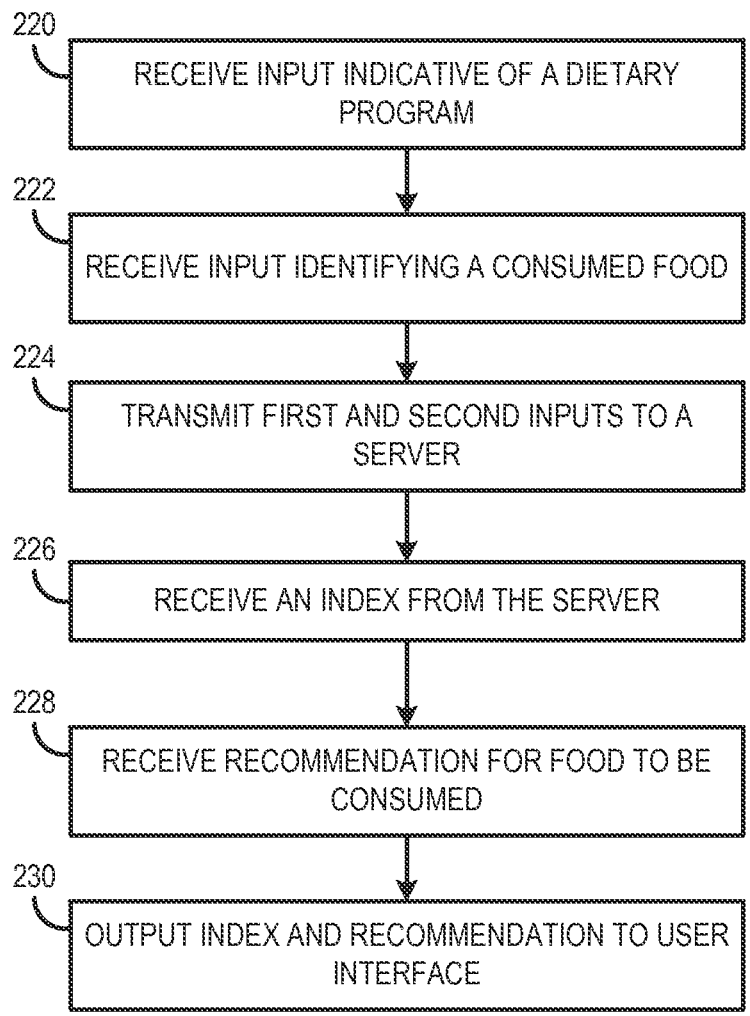
FIG. 3 is a flowchart of a method used by a computerized system to align a person's nutritional diet with the person's nutritional goals, according to an illustrative implementation.

FIG. 3 is a flowchart of a method 200 that may be implemented by the system 100 to modulate a person's diet with specific dietary needs. In general, the method 200 provides an analysis of the nutritional content of the food consumed by the user in comparison to nutrient levels recommended for or specified by the user, according to the user's health-related goals. An overview of the method 200 will first be provided, followed by illustrations of various implementations of the steps of the method. As shown, the method 200 generally includes the steps of receiving an input indicative of a dietary program and an input identifying a consumed food. The dietary program may be selected by the user from a plurality of dietary programs, or by the system from the plurality of dietary programs based on user-specific information (such as a medical condition, a nutritional goal, an exercise, etc.). In certain implementations, the inputs are received at the user interface 112, with the first input indicating a dietary program selected from a menu (step 220) and the second input identifying a consumed food (step 222). The method further includes transmitting one or both inputs to the server 104 (step 224) and, in response, receiving an index from the server 104 (step 226). The index is calculated by determining the nutritional content of the consumed food and identifying a deviation between the nutrient levels in the consumed food and target nutrient levels. The processor 110 also receives from the server 104 a recommendation for a food to be consumed (step 228), and then outputs the index and the recommendation to the user interface 112 (step 230). The steps of the method 200 may be performed in any suitable order. For example, some steps of the method 200 may be performed simultaneously, in reverse order, or some steps may be omitted. For example, the step of receiving an index from the server (step 226) may be omitted such that at step 230, the method 200 outputs a recommendation without an index. Similarly, the step of receiving a recommendation (228) may be omitted so that at step 230, the method 200 outputs an index. Although the index is generally described below in numeric terms for ease of illustration, it is understood that the index may one or more indicators of any suitable form capable of providing an assessment of the consumed nutrients with respect to the user's dietary needs.

Various implementations of the methods and systems for the nutritional analysis and recommendation are now described. For ease of illustration, and not by way of limitation, the implementations may be described by reference to FIG. 3. It is understood however, that the systems and method implementations may be implemented alone or in combinations not limited to the method 200. Prior to selecting a dietary program (e.g., at step 220 of FIG. 3), a user may authenticate with the server 104. The user may authenticate with the server 104 using any suitable known authentication mechanism. For example, the user may input a username and password (or may provide other identification information) via user interface 112, and proceed to step 220 (or step 222) by selecting a "My Profile" option, as shown in the example display of FIG. 14. When step 220 is used, the processor 110 receives a first input from user interface 112 indicative of a selected dietary program. FIG. 15 is an example display that may be provided by the user interface 112 to prompt a user to input a dietary program or specific health-related goals. At step 220, the user interface 112 may provide a menu or list of dietary programs and health-related goals, and the user may select a dietary program or goal from the menu or list. The dietary program may be selected from one or more predetermined programs or may be selected by receiving user inputs of desired levels of one or more nutrients, or based on particular desired health outcomes. In some embodiments, step 220 may be omitted; instead, the dietary program is preselected, for example, by the user or by the user's physician, nutritionist or trainer. Dietary programs may codify health-related goals, such as managing specific medical or dietary conditions, meeting nutrient needs, trying new foods, eating more fruits and vegetables, or a specific diet, such as adhering to low carbohydrate diets (e.g., South Beach, Atkins) or to U.S.D.A. guidelines, diets targeted toward a person of the weight, age, gender, and health of the user, or any other nutritional program targeted to improve or maintain a user's overall health. Dietary programs on the menu may also include other types of health-related goals such as maintaining weight, losing weight, gaining weight, feeling more energetic, managing stress, sleeping better, increasing physical strength or flexibility, trying new fitness activities, exercising more frequently, training for an athletic event, or any other type of physiological goal that a user wishes to achieve.

In addition to selecting from the menu of dietary programs, the user can also provide other health-related goals, constraints or comments to the user interface 112. For example, the user may input in a free-form answer field certain food allergies, constraints, or preferences (e.g., if the user maintains a vegetarian, vegan, or kosher diet, or has any other type of dietary constraint). The user may also input in the free-form answer field specific medical conditions, such as if user has diabetes, high blood pressure, high cholesterol, or any other specific medical condition that may affect the way the user eats or exercises. Information entered in the free-form answer field may be parsed by an automatic text recognition system to match the user's information to a particular dietary program, or may be forwarded to a clinician for review and possibly additional consultation with the user. In addition, the user may input demographic features, such as date of birth, gender, height, current weight, desired weight, activity level, or any other demographic feature that may capture some aspect of health-related goals.

In step 222, the processor 110 receives the input from the user interface 112 indicative of one or more consumed foods, which will be analyzed for their nutritional content, or described below. FIGS. 23-26 are example displays of the user interface 112 by which the user inputs a consumed food to the system 100. In some implementations, the user interface 112 may display a zooming or zoomable user interface (ZUI), which may be a graphical display that allows the user to change the scale of view on a set of images of food products. The food products that are displayed on the ZUI may be selected differently for different users. In particular, the food products on the ZUI may be selected based on whether a user has previously consumed the food product or a frequency that the user consumes the food product. A ZUI is generally suitable for displaying at any one time a small subset of a large set of items. Here, a ZUI may be suitable because while the universe of known foods runs on the order of several tens of thousands, the average person typically consumes only a few hundred foods (e.g., approximately 200 foods) out of this large set. Even so, the system might only display a small subset of these consumed foods at any one time based on the specific user request, making the use of a ZUI possible or practical. The food products displayed on the ZUI may be organized according to a classification of a meal type, such as breakfast, brunch, lunch, dinner, and snack. In addition, one or more tiers of food products may be used to further organize the display. The tiers may be sorted according to a type of food product, such as by fruits, vegetables, meats, dairy, beverages, or any other suitable type of food product. In an initial display, the ZUI may include a simple listing of one or more tiers at the highest level (by meal of type of food product, for example). Then, the user may expand one or more of the tiers to reveal lower levels (the names or pictures of the specific food products, for example). Thus, the user may use the ZUI to select one or more foods to indicate that the user has consumed or plans to consume the selected foods. This input is used to create a user log entry corresponding to the consumed food. The consumed foods are foods that the user has consumed in the past, or expects to consume. The foods may be part of a meal consumed by the user in the same sitting (e.g., a sandwich and salad for lunch or may be from different meals or sittings). The user also indicates on the user interface 112 the portion size of the consumed food, the day the food was consumed, and the meal in which the food was consumed (such as by indicating whether the food was consumed at breakfast, lunch, dinner, or as a snack).

In step 224, the processor 110 transmits the first and second inputs to the server 104 over the network 102. The processor 110 then receives (from the server 104 over the network 102) an index calculated based on the nutritional content of the consumed food (step 226) and the selected dietary program. The index is preferably a single marker that represents, in a cumulative fashion, how far the user's consumption profile deviates from the target profile (e.g., from U.S.D.A. diet guidelines). In the examples below, the deviation for each nutrient is calculated as a difference between the target level and the consumed amount for the nutrient. However, as noted above, any of several approaches for determining a deviation may be used. A deviation between a target (such a desired level of a nutrient) and an attained amount (such as a consumed amount of the nutrient) provides an indication of an alignment between a goal (as may be defined by one or more targets) and an attainment (as may be defined by consumed amounts of one or more nutrients). Deviation can include a comparison between a specific target (which may or may not include a range) to a specific amount or level. A deviation can be determined for a specific component of the goal (e.g., a single nutrient) or for multiple components (e.g., multiple nutrients compared on a nutrient-by-nutrient basis). Example suitable ways to determine a deviation include subtracting one value from another value to obtain a difference, computing a ratio between two values, any number of statistical approaches such as a standard deviation or statistical variance, pattern comparison and recognition, correlation approaches such as by comparing a curve or graph of one set of values to a corresponding curve or graph or another set of values, comparisons based on derived properties of the data sets, such as by regression-based or line-fitting approaches, or error estimation methods such as root-mean-squared. When multiple values of targets or attained levels are used, the data set may correspond to various nutrients, time periods, individuals, groups of people, or any other suitable parameter. A profile of deviations may be obtained, such that the deviation profile is based on a comparison between a target nutritional profile for a person and a nutrient consumption profile for the person. The deviation profile may include, for each nutrient in the target nutritional profile and/or the nutrient consumption profile, an indication of whether the nutrient is in excess or deficit. An alignment can be determined based on one or more deviations to provide an indication of compliance between the goal and an overall attainment as both relate to the activity being assessed.

The systems and methods disclosed herein may be provided for one nutrient or for multiple nutrients. However, the systems and methods are particularly advantageous when applied to multiple nutrients (e.g., to three or more nutrients) to simultaneously assess nutritional intake for one or more persons. As noted above, assessing nutrition or recommending foods when multiple nutrients are at stake can be a particularly challenging computational problem. This difficulty is due in part to the staggering number of available foods (currently estimated as a few tens of thousands), the variability in nutritional value of these foods (both in terms or amount and types of nutrients), varying portion sizes for the same food, and user-specific factors that must be considered in order to provide useful assessments and recommendations. In preferred implementations, a deviation from the user's target nutrition level is calculated for each of a plurality of nutrients contained within the consumed food to derive a deviation profile. The deviation profile may be summed or further processed to provide the overall deviation index. A target nutrition level for a nutrient is an amount or range of amounts of the specific nutrient that a user desires to consume within a specified time period. The specified time period may be different for different nutrients. The specified time period may include any suitable time period, including a portion of a day, a day, a 5-day period, a 7-day period, etc. For example, the target nutrition level for vitamin A is typically, though not necessarily, expressed as a weekly goal since a user is able to make up (to positive effect) deficiencies in vitamin A from one day, by consuming an excess of vitamin A on another data within 7 days of the day with the deficiency. In contrast, other nutrients, such as proteins, fats, and carbohydrates, are generally required to meet a user's daily caloric intake requirements, and are typically, though not necessarily, expressed as daily goals. Illustrative implementations of methods for determining the index are described in detail in relation to FIGS. 4 and 9. The processor 110 also receives (from the server 104 over the network 102) a recommendation for a food to be consumed (step 228), based on the index. Methods for determining the recommendation for a consumed food are described in detail in relation to FIGS. 5A-5C, 8, and 10. In step 230, the processor 110 outputs the index and the recommendation to the user interface 112 for display to the user.

Figure 4:
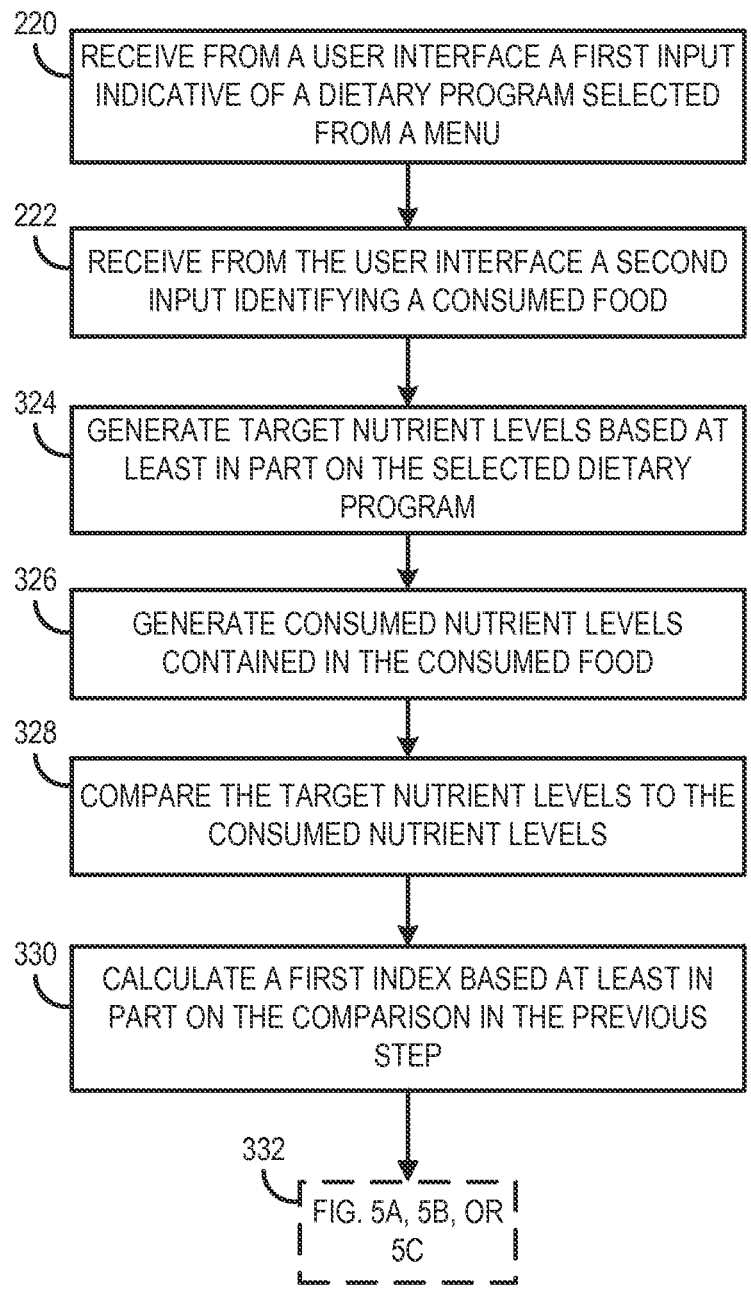
FIG. 4 is a flowchart of a method used by a computerized system to provide an assessment of a person's diet, according to an illustrative implementation.

FIG. 4 is a flowchart of a method 210 used by the processor 105 to determine a user's deviation index and use that index to suggest a food to improve the alignment between a user's consumption profile and the user's target profile, according to an illustrative implementation. In general, the method includes the steps of receiving from the user interface 112 a first, optional, input indicative of a dietary program selected from the menu (step 220) and a second input identifying a consumed food (step 222), then generating target nutrient levels based at least in part on the selected dietary program (or using pre-programmed levels, if desired) (step 324), and generating consumed nutrient levels contained in the consumed food (step 326). The processor 105 then compares the target nutrient levels to the consumed nutrient levels (step 328) and calculates a first index based at least in part on the comparison in step 328 (step 330).

As in FIG. 3, in steps 220 and 222 the processor 110 receives the user inputs from the user interface 112 and forwards the user inputs to the server 104. In step 324, the processor 105 generates the target nutritional profile corresponding to target nutrient levels. The target profile is specific to the user, is based on a dietary program (which may be pre-configured or selected by the user), and may be dependent on the user's health and demographic features. In most instances, the target profile will correspond to the user's dietary program (determined, for example, to achieve a user's health-related goal) or to a predetermined target.

When the user selects from a set of health-related goals (such as those shown in FIG. 15), a user-specific dietary program is automatically generated based on the user's selected health-related goals and demographic features. The user's dietary program corresponds to a target profile including target amounts (which may be fixed amounts or ranges) of various nutrients. The user may adjust these target amounts of nutrients depending on the user's nutritional needs, medical conditions, specific demographic features, or dietary restrictions. In addition, a second user such as a clinician, nutritionist, analyst, or any trained individual may have access to view the original user's inputs and may adjust the target amounts in the user's target profile. For example, the second user may adjust the user's target profile on a nutrient-by-nutrient basis. The second user may also adjust or select an appropriate target profile based on information in the original user's profile including the original user's selected dietary program and the user's demographic features. The second user may match the data in the original user's profile with a dietary profile or may contact the original user to set up a consultation. Furthermore, the second user may use the user's inputs and/or target profile to track clinical or other changes in the user's health or nutritional profile.

The target is determined for each nutrient in a set of target nutrients. The target profile includes target nutrient levels, which are target amounts of nutrients to be consumed over a time period (e.g., over a day, a week, a month, or any other suitable time period). Nutrient levels may include an amount of the nutrient in a mass metric (e.g., grams), volume, percentage, calories, or any other suitable metric representing an amount of a nutrient. Furthermore, as discussed above, different target nutrient levels may be based on different time periods. For example, a target amount of calories may be 1500 calories per day, while a target amount of omega-3 may be 7 grams a week. FIG. 16 is an example display of a target profile for a user, based on the selected dietary programs and demographic features shown in FIG. 15. As shown, the profile includes a plurality of nutrients with a daily numeric consumption target for each of the nutrients. Another example of a target profile is shown in column B of Table 1 below.

Figure 18:
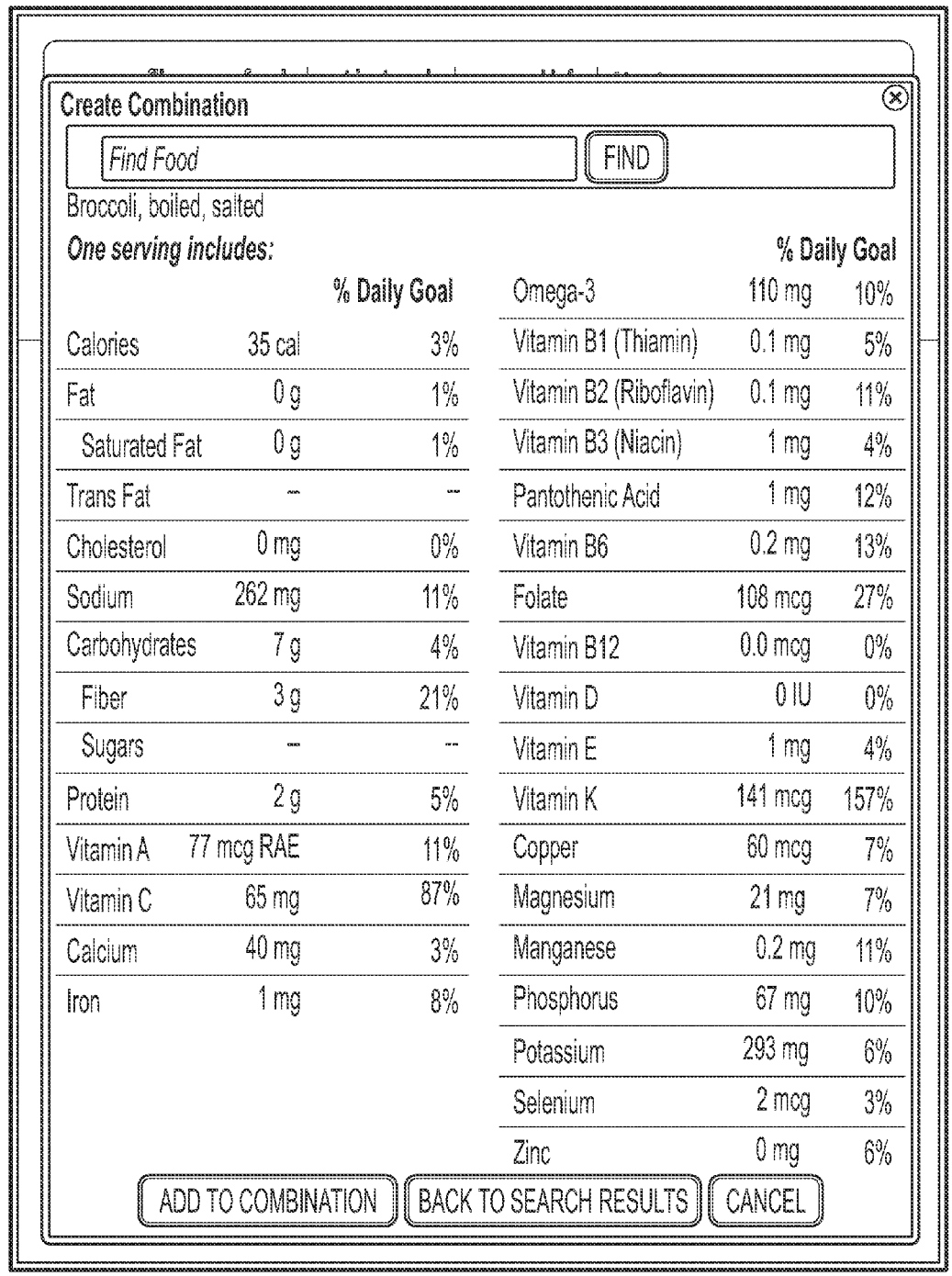
Figure 42:
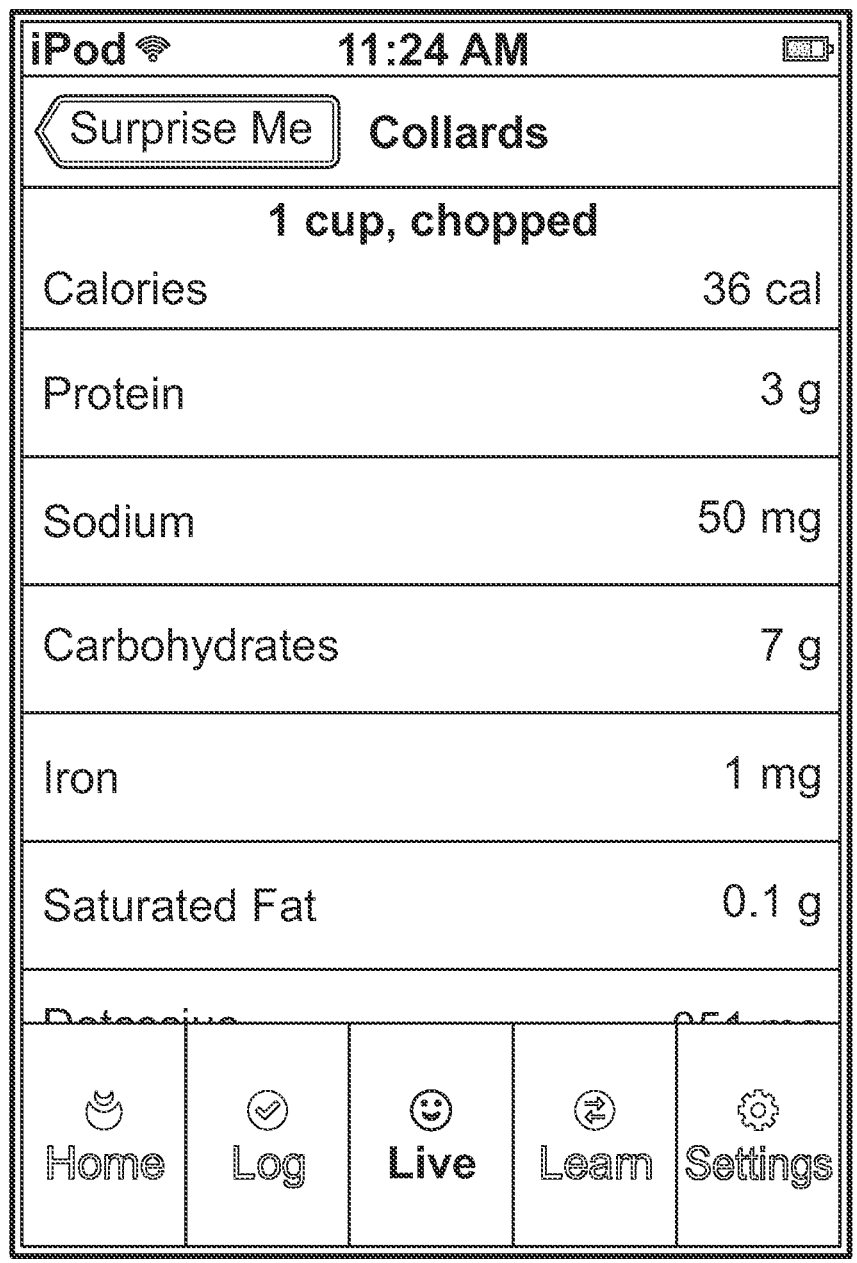
Figure 43:
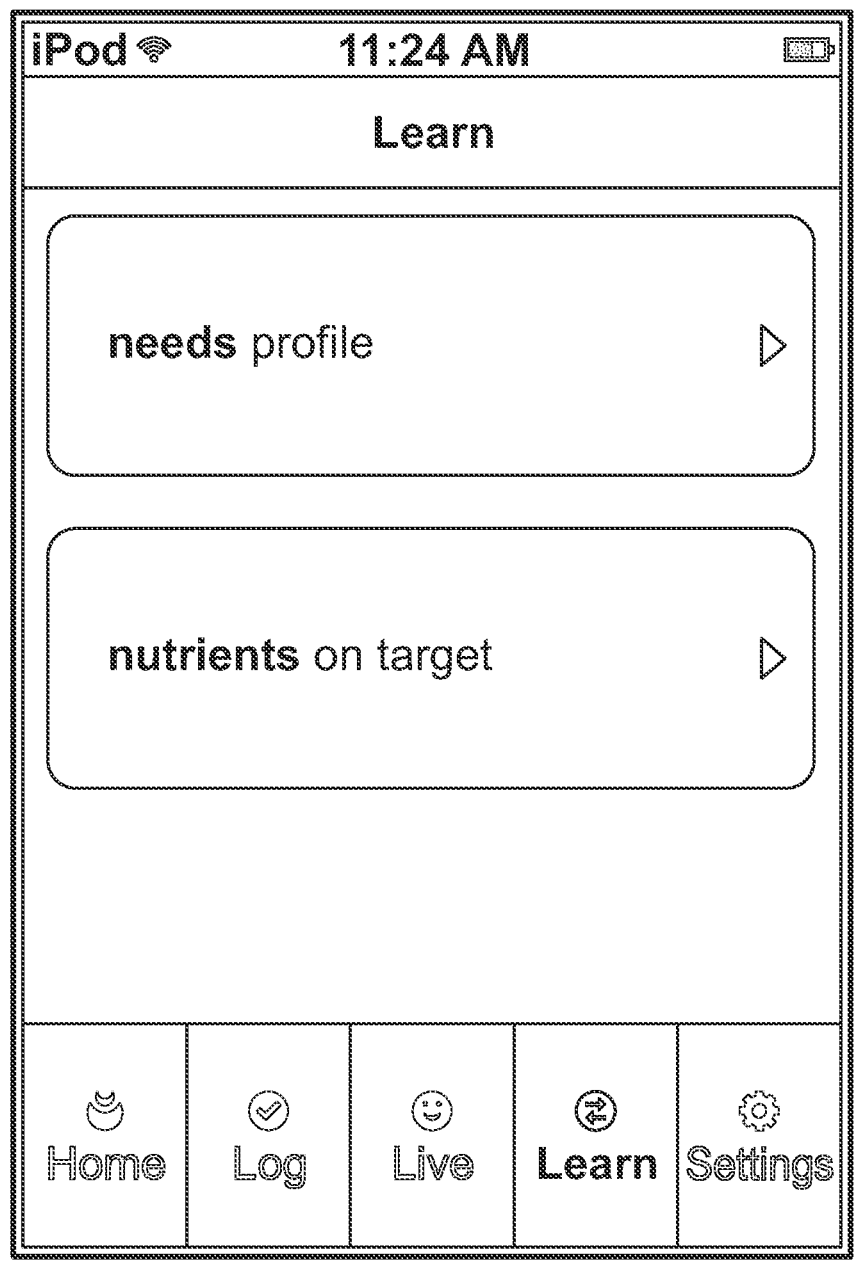
FIGS. 43-46 are example screens that display a list of deficient nutrients and a list of on target nutrients associated with a user, according to an illustrative implementation.
Figure 44:
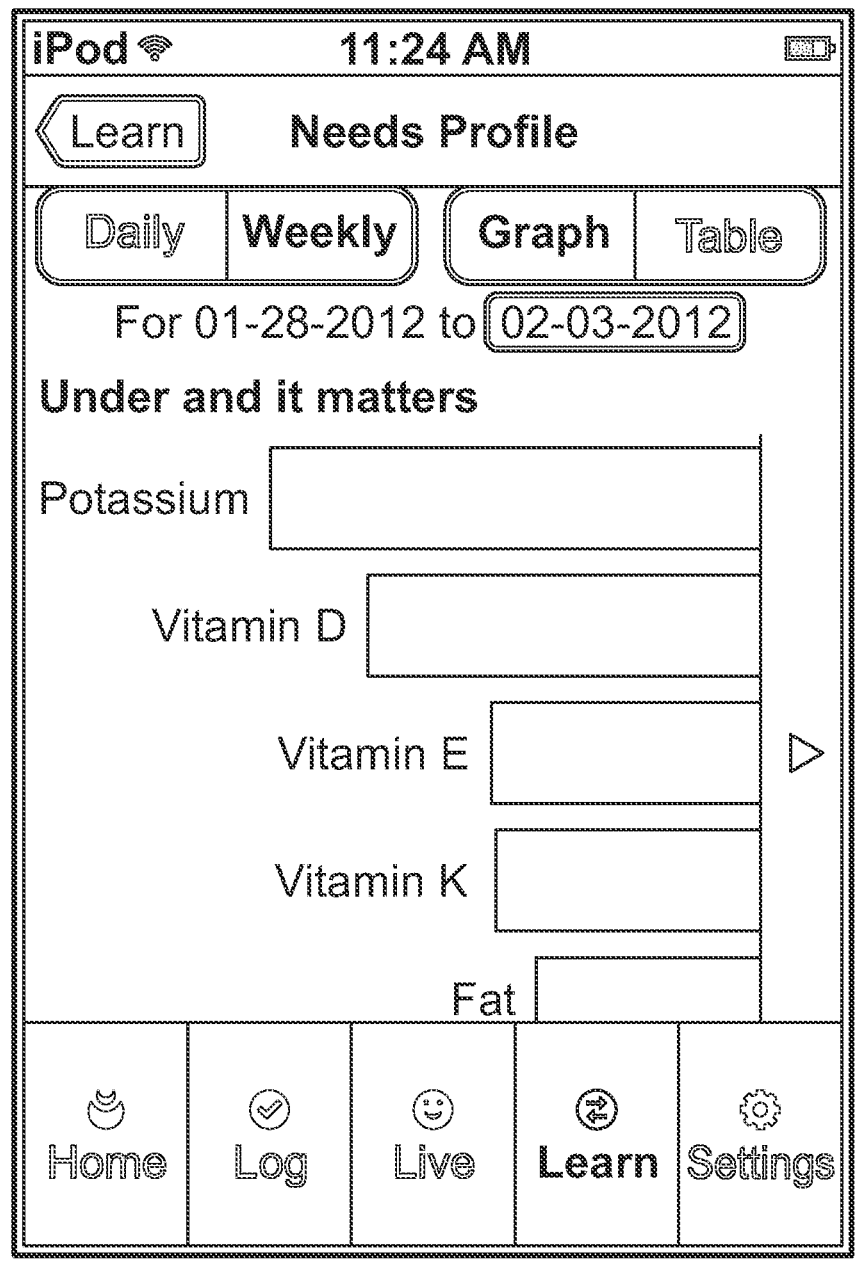
Figure 45:
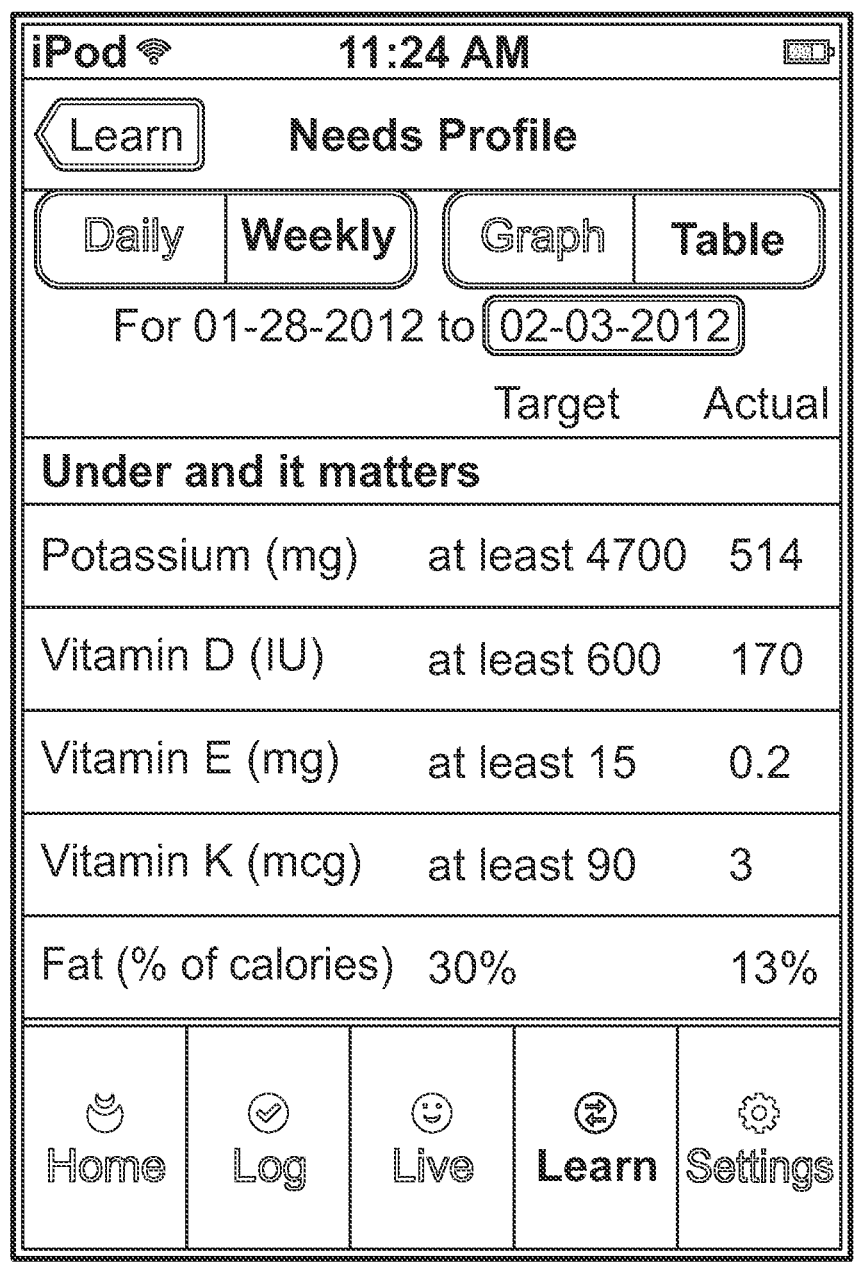
Figure 46:
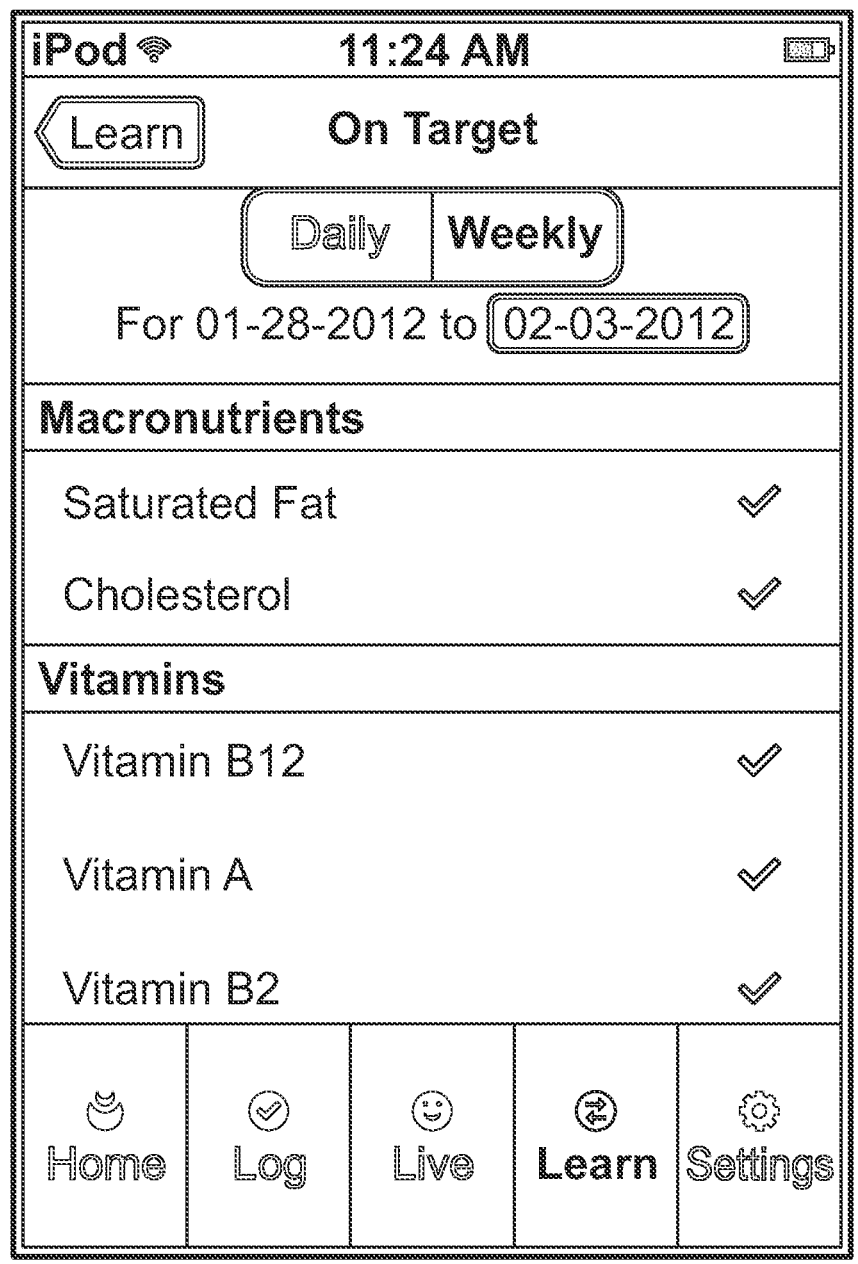

In step 326, the processor 105 generates a consumption profile corresponding to consumed nutrient levels contained in the consumed food. The consumption profile includes the nutritional content of the consumed food on a nutrient-by-nutrient basis. For each nutrient in a set of nutrients, the consumption profile includes a consumed nutrient level, which corresponds to the quantity of the nutrient in the consumed food. Examples of consumption profiles for particular foods are shown in FIGS. 18 and 42 and would include the same nutrients as those in the user's target profile. In certain implementations, the consumption profile corresponds to all foods the user has indicated as being consumed in the last day, week, month, or any other selected time period. Another example of a consumption profile is shown in column A of Table 1 below.

In step 328, the processor 105 compares the consumed nutrient levels to the respective target levels on a nutrient-by-nutrient basis. In certain embodiments, for each nutrient in the set of nutrients, the numeric indicator of the quantity of each consumed nutrient is compared to the corresponding target level. In step 330, the processor 105 then computes a first index representative of an overall resemblance between the user's target profile and consumption profile. For example, the first index may be computed in accordance with the following set of three equations:

$$IC_n = w_n * \frac{\|c_n - g_n\|}{g_n} \tag{1}$$

$$IR = 1 - \frac{\sum_{n=1}^{N} IC_n}{\sum_{n=1}^{N} w_n} \tag{2}$$

$$I = \max(0, IR) \tag{3}$$

where
$IC_n$ is the index contribution of each nutrient n;
$w_n$ is a weight function applied to nutrient n;
$g_n$ is the target nutrient component level for nutrient n;
$c_n$ is a consumed nutrient component level for nutrient n.

N is the number of nutrients in the set of nutrients;
IR is the raw index; and
I is the index.

Thus, in this implementation, the index I corresponds to a number between zero and one. The closer the index is to "one" the closer the consumed food nutrient levels are to the user's target profile. Alternatively, an index near zero means that the consumed food has nutrient levels far from the target profile. Any suitable range (including a non-numeric range or a different numeric range) can be used, and the index I can take any form or value permitted by the range. The index is representative of an aggregate alignment between a dietary program determined for the user and the user's diet based on the respective alignments of a set of multiple nutrients. The equations described herein are merely illustrative, and it will be understood that any suitable equation or function may be used (in combination with or in place of the equations described herein) for determining a value associated with an overall resemblance between the user's target profile and consumption profile.

For a particular nutrient n, $w_n$ is a weight function (or simply, weight) applied to the deviation between the consumed amount $c_n$ and the target nutrient level $g_n$. As described above, the target nutrient goal for a nutrient may be expressed as a range of acceptable levels, rather than a single target nutrient value. The target nutrient goal may also be expressed as a function of the amount or range of amount consumed of another nutrient (e.g., the daily target nutrient level for fiber is typically expressed in terms of the daily caloric intake of an individual). Thus, references to target nutrition or nutrient level in this specification are understood to encompass targets expressed as fixed values, as ranges, or as functions of the intake or goals of other nutrients. Different nutrients may have different applied weights, depending on the selected dietary program. For example, a user with kidney disease may be very sensitive to sodium, and thus any sodium consumption above a goal amount may be weighted much more heavily (to negative effect on the index) than consumption of another, less sensitive nutrient. Thus, for the same nutrient n, the weight associated with a nutrient for one user may be different from the weight associated with that nutrient for another user. The weight function for a particular nutrient may be a constant value for all deviations from the target nutrition level, a piecewise-function that varies with the degree of deviation, a piecewise non-linear function, or a continuous linear or non-linear function. Examples of weight functions that may be used are provided in FIG. 2C (and described below).

In addition, for a nutrient n, $w_n$ may depend on whether $c_n$ exceeds or does not exceed $g_n$. For example, based on the selected dietary program, it may be appropriate for a consumed nutrient level to exceed the corresponding target level for a first nutrient, but not appropriate for the target level to exceed the consumed level. Thus, for the first nutrient, if the consumed level exceeds the target level, a low weight $w_n$ would apply. Alternatively, if the target level exceeds the consumed level, a high weight $w_n$ would apply. For a second nutrient, the inverse may be true; it may be appropriate for the target level to exceed the consumed level, but not vice versa. Thus, selecting $w_n$ based on whether $c_n$ exceeds $g_n$ accounts for these possibilities. In some implementations, each nutrient n may be associated with two weights: an above-target weight $a_n$ and a below-target weight $b_n$. The above-target weight $a_n$ will be used when $c_n$ exceeds $g_n$, and the below-target weight $b_n$ will be used when $c_n$ is less than $g_n$. That is, $$w_n = \begin{cases} a_n & \text{if } c_n > g_n \\ b_n & \text{if } c_n < g_n \end{cases} \quad (4)$$

In some implementations, the processor 105 is programmed to adjust the user's index so as to reward the user for having a consumed nutrient level $c_n$ at or substantially near the target nutrient level $g_n$ for a nutrient n. One way the user may be rewarded for reaching a target level is by choosing the active weight $w_n$ to be the larger of the corresponding above-weight $a_n$ and below-weight $b_n$. That is, $$w_n = \max(a_n, b_n) \text{ if } c_n \approx g_n \quad (5)$$

Thus, for the case when $c_n = g_n$, the corresponding $IC_n$ (from Eq. 1) is zero and adds nothing to the numerator of Eq. 2. However, choosing a larger active weight $w_n$ causes the denominator of Eq. 2 to increase, thereby resulting in a larger raw index value, and accordingly, a larger index value. Thus, the user is rewarded for meeting the goal with a higher index value by choosing a larger active weight for a particular nutrient that is at or near target level. The processor 105 may also be programmed to choose a different weight for when $c_n$ is about equal to $g_n$, by using a different weight function, a weight function that is a function of $a_n$, $b_n$, and the precise value of the consumed nutrient. Furthermore, in the foregoing example, $a_n$ and $b_n$ may each be a constant value, or a function of the degree of deviation. The foregoing example assumes, for ease of description, that the target level for the nutrient n is a fixed value. However, the same principles apply in the case of a nutrient with target level expressed as range, or as a function of another consumed or target nutrient. For example, in such cases, a consumed amount exceeds the target level if the consumed amount is above the upper limit of the target range. The nutrient is less than the target level if the consumed amount is below the lower limit of the range, and the nutrient is about equal to the target level if the consumed amount is between the upper and lower limits of the target range.

As an example, Table 1 shows example consumed amounts $c_n$ of various nutrients for a user in a day (column A), corresponding to foods that the user has logged for a day. Example personal target daily levels $g_n$, weights $a_n$ and $b_n$, active weights $w_n$, and index contribution $IC_n$ are also shown in Table 1. Note that the consumed amount of fat is equal to the personal target level for fat, so the active weight is chosen to be the larger between $a_n$ and $b_n$. The difference between each consumed nutrient level and the respective target level is computed to obtain an index contribution $IC_n$ (column F of Table 1). Assuming the thirteen nutrients shown in Table 1 are all N nutrients, the corresponding index using Eq. 1-3 is 0.81. However, other nutrients may also be considered and assigned appropriate target levels and weights. Examples of other nutrients include other types of vitamins, minerals, etc., and may also even include other factors that affect a person's overall health such as water or exercise.

TABLE 1

|  | A. Consumed amount so far $c_n$ | B. Personal target $g_n$ | C. Above weight $a_n$ | D. Below weight $b_n$ | E. Active weight $w_n$ | F. Index Contribution $IC_n$ | G. Amount in a medium banana | H. Consumed amount if banana is eaten | I. 2nd Active weight $w_n$ | J. 2nd Index contribution $IC_n$ |
|---|---|---|---|---|---|---|---|---|---|---|
| Calories | 1350 | 1200 | 6 | 6 | 6 | 0.75 | 105 | 1455 | 6 | 1.28 |
| Fat | 40 g | 40 g | 10 | 5 | 10 | 0 | 0 g | 40 g | 10 | 0 |
| Cholesterol | 320 mg | <300 mg | 12 | 5 | 12 | 0.8 | 0 mg | 320 mg | 12 | 0.8 |
| Sodium | 1900 mg | <2300 mg | 10 | 3 | 3 | 0 | 1 mg | 1901 mg | 3 | 0 |
| Carbohydrates | 124 g | 165 g | 5 | 6 | 6 | 1.49 | 27 g | 151 g | 6 | 0.51 |
| Fiber | 10 g | 16 g | 2 | 11 | 11 | 4.13 | 3 g | 13 g | 11 | 2.06 |
| Protein | 24 g | 45 g | 3 | 8 | 8 | 3.73 | 1 g | 25 g | 8 | 3.56 |
| Vitamin A | 455 mcg RAE | 700 mcg RAE | 4 | 6 | 6 | 2.1 | 4 mcg RAE | 459 mcg RAE | 6 | 2.07 |
| Vitamin C | 85 mg | 75 mg | 4 | 6 | 4 | 0.53 | 10 mg | 95 mg | 4 | 1.07 |
| Calcium | 1620 mg | 1200 mg | 4 | 8 | 4 | 1.4 | 6 mg | 1626 mg | 4 | 1.42 |
| Omega-3 | 1000 mg | 1100 mg | 5 | 7 | 7 | 0.64 | 24 mg | 1024 mg | 7 | 0.48 |
| Magnesium | 275 mg | 320 mg | 6 | 7 | 7 | 0.98 | 32 mg | 307 mg | 7 | 0.28 |
| Potassium | 4560 mg | 4700 mg | 8 | 6 | 6 | 0.18 | 422 mg | 4982 mg | 8 | 0.48 |

Alternative techniques for determining the index may be used. For example, the index may be computed in accordance with $$I = \max\left(0, 1 - \frac{\sum_{n=1}^{N} w_n(c_n, g_n) * \frac{\|c_n - g_n\|}{g_n}}{\sum_{n=1}^{N} w_n(c_n, g_n)}\right) \quad (6)$$

I is the index,
N is the number of nutrients in the set of nutrients,
$g_n$ is the target level for nutrient n,
$c_n$ is a consumed level of nutrient n, and
$w_n$ is a weight function that generates a weight for nutrient n based on a linear or non-linear function of the target level $g_n$ and the consumed level $c_n$.

Figure 2C:
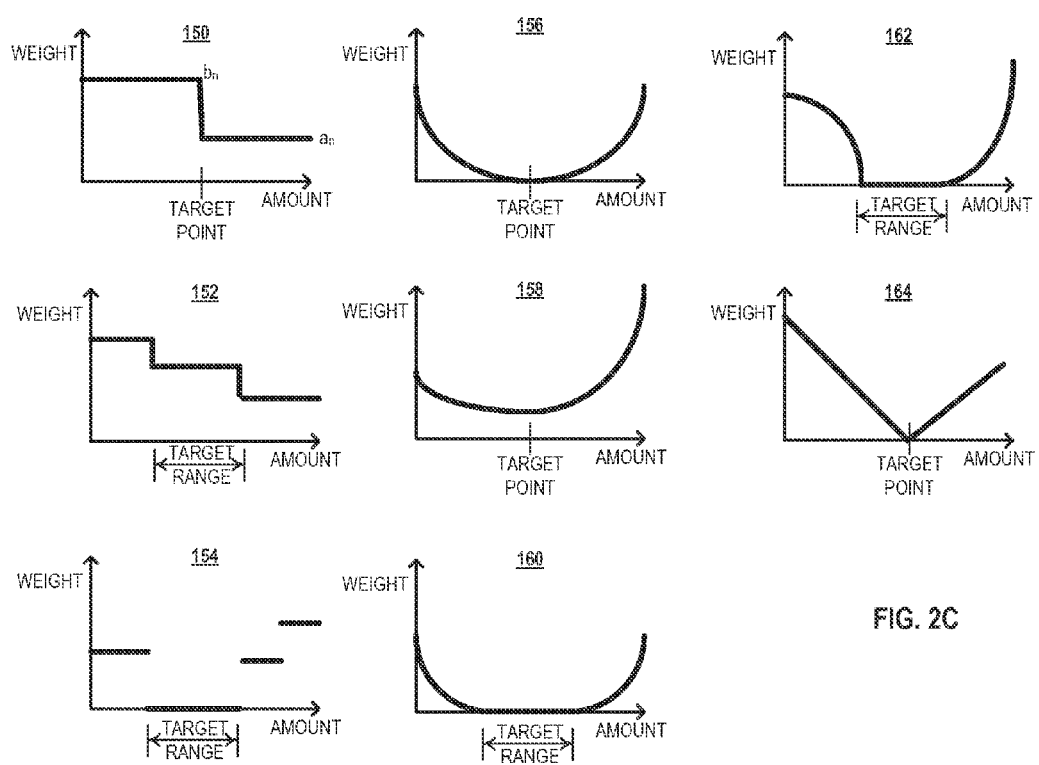
FIG. 2C includes example weight functions applied to comparisons between consumed levels and target levels of nutrients for providing nutrition analysis, according to an illustrative implementation.

The weight function $w_n$ used in Eq. 6 may take any of a number of forms, and may differ by nutrient, dietary program and user. FIG. 2C shows several example weight functions that may be used. Each weight function is plotted against an amount of the nutrient consumed by the user and includes a target point or range, a below-weight function $b_n$ (corresponding to the weight function when the consumed amount is below the target point or range), and an above-weight function $a_n$ (corresponding to the weight function when the consumed amount is above the target point or range).

In the case of weight function 150, a target amount for a nutrient corresponds to a single target point, meaning that the user is only considered to satisfy the target for the nutrient when the user's consumption level of the nutrient is the same as the target point value. In this case, each nutrient is assigned an above weight $a_n$ for when consumption of the nutrient exceeds the target level for that nutrient, and a below weight $b_n$ for when the consumption of the nutrient is less than the target level. Alternative weight functions are shown in diagrams 152-164 of FIG. 2C. In particular, weight functions 152, 154, 160, and 162 correspond to nutrients with target ranges, meaning that the target amount corresponds to a range of values (see rows corresponding to cholesterol and sodium in Table 1 for an example). In these cases, if the user consumption level of the nutrient falls within the target range, the nutrient may be labeled as "on target," and the nutrient is weighted accordingly.

In some implementations, the weight function is discontinuous, as illustrated in weight functions 150, 152, and 154. In these cases, the weight value chosen if the user's consumed amount falls at a discontinuous point may be dependent on the continuous portions of the weight function. For example, the chosen weight value may be a maximum, mean, median, or any other appropriate value derived from the weight function. The weight function may be linear, such as in diagrams 150, 152, 154, and 164, or nonlinear, such as in diagrams 156, 158, 160, and 162. In addition, the above-weight function $a_n$ and the below-weight function $b_n$ may be symmetric to each other, or may be non-symmetric. The weight function may have one or more convex and/or concave portions. The weight function could also be an empirically determined function (stored, for example, in a lookup table) that uses clinical data on the health outcomes associated with various consumption levels in order to weight the consumed levels appropriately. Additionally, the weight function can be adjusted based on the user's demographic features and health goals. The example weight functions shown in FIG. 2C are merely illustrative, and it will be understood that any suitable function may be used.

In some implementations, a nutrient may be associated with multiple target levels (where each target level may correspond to a specific number or a range of having an upper and lower bound) for different time periods. For example, target levels of calories may be 1500 calories per day, 10,500 calories per week, and 200-300 calories per meal (including, e.g., in the case of per-meal targets, different target levels specified for different meal classifications (e.g., 300 calories for breakfast). Similar target levels may be specified for other nutrients such as carbohydrates, proteins, fats, fiber, etc. Where multiple time-dependent target levels are specified for a nutrient, each target level is compared to a corresponding consumed level of the nutrient, and each comparison may be associated with a separate index contribution $IC_n$ as shown in Eq. 1.

Similarly, in some implementations, a nutrient may be associated with multiple time-based weight functions (or simply, weights). That is, different weights may be applied to the comparisons associated with the same nutrient but for different time periods. A nutrient may be associated with a weight for various time periods such a weekly weight, a daily weight, or a per-meal weight. These weights are generally independent of each other, although in some cases, the weight for one time period may be obtainable or derivable from the weight for another time period. As an example, the weight function applied to the comparison for the number of calories per day may be different from the weight function applied to the comparison for the number of calories per week. This flexible way of applying different weights may be desirable if, for example, it is more important that the user adhere to a daily caloric goal than to adhere to a weekly caloric goal, such that a higher weight is applied to the daily caloric goal than the weekly caloric goal. In this example, the user might significantly exceed a daily caloric goal for several days out of the week, and in an attempt to compensate for the excessive caloric intake, the user may excessively diet the remaining days of the week. In this case, the user might meet the weekly caloric goal while failing to meet the daily caloric goals. By applying a higher weight to the daily caloric goal than the weekly caloric goal, the user's meeting of the weekly caloric goal does not compensate for the user's deviation from the daily caloric goals. Similarly, different weights may be assigned to meal-based caloric goals and daily caloric goals, for example. The examples described herein are for illustrative purposes only, and one of ordinary skill in the art will understand that the systems and methods described herein may be used to apply different (or the same) weight functions to comparisons associated with any nutrient for different time periods.

Furthermore, any or a combination of the weighting methods described herein may be adapted and applied to other assessment systems not related to nutrition, such as sleep adherence assessment, wellness assessments, exercise adherence, medication adherence, etc. In particular, for each of the aforementioned applicable areas, the user may be attempting to follow a recommended or required regimen or program that includes multiple components that have different relative importance based on the nature of the component or the time period being assessed. The regimen or program may be analyzed according to its various components, with each component having an associated weight determined in accordance with the weighting functions described herein.

In some implementations, the index may be computed in accordance with $$I = \max(0, 1 - \Sigma_{n=1}^{N} f_n(c_n, g_n)) \quad (7)$$

I is the index,

N is the number of nutrients in the set of nutrients, $g_n$ is the target level for nutrient n, $c_n$ is a consumed level of nutrient n, $f_n$ is a contribution function that generates a contribution for nutrient n based on a linear or non-linear function of the target level $g_n$ and the consumed level $c_n$.

The contribution function $f_n$ may take any functional form, such as any of the functional forms described above with reference to the weight function $w_n$ and illustrated in FIG. 2C.

In some implementations, the systems and methods described herein provide a social networking experience for the users. For example, users of the system 120 may interact with one another over multiple user devices 108 (multiple devices not shown) by creating profiles of themselves and sharing their profiles with other users. For example, the system 120 may provide an interface for users with accounts on a separate social networking site. In particular, the system 120 may transmit some profile data of the users who are also participants in the separate social networking site. The participants may select an option to share their profile data stored and generated on the system 120 with the social network. The profiles may include user data such as the user's goals, favorite foods, recently consumed foods, index, or any other suitable data related to the user. The user may also choose to set privacy settings to make any of the user's data private. The user may transmit a request over the network 102 to another user to request or allow the viewing of each other's profile data, and similarly, the user may accept or reject such requests from other users. After a request is accepted, two users are connected and are able to view each other's profile data. In particular, one user may be able to view recipes created by another user, log foods consumed by the other user, exchange messages with the user, and/or view the other user's index data. By allowing users to interact with one another over the network 102, the system 102 provides a social networking experience for encouraging users to improve their diets and share recipes and foods. In addition, a contest may be implemented on the social networking system, where a winner may be selected based on a highest index score or a most improved index score over a time period. The winner of the contest may receive a prize such as a consultation with a nutritionist or physical trainer, or discounts or gift certificates to grocery stores or restaurants.

The method 210 of FIG. 4 ends at step 330 if the user wishes to display the index and does not wish to view a food recommendation. However, after determining the user's index, the systems described herein may also be configured to execute one or more techniques for determining one or more recommended foods for the user to consume in order to move the index closer to the target level. The server 104 may be programmed to execute one or more linear programming techniques to provide multiple recommendations for improving the index by balancing the need to increase deficient nutrients while preventing or reducing harmful increases in the consumption of nutrients that are already at sufficient levels in the user's diet. The system 100 may be configured to provide several types of food recommendations including: recommendations for multiple meals spanning a predetermined time period (e.g., a week), a recommendation for the next upcoming meal based on previously consumed meals, a recommendation for a new food to try, and combinations of these. Example techniques for providing these types of recommendations are described below with reference to FIGS. 5A-5C.

Figure 5A:
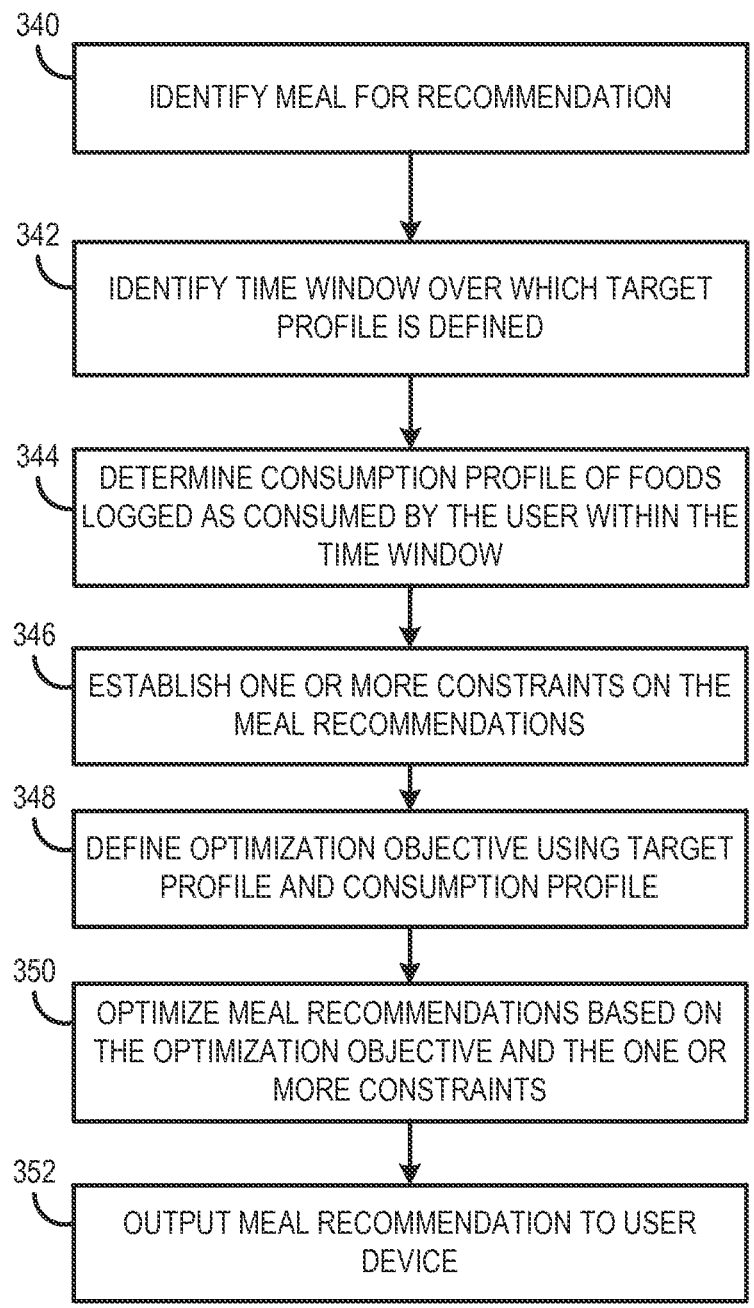
FIG. 5A is a flowchart of a method used by a computerized system to provide a recommendation of a meal to be consumed by a person, according to an illustrative implementation.

FIG. 5A is a flow chart of a method 300 used by the processor 105 of the server 104 (FIG. 1A) to recommend multiple meals to a user according to an illustrative implementation. The method includes the steps of identifying the meals for which recommendations are to be provided (step 340), identifying the time window over which the target profile is defined (step 342), and determining the consumption profile of the foods logged as consumed by the user within the time window (step 344). The processor 105 establishes one or more constraints on the meal recommendations (step 346), defines an optimization objective using the target profile and the consumption profile (step 348), and optimizes the meal recommendations based on the optimization objective and the one or more constraints (step 350). The processor 105 then outputs the meal recommendations to the user device 108 (step 352).

At step 340, the processor 105 identifies the meals for which recommendations are to be provided. The user may specify these meals, e.g., by selecting a "recommend meals for the rest of the week" option or by selecting one or more days for which meal recommendations are desired. Alternatively, the meals may be determined by the system 100 (e.g., by counting the number and type of meals remaining in the week according to the time and day at which the user logs in to the system 100). The identified meals may include a meal type (e.g., breakfast, lunch, dinner and snack) and a meal day (e.g., Wednesday, Thursday, Friday). For example, if a user requests meal recommendations for the rest of the week after lunch on Thursday, the processor 105 may identify the meals at step 340 as Thursday dinner, and breakfast, lunch, dinner and snack for each of Friday and Saturday.

At step 342, the processor 105 identifies the time window over which the target profile is defined. For example, a user's target profile may specify weekly nutrient targets, in which case which the system 100 is accumulating consumed nutrients over a one-week time window. At step 344, the processor 105 determines the consumption profile of the foods logged as consumed by the user within the time window (step 344). This allows the processor 105 to account for foods (and thus nutrients) already consumed in the time window when providing recommendations for meals in the remainder of the time window. In particular, the processor 105 may use the consumption profile to adjust the target profile over the time window to determine a modified target profile for use in generating the requested meal recommendations. The modified target profile is representative of what the user should consume for the remaining meals in the time window in order to achieve the target profile or maximize alignment of the user's diet with the target profile. In the modified target profile, the nutrient levels may correspond to a difference between the consumed nutrient levels (generated in step 326 of FIG. 4) and the target nutrient levels (generated in step 324 of FIG. 4). For example, the modified target profile may be formed by taking the original target profile (based on the user's selected dietary programs and health-related goals) and subtracting the consumption profile (corresponding to foods that the user has consumed in the portion of the time window that has already passed).

Figure 32:
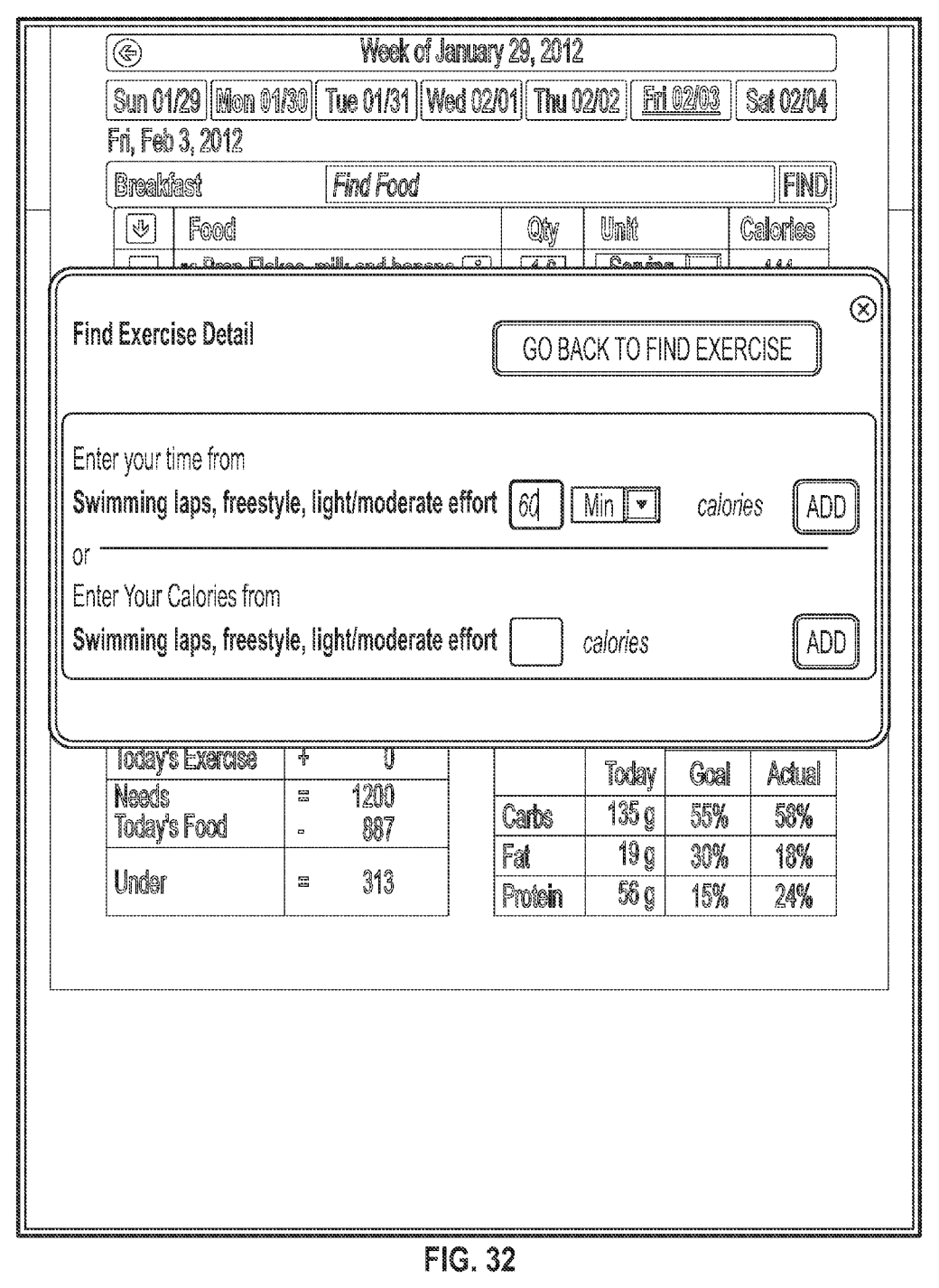

In addition, the target profile may be further modified to account for user activities such as exercise. In particular, the user may provide input to the user interface 112 information indicative of exercise that the user has performed. Based on the type of exercise, an effort level of the exercise, and the user's demographic features, the processor 105 may calculate an amount of calories burnt by the user during the activity. The user may also directly provide the number of burnt calories to the user interface. Examples of these displays are shown in FIGS. 31 and 32. The target profile may then be modified to account for the user's burnt calories by adjusting the daily caloric target goal by increasing the goal by the number of burnt calories, for example. In addition, the target amounts of some nutrients may be dependent on the number of calories, such that when the caloric goal is adjusted, the targets of these nutrients are similarly adjusted. For example, a target amount for fiber may be constrained by a goal that a user's intake be at least 14 grams of fiber per 1,000 calories. Increasing the caloric goal may then increase the fiber target amount. In addition, accounting for user activities such as exercise may result in further changes to the target profile, such as by increasing protein target amounts to facilitate muscle restoration and growth. By forming a modified target profile, the processor 105 accounts for the foods the user has recently consumed and the activities recently performed by the user to determine what to recommend to the user to consume next.

In step 346, the processor 105 establishes one or more constraints on the meal recommendations. These constraints may include constraints on the amount and nutrient content of foods in each meal, the amount and nutrient content of foods in a particular day, and the amount and nutrient content of foods over the time window, for example. One way to establish a constraint is to require an approximate total number of calories in a meal recommendation. For example, to determine a target caloric intake for a lunch recommendation, the processor 105 may compute:

$$\mathrm{cal}_{lunch,target} = \mathrm{cal}_{day,target} * \frac{avg\ \mathrm{cal}_{lunch,30\ days}}{avg\ \mathrm{cal}_{day,30\ days}} \qquad (8)$$

where avg $\mathrm{cal}_{lunch,\ 30\ days}$ corresponds to the average number of calories consumed at lunch over the last 30 days, avg $\mathrm{cal}_{day,\ 30\ days}$ corresponds to the average number of calories consumed in a day over the last 30 days, $\mathrm{cal}_{day,target}$ corresponds to the daily target number of calories for the user, and $\mathrm{cal}_{lunch,target}$ corresponds to the target number of calories for the lunch to be recommended.

In this example, the portion of the daily caloric target allowed for the recommended lunch is calculated using 30-day averages for lunch and daily caloric intakes. Any suitable averaging time period may be used. In addition, other methods for obtaining a historical caloric intake pattern may be used, including other statistics-based approaches such as taking a median of intakes, and pattern detection approaches. Using Eq. 8 to compute the target number of calories for a recommended meal helps to determine appropriate portion sizes of foods in the recommended meal. Eq. 8 is also helpful for determining an approximate breakdown of nutrients that are often determined by the total number of calories in a meal. For example, some dietary guidelines suggest that 30% of a person's calories should come from fat, 15% from protein, and 55% from carbohydrates. By first identifying a target number of total calories, appropriate target levels of these or other nutrients may then be determined for comparison to candidate meals.

Other constraints may be used to avoid or reduce potentially undesirable characteristics of meal recommendations. For example, for a meal recommendation, it may be undesirable to recommend to the user to consume an amount of a certain food that greatly exceeds a maximum amount of the food the user has previously consumed. Thus, the processor 105 may set a maximum amount of any food to recommend by requiring that any amount of a certain food in a recommended meal cannot exceed a proportion (e.g., two times, or any other suitable proportion or value) of a historical maximum amount the user has previously consumed. The historical maximal amount may be a maximum amount the user has consumed over a time period (such as a day, a week, a month, or any suitable time period), or may be the maximal amount the user has ever consumed. Furthermore, the historical maximum amount may correspond to the maximal amount the user has consumed in a meal of the same meal type as the meal recommendation, or may correspond to the maximal amount the user has consumed in any meal. Similarly, another constraint may be applied to the meal recommendation such that any amount of a certain food cannot be below a proportion (e.g., one third, or any other suitable proportion or value) of a historical minimum amount the user has previously consumed.

It may be desirable for each recommended meal to satisfy one or more criteria. In some implementations, it is desirable to recommend meals that are consistent with a user's eating habits, such as the user's average daily distribution of calories across meals. For example, small portion sizes for breakfast may be recommended for a user who typically does not eat a large breakfast. In some implementations, a recommended meal may be required to satisfy a desired distribution of nutrients. For example, a constraint may require that a certain number or range of calories of the meal come from proteins, carbohydrates, and fats or that a certain amount of carbohydrates is permitted only if provided in combination with specified amounts of protein and fiber. In some implementations, a user who is diabetic may wish to track his or her glycemic index on a meal-by-meal basis. Thus, the diabetic user may require that each recommended meal have a glycemic load within a desired range. In an example, the system 120 may communicate over the network 102 with a patient management system that stores or manages information regarding the user's blood glucose level. The patient management system may be a network-capable infusion pump or blood glucose device. In some implementations the patient management system may be a blood analyzer in a clinical setting or a portable analyzer in a home setting, where samples from the user may be taken and analyzed. The results of the analysis may be transmitted to the system 120, which may then identify foods or meals with appreciate glycemic loads for recommendation. In addition or alternatively, the user may be prompted to manually provide a blood glucose reading prior to the system providing food recommendations.

Additional constraints may arise if a user wishes to "budget" for a particular type of food or beverage over a certain time period. For example, the user may have a habit of consuming a cookie once a day and does not wish to change this habit. The processor 105 may then account for a daily cookie by considering the nutrient profile of a cookie when calculating a modified target profile by subtracting the cookie's nutrient profile from a daily target nutrient profile.

In step 348, the processor 105 defines an optimization objective using the target profile and the consumption profile. In some implementations, the optimization objective will be to provide meal recommendations that bring the user's dietary intake as close as possible to the modified target profile described above with reference to step 344. In some implementations, the optimization objective may take the form:

$$\min \sum_{n=1}^{N} w_n * \frac{\|r_n - g_n\|}{g_n} \quad (9)$$

I is the index,
N is the number of nutrients in the set of nutrients,
$g_n$ is the target level for nutrient n,
$r_n$ is the level of nutrient n in the recommended foods, and
$w_n$, is a weight applied to nutrient n.

This optimization objective may also be used as an index in any of the techniques described herein that utilize an index calculation. An index calculation may also be used as the optimization objective, in which the weights $w_n$ may be different from the weights used for calculating the index. It may be desirable to use different weights $w_n$ when performing meal recommendations and when calculating a user's index. For example, when performing meal recommendations, it may be desirable to weight certain nutrients more heavily than others. In particular, if a dinner recommendation is being generated for a user who had deficient levels of a nutrient for breakfast and lunch, the optimization objective may heavily weight the deficient nutrient. In contrast, the weights when used in calculating the index might not necessarily depend on the user's recent consumption history in the same manner. In this way, recommendation weights can be chosen to preferentially recommend meals that achieve certain nutritional targets (e.g., a target number of calories), but deviations from that target need not result in as severe a "penalty" in the index as would occur if the recommendation weights were used in the index calculation. The weights may be stored on an electronic database in communication with the server 104 over the network 102, or the electronic database may be otherwise in communication with the server 104.

At step 350, the processor 105 optimizes the meal recommendations based on the optimization objective and the one or more constraints. In some implementations, the processor 105 is configured to perform one or more linear programming techniques to minimize or maximize the objective function of step 348 (as appropriate), subject to the constraints of step 346. Linear programming techniques are mathematical tools used to determine an optimal solution of an objective function while respecting a set of linear equality and inequality constraints. Here, a linear programming technique may be used to determine an optimal solution ($r_n$) that minimizes the objective function of Eq. 9.

The foods over which the optimization is performed at step 350 may be any food stored in a known foods database (such as known foods database 106A of FIG. 1B) or may be a food drawn from a subset of a known foods database (e.g., a sub-database that includes kosher foods). In some implementations of step 350, the foods from which the meal recommendations are chosen during the optimization are the foods previously consumed by the user, such as a single food previously consumed or a meal previously consumed by the user. The processor 105 may, for example, optimize over foods from the consumed foods database 106B (FIG. 1B) that includes only foods logged by the user as having been previously consumed. By selecting the recommended foods from the database of foods previously consumed by the user (and by adjusting the portion size), the user can receive analytically determined suggestions for improving dietary consumption by eating foods the user already consumes (and may like).

Furthermore, the set of foods iterated over by the processor 105 for recommendation may be subject to additional constraints. For example, the user may have indicated specific medical conditions (such as high blood pressure, high cholesterol, or any other medical condition that may affect the overall wellness of the user), and the processor 105 may avoid recommending foods that would adversely affect the user's health, or recommend foods that minimize such effects.

In some implementations, the processor 105 is configured to ensure there is a certain degree of variety in the multiple meal recommendations. A degree of variety is desirable to avoid a situation in which the processor 105 repeatedly recommends in multiple meal recommendations the same food or type of food. For example, in an extreme case, it would be undesirable to recommend only meals consisting entirely of bread to a user. To achieve this variety, the processor 105 first uses the method 300 of FIG. 5A to reach an initial set of meal recommendations. Then, the processor 105 repeats the method 300 of FIG. 5A, this time establishing an additional constraint in step 346. In particular, the processor 105 runs the optimization for a second time, this time with an input parameter including the initial set of meal recommendations resulting from the first optimization. The additional constraint may require that at least 20% (or any other suitable amount) of the meal recommendations not include any of the same foods that were selected in the initial set of meal recommendations. In another example, the additional constraint may require that at least 20% (or any other suitable amount) of the meal recommendations do not include any of the same meals that were reached in the initial set of meal recommendations. Alternatively, the additional constraint may require that exactly 20% (or any other suitable amount) of the meal recommendations meet some criteria. The user may set a desired degree of variety for the meal recommendations, such that the degree of variety may be different for different users. By repeating the method 300 of FIG. 5A with different constraints, the processor 105 includes an opportunity for a desired variety of foods to be recommended.

Figure 35:
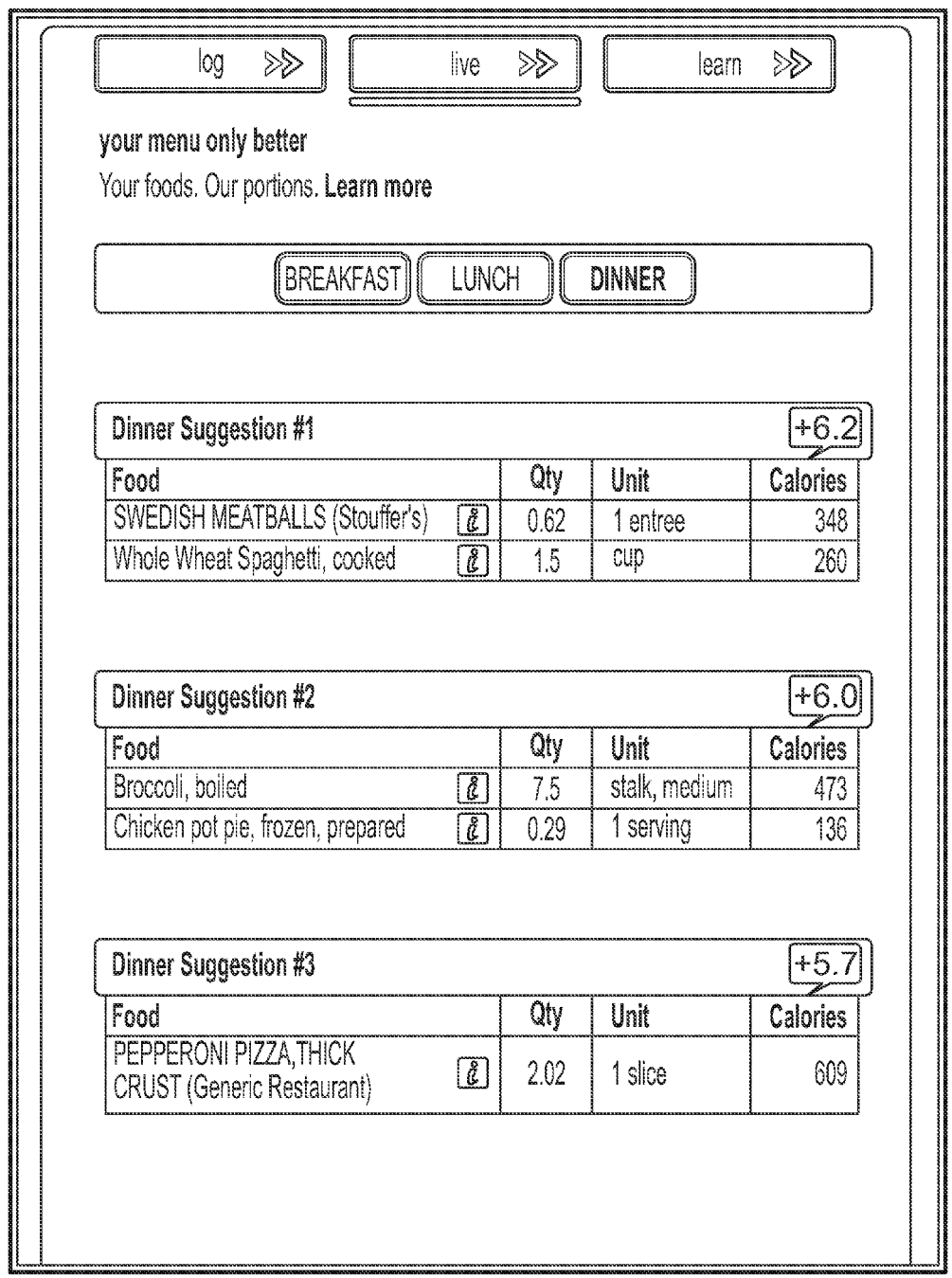
FIG. 35 is an example screen that displays meal suggestions for the user, corresponding to meals in the consumed foods database for the user, according to an illustrative implementation.

At step 352, the processor 105 outputs the meal recommendations to the user device 108. An example screen shot of a set of three meal recommendations is shown in FIG. 35.

Figure 5B:
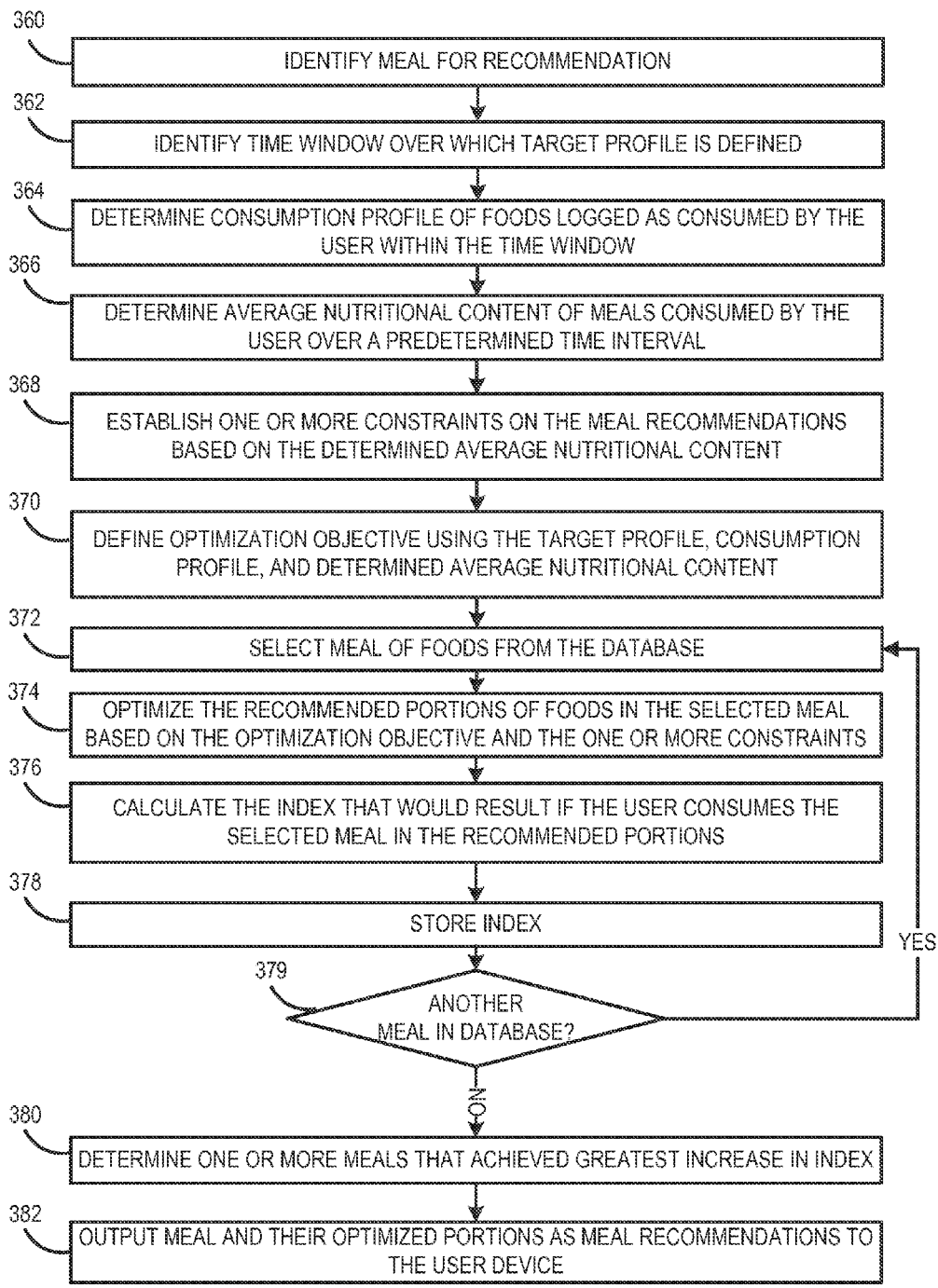
FIG. 5B is a flowchart of a method used by a computerized system to provide a recommendation of a meal with specified portion sizes to be consumed by a person, according to an illustrative implementation.

FIG. 5B is a flow chart of a method 310 used by the processor 105 of the server 104 (FIG. 1A) to provide a recommendation for the next upcoming meal, based on previously consumed meals, which include a combination of specified portions of one or more foods, according to an illustrative implementation. This method advantageously considers which combinations of foods a user has previously consumed together as a meal in determining which meals to recommend. In particular, the recommendation provided using the method 310 of FIG. 5B may include a combination of foods that the user has previously consumed together in a meal, but with possibly different portion sizes optimized to achieve a nutritional objective. Doing so may improve the likelihood that user will follow the recommendation since the user is more likely to consume a recommended meal if the meal contains a combination of foods that the user has previously consumed in a meal. Alternatively, the recommendation provided using the method 310 of FIG. 5B may include a combination of foods that the user has not previously consumed together in a meal, but may include foods that the user has consumed for the same type of meal, such as a combination of breakfast foods, lunch foods, dinner foods, or snack foods.

The method 310 may also provide a suitability rating for one or more foods selected by the user or recommended by an independent third-party. The suitability rating provides an indicator of whether consuming the one or more foods (per the original recommendation or a modified version thereof) would improve the alignment between the user's nutrient consumption and the user's nutritional goal, weight goal, or other goal. The suitability rating may be determined based on the index impact of the food(s). For example, the suitability rating may be based on the degree of improvement in the index associated with the combination of foods. The suitability rating may be provided to the user using any suitable indicator. For example, the suitability rating may be a numeric value (such as a number between 1 and 100 or 0 and 1), an alphabetical symbol (such as a grade from F to A+), an indicator (e.g., a color-coded indicator) selected based on which of multiple predetermined impact ranges the change in alignment falls within, a color selected from a color gradient that represents a range of the suitability rating, a graphical icon (e.g., an arrow pointing up or down) that indicates progress toward the user's goals or otherwise, a binary value or flag indicating whether the combination is suitable for recommendation, a combination of these, or any other visible or audible indicator that communicates whether the recommendation could improve the alignment between the user's nutrient intake and the user's goal(s) and/or an indication of the predicted change in the alignment between the user's nutrient intake and the user's goal(s). The suitability rating may include a category selected from a group of categories including suitable for recommendation, not suitable for recommendation, neutral, or any other suitable category representative of a degree of enthusiasm for a particular recommendation. In particular, having a category of foods not suitable for recommendation may include displaying a cautionary warning to the user not to consume a particular food or foods. The suitability rating may be determined based on a deviation profile representative of a comparison between the consumption profile and the target profile. In particular, an index impact corresponding to a predicted change to the user's nutritional index if the user consumes a particular combination of one or more foods may be determined to assess a predicted degree of improvement. The index impact may be used to identify a meal appropriate for recommendation as is described below.

The method 310 of FIG. 5B includes the steps of identifying the meal for which a recommendation is to be provided (step 360), identifying the time window over which the target profile is defined (step 362), determining the consumption profile of the foods logged as consumed by the user within the time window (step 364), and determining the average nutritional content of meals consumed by the user over a predetermined time interval (step 366). The processor 105 then establishes one or more constraints on the meal recommendations based on the determined average nutritional content (step 368) and defines an optimization objective using the target profile, the consumption profile, and the determined average nutritional content (step 370). The processor 105 selects a meal (i.e., foods previously logged by the user as having been consumed together in a sitting) from the database 106 (step 372) and optimizes the recommended portions of the foods in the selected meal based on the optimization objective and the one or more constraints (step 374). The processor 105 calculates the index that would result were the user to consume the selected meal in the recommended portions (step 376), and stores the index (step 378). The processor 105 repeats steps 372-378) for each meal in database 106. The processor 105 then evaluates the one or more meals that achieved the greatest increase in the index (step 380) and outputs the meals and their optimized portions as meal recommendations to the user device 108 (step 382).

In step 360, the processor 105 identifies the meal for which a recommendation is to be provided. This meal may be specified by the user (e.g., by selecting an option for a dinner recommendation for a particular day from a calendar display) or may be determined by the system 100 (e.g., by identifying the likely next meal given the current time of day in the user's time zone). At step 362, the processor 105 identifies the time window over which the target profile is defined, and at step 364, the processor 105 determines the consumption profile of the foods logged as consumed by the user within the time window. These steps may be performed as described above with reference to steps 342 and 344, respectively, of FIG. 5A.

In step 366, the processor 105 determines the average nutritional content of meals consumed by the user over a predetermined time interval. For example, the processor 105 may determine the average nutritional content in all lunches the user has consumed over the last thirty days, or any other suitable time interval, and use this average as a representative lunch. This may be repeated to derive a representative breakfast, dinner, and snack.

In step 368, the processor 105 establishes one or more constraints on the meal recommendations based on the determined average nutritional content (as determined at step 366). Example constraints have been described in relation to FIG. 5A. In addition to these constraints, another possible additional constraint includes the use of the representative meals (or the representative snack) derived in step 366. For example, the representative meals may be used to predict meals outside of the meal for which a recommendation is sought. For example, when a meal recommendation for dinner on a Wednesday is desired, it may be assumed that the user will consume the representative breakfast, lunch, dinner, and snack on Thursday. In this case, a meal recommendation is the result of an optimization scheme that makes realistic assumptions regarding what the user is likely to consume.

In step 370, the processor 105 defines an optimization objective using the target profile, the consumption profile, and the determined average nutritional content. In some implementations, the optimization objective will be to provide portions of foods in a meal that brings the user's dietary intake as close as possible to the modified target profile described above with reference to step 344. In some implementations, the optimization objective may take the form of Eq. 8 above, or any of the index calculations described herein.

The processor 105 next iterates steps 372-378, considering each meal in turn and optimizing the recommended portions of the meals in that meal to achieve the largest possible improvement in the user's index. This iteration corresponds to an inner optimization loop that determines the portion sizes of each food in the meal that maximize the index impact or cause the index impact to exceed a threshold. In some implementations, the meal is assigned a grade based on the determined index impact. The grade may be determined in a number of ways based on the index impact. For example, the index impact may be a number, and the grade may be based on a quantized version of the number by identifying ranges for the index impact and determining the grade based on which range the number falls. The grade may be a letter, a number, a shade or color, a graphic, or any other suitable indicator for representing how favorable a food or meal would be for recommendation to a user.

In particular, in step 372, the processor 105 selects a meal from the database 106. As discussed above, a meal may include the collection of foods previously consumed by a user and entered into the user interface 112 as a whole meal at least once in a time period, where the time period may be during the last week, the last month, or any other suitable time period.

In some implementations, a meal may include a combination of foods that the user has previously consumed and entered into the user interface 112, but not necessary consumed together as a whole meal. In this case, the processor 105 may construct new meals not previously consumed as whole meals by the user, though the user did previously consume each food in the new meal. These implementations may be particularly useful when none the pre-existing whole meals can be modified to obtain a substantial improvement in the alignment of the user's diet with the user's dietary goals. Such across-meal permutations can provide a substantial improvement in the user's index while still recommending foods that are already consumed and possibly favored by the user. Thus, depending on the variety of the foods that the user consumed, a large number of across-meal permutations with different food combinations may be performed to identify an appropriate combination of foods for recommendation to the user. In an example, a user's breakfast foods may be tracked for a certain time period and stored in an electronic database. The user may provide an input to the user device 108 indicating that the user wishes to view a new combination of breakfast foods. Various permutations of the stored breakfast foods may be iterated over to identify one or more appropriate combinations of foods and portion sizes for recommendation.

Meal information may be stored in the electronic database 106 (FIG. 1A) in any of a number of ways (e.g., as described above with reference to the data structures of FIGS. 2A and 2B). In step 374, the processor 105 optimizes the recommended portions of the foods in the selected meal based on the optimization objective and the one or more constraints.

Linear programming techniques, as described above, may be used to determine the optimal solution to the optimization objective subject to the one or more constraints.

In step 376, the processor 105 calculates the index that would result were the user to consume the selected meal in the recommended portions, and stores the index in step 378. The index may be calculated in accordance with any of the index calculation techniques described herein. For example, the processor 105 recomputes the index with the nutrient levels of the candidate food added to the user's consumed nutrient levels.

Referring now to FIG. 5B, the processor 105 repeats steps 372-378 for each meal in database 106 to similarly optimize the portion sizes of other previously consumed meals in the electronic database 106. This optimization produces one or more candidate meal recommendations that each corresponds to a combination of foods previously eaten together by the user as a meal, adjusted to improve (or maximize) the index impact of the meal by modifying the portions of the foods within the meal. For each meal considered during the optimization, the candidate meal with optimized portion sizes that also maximizes the index impact or causes the index impact to exceed a threshold is the optimal version of that meal. Thus, the user will receive at the user interface 112 a meal recommendation that includes combinations of foods that the user has previously consumed together in a meal, but with possibly different portion sizes.

In step 380, the processor 105 determines the one or more meals that achieved the greatest increase in the index and outputs the meals and their optimized portions as meal recommendations to the user device 108 in step 382.

Figure 5C:
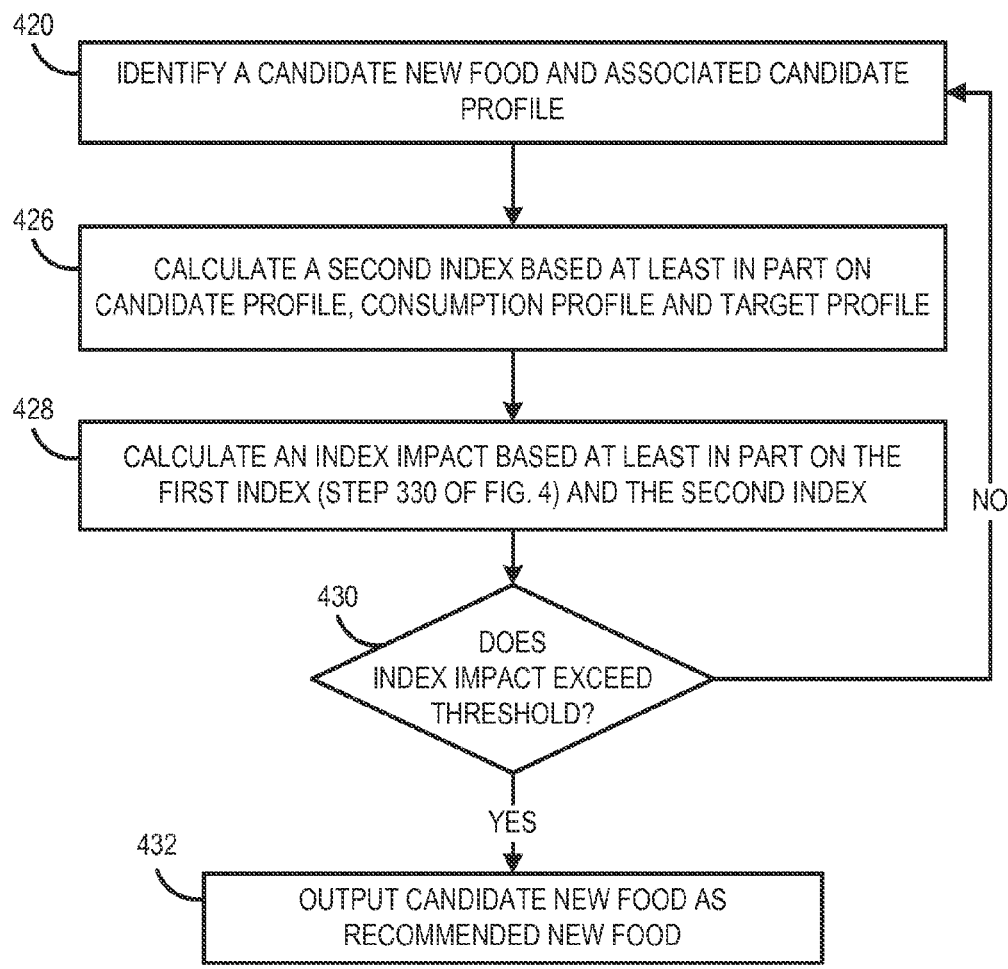
FIG. 5C is a flowchart of a method used by a computerized system to provide a recommendation of a new food to be consumed by a person, according to an illustrative implementation.
Figure 40:
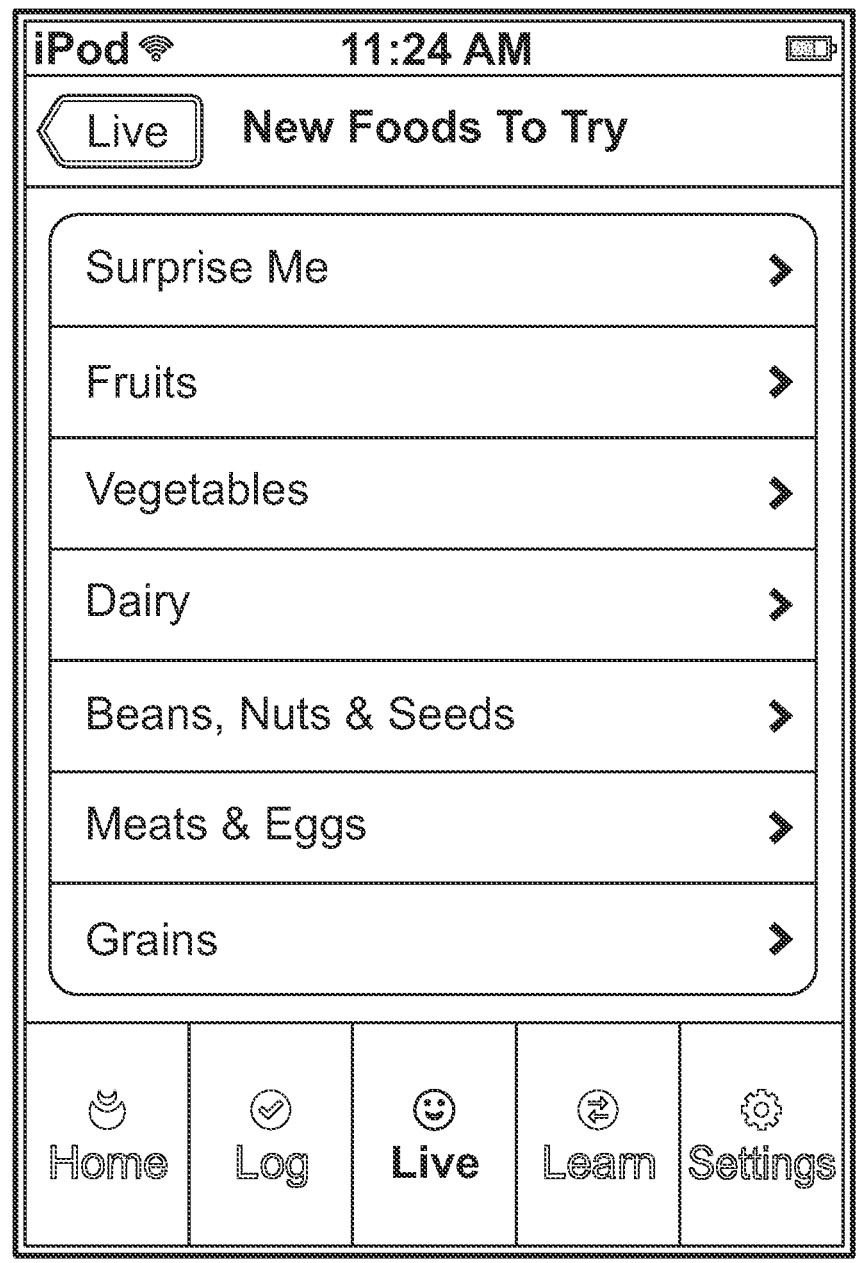
Figure 41:
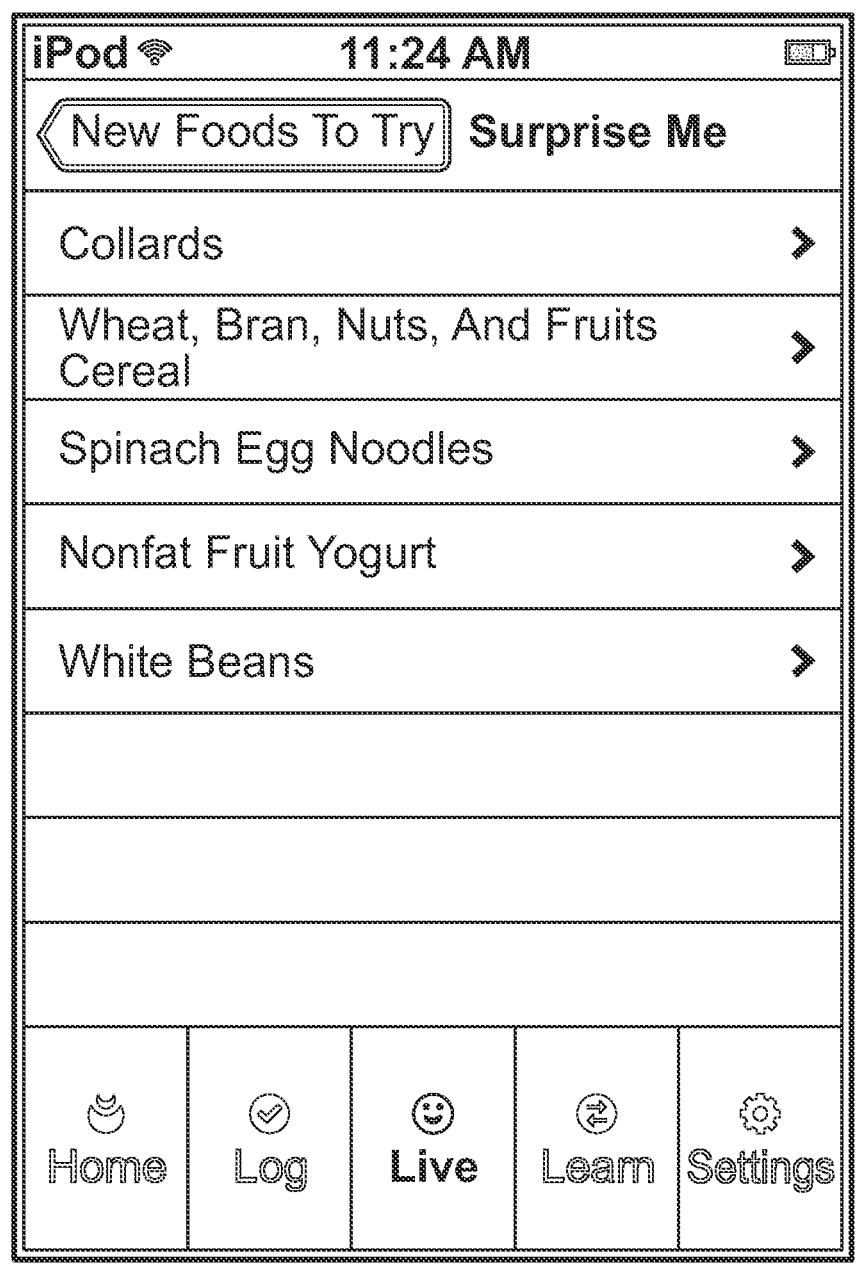

FIG. 5C is a flowchart of a method 320 used by the processor 105 of the server 104 (FIG. 1A) to recommend a new food to the user, according to an illustrative implementation. New food recommendations may be provided to a user in response to, for example, an indication in the dietary program that the user desires to try new foods. A user may also select a "new food" option via the user interface 112 of the user device 108 to be provided with a new food recommendation. In addition, the user may select a category of foods to view new food recommendations, such as fruits, vegetables, dairy, or any other food category. An example display of a screenshot where the user selects a food category is shown in FIG. 40.

In some implementations, the processor 105 determines when the index associated with the user reaches a plateau. For example, a plateau may be reached if the user is consistently consuming foods selected from a very limited set of foods that do not provide the nutritional variety that may be required to improve an alignment between the user's diet and the user's nutritional needs. In this case, it may be difficult for the index of the user to increase above the plateau value unless one or more new foods are introduced to the user. Thus, upon identifying an index plateau associated with a user, a "new food" recommendation may be provided to the user. In addition, the foods consumed in the user's meals may be combined in various ways to generate a meal recommendation to the user to try to increase the user's index above the plateau value. For example, a number (three, for example) of foods may be selected from the set of foods the user has consumed for the last number (thirty, for example) of breakfasts to form a new candidate meal. The effect of the user consuming the candidate meal may be evaluated by re-computing the index, including the foods in the candidate meal as consumed foods. If the effect on the index is positive, another similar combination of foods may be selected to generate another candidate meal. Alternatively, if the effect of consuming the candidate meal on the index is negative, an entirely different combination of foods may be selected. In general, any number of foods may be selected to be combined for a candidate meal. These foods may be selected randomly, or based on previous calculations of other candidate meals.

The method 320 of FIG. 5C includes the steps of identifying, in the database 106, a candidate food from a set of foods that the user has not previously consumed and nutrient levels contained in the candidate food (the "candidate profile") (step 420). The processor 105 then calculates a second index based on the candidate profile, the user's consumption profile, and the target profile (step 426). The processor 105 also calculates an index impact, which is based at least in part on the first index calculated in step 330 (FIG. 4) and the second index calculated in step 426. If the index impact exceeds a threshold (decision block 430), the processor 105 outputs identifying information for the candidate food (e.g., identification number, name, nutritional information) to the user device 108 as a recommendation (step 432). Otherwise, the processor 105 identifies a next candidate food from the database 106 (step 420) and re-runs the analysis.

In step 420, the processor 105 identifies a candidate food stored in the electronic database 106 and its nutrient levels (the "candidate profile"). For each nutrient in a set of nutrients, the candidate profile includes a candidate nutrient level, corresponding to the amount of the nutrient in the candidate food. When a new food is to be recommended, the candidate food may be drawn from the food entries in the known foods database 106A (FIG. 1B) which have not yet been logged as having been consumed by the user (i.e., do not appear in the consumed foods database 106B (FIG. 1B)).

In step 426, the processor 105 calculates a second index by recalculating the index (using, for example, Eq. 1-3 above) after augmenting the user's consumption profile with the candidate profile, as if the user had consumed the candidate food. In step 428, the processor 105 calculates an index impact, representing a change to the index if the candidate food is consumed by the user. The index impact is equal to the first index (calculated at step 330 of FIG. 4) subtracted from the second index (calculated at step 426 of FIG. 5). A positive index impact indicates that the second index exceeds the original index, meaning that if the user were to consume the candidate food, the user's index would increase, thereby causing the user's consumption profile to approach the user's target profile. Similarly, a negative index impact indicates that consuming the candidate food would cause the user's consumption profile to deviate from the target profile.

Referring now back to Table 1, columns G-J list the various components used for calculating the index in relation to Eq. 1-3, for the case when a candidate food is a banana. Table 1 includes amounts of several nutrients in the candidate food (column G), the user's consumed nutrient levels if the user were to consume the candidate food (column H, the resulting of adding columns A and G), second active weights (column I), based on a comparison between columns B and H, and a second index contribution (column J) based on the total columns B, H, and I. The resulting second index is 0.85. Compared to the original index of 0.81, this results in an index impact of +0.04. Thus, consuming the banana would increase the user's index by 0.04.

Referring now to FIG. 5C, at decision block 430, the processor 105 determines whether the index impact exceeds a threshold. The threshold may be a predetermined threshold (e.g., a change of 0.01 or more for an index that ranges from zero to one) or a dynamically determined threshold. For example, the processor 105 may iterate over all candidate foods in the database and select the food(s) with the highest index impact(s) (e.g., the threshold is set to the index impact of the candidate food with the fifth highest index impact so that the foods with the top four index impacts are recommended). If so, the processor 105 outputs the candidate food as a recommendation in step 432. For example, the processor 105 transmits information about the candidate food (e.g., its nutritional profile) and its index impact to processor 105, which then displays the index impact and the candidate food as a recommendation via the user interface 112. Examples of recommendation displays on the user interface 112 are shown in FIGS. 34 and 35. Alternatively, if the processor 105 determines that the index impact calculated in step 428 does not exceed a threshold, the method returns to step 420 to select another candidate food in the database 106.

The method 320 therefore identifies one or more foods associated with an index impact that exceeds a threshold. In some implementations, the index impact is determined based on a weighted function of deviation amounts between nutrient levels in the food and target nutrient levels associated with a person. Because different weights may be used for different nutrients, some nutrients are deemed to be more important (if they have higher weights, for example) than other nutrients for a particular person. In this case, a recommended food, if consumed by the person, would likely improve an alignment of one nutrient (a nutrient with high weight, for example) while simultaneously reducing a negative impact on an alignment of another nutrient (a nutrient with lower weight, for example).

The method 320 includes identifying candidate foods from a database including foods not previously consumed by the user. In general, the method 320 may be used with any database described herein, including the known foods database 106A, the consumed foods database 106B, a new foods database, any other suitable foods database, or a combination thereof.

In some implementations, one or more of the components of the systems of FIGS. 1A-1C are used in a system for ordering food in a restaurant. In particular, the known foods database 106A may include a list of menu items from the restaurant and the corresponding nutritional content of the menu items. The systems and methods described herein may be used to recommend one or more items from the restaurant's menu for the user to consume. As an example, upon entering the restaurant, the user device 108 may display a list of menu items specifically recommended for the user. The list may be sorted according to a calculated index impact associated with each menu item, such that the items with the most positive index impacts are displayed near the top of the screen of the user device 108. As another example, the user device 108 may be configured to display one or more recommended meals specific to the user according to a desired meal configuration. For example, the user may provide input to the user device 108 indicating that the user wishes to consume a beverage, an appetizer, and an entrée at this restaurant. In this case, the user device 108 may display one or more combinations of a beverage, an appetizer, and an entrée based on alignment of the nutritional content of the meals and the user's nutritional goals (e.g., the most nutritionally beneficial or the least nutritionally harmful combinations). For example, the user device 108 may recommend a combination that, if consumed by the user, would cause the user's index to increase. In some implementations, the user device 108 is equipped with GPS technology such that the user device 108 is configured to automatically display the menu recommendations without requiring the user to enter the restaurant's information.

Figure 5D:
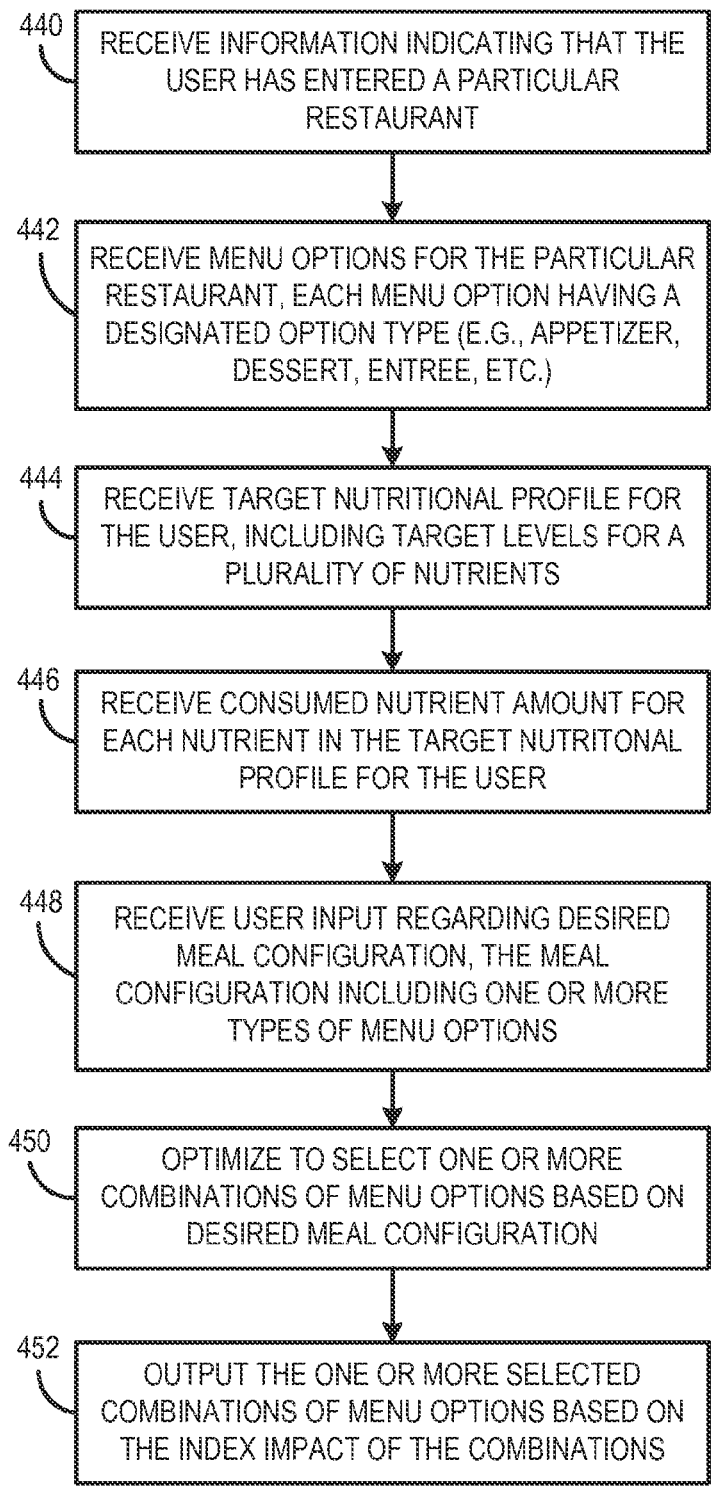
FIG. 5D is a flowchart of a method used by a computerized system to provide a recommendation of one or more menu options in a restaurant, according to an illustrative implementation.

The method 330 of FIG. 5D may be used for identifying one or more restaurant menu items suitable for recommendation to a user, according to an illustrative implementation. The recommendation of one or more restaurant menu items is based on improving the alignment between the user's nutritional goals and consumed foods using any of the mechanisms described herein. For example, the recommendation may be performed by using linear programming methods to minimize deviations between target levels and consumed levels of various nutrients.

At step 440, the processor 105 receives information indicating that the user has entered a particular restaurant. The information may be provided manually by user input, or may be detected automatically by the system based on the location of a GPS-enabled user device. For example, the user device 108 (e.g., a mobile phone) may be enabled for recommendation of restaurant menu items.

In response to detecting that the user has entered a particular restaurant, the method 330 may receive at step 442 menu options for the particular restaurant. The menu options may be received from a restaurant menus database (not shown) accessible by the processor 105 performing the method 330, and similar to the databases discussed above. The menu data may be received from an external source, such as directly from the restaurant or a third party. The restaurant menus database can include a list of menu options (e.g., foods, drinks, etc.) offered by the restaurant along with nutritional content information of the menu option, an option type associated with each menu option (e.g., appetizer, entree, side dish, dessert, salad, beverage, or any other suitable course provided by the particular restaurant). In addition to the menu options, at step 442 the method 330 can receive from the menus database one or more option types for each of the menu options. Menus of a selected set of restaurants may be preloaded to the user device 108, based, for example, on the popularity of the restaurant, past visits by the user, the geographical proximity of the restaurant to the user, or any other suitable user-related characteristics.

At step 444, the processor 105 receives the target nutritional profile for the user, including a target levels for a plurality of nutrients. As discussed above, the target profile is specifically generated for the user based on a selected dietary program, which may include other user-selected constraints or goals. The processor 105 may also receive profile data related to the user. Based on the user's profile data, the processor 105 may filter the received menu options such that a set of remaining menu options are suitable for the user's needs. For example, if the user has any allergies or dietary restrictions, the menu options that include such ingredients or foods may be removed prior to optimization.

At step 446, the processor 105 receives a consumed nutrient amount for each nutrient in the target nutritional profile for the user. The set of consumed nutrient amount for the nutrients may correspond to a consumption profile. In certain implementations, the consumption profile corresponds to all foods the user has indicated as being consumed in the last day, week, month, or any other selected time period. An example of a consumption profile is shown in column A of Table 1, and examples of consumption profiles for particular foods are shown in FIGS. 18 and 42 and would include the same nutrients as those in the user's target profile.

At step 448, the processor 105 receives user input regarding a desired meal configuration. The user may be prompted to provide the input regarding a desired meal configuration (including one or more option types) at step 448. For example, the user may specify that he or she desires to choose a three-course meal including an appetizer, an entree, a dessert, and perhaps a beverage. Similarly, the user may indicate that the user wishes to consume a two-course meal, and is willing to consider meals including an appetizer and an entrée or an entrée and a dessert. Depending on the desired meal configuration, the processor 105 may filter the menu options received at step 442 to exclude option types not included in the desired configuration such that only the menu options that the user would consider consuming are included in the subsequent analysis.

In addition, the user input may include some other parameters, such as how hungry the user is, any cravings for particular foods or types of food that the user has, an amount of money that the user is willing to spend on the meal, etc. In addition, the user input may include a desired type of menu option including a more specific type of food, such as an appetizer with shrimp, an entrée with chicken, or a dessert with chocolate, for example. In some implementations, the set of menu options for the particular restaurant is filtered based at least in part on the user input.

In general, the user input may be used in the analysis of the restaurant menu items to identify, filter, and sort the menu recommendation results. Alternatively, the application may be configured to have default settings (e.g., information learned over time about the user and stored in the user profile) such that no or minimal user input is required to generate recommendation of menu items at the restaurant. An example of a default setting may include deducing, based on historical data about the user, that the user would likely wish to consume an appetizer, an entrée, and a beverage at the particular restaurant.

An optimization is performed to select one or more combinations of menu options (step 450), and one or more combinations of menu options are output to a user device based on the index impact of the combinations (step 452). Although the meal configuration may be provided successively after each component of the meal is selected, method 330 preferably allows the user to specify the entire configuration simultaneously prior to selecting any component of the meal. By receiving the user's desired meal configuration, the method 330 can optimize across the multiple components of the meal at the same time in order to propose a combination that meets the desired configuration while providing the maximum improvement in the alignment between the impending meal and the user's dietary needs. Such an approach generally provides a more nutritionally balanced meal compared to an approach that optimizes on only one component of the meal at a time and moves on to the next component after the user selects an option for the prior component. It is understood, however, that in some instances, e.g., where a large number of menu options are provided (and thus making optimization across all permutations computationally costly), the method 330 may employ a sequential optimization approach.

Returning to method 330, at step 450, the processor 105 performs an optimization process to select one or more combinations of menu options that conform to the desired configuration. For example, if the user may have indicated at step 448 that the user wishes to consume a beverage, an appetizer, and an entrée at the restaurant, the processor 105 iterates over various combinations of possible menu options (that remain after optionally filtering out the set of inapplicable menu options) to form candidate meals (each including a beverage, an appetizer, and an entrée, for example). The processor 105 generates or receives from another source a predicted impact on the user's nutritional index for each of the candidate meals. The predicted index impact indicates a predicted change in the user's index if the user consumes the menu item or combination, and may be positive or negative for any given combination.

In addition, additional constraints may be used during the optimization process. For example, the cost of each restaurant menu item might be used as a factor in the optimization such that prohibitively expensive items are excluded from the analysis. Similarly, the recommendation of more expensive menu items may be assigned less priority or lower rankings than cheaper options, based on a weighting function that may take into account the user's specific economic constraints.

At step 452, the processor 105 outputs one or more combinations of menu options based on the index impact of the combinations. Each combination may be provided along with an index impact associated with the combination. For example, the display may include a sorted list of a number of recommended menu options. The list may be sorted according to the predicted impact on the user's index. The output, which may be displayed on user device 108, may include multiple pages, and the user may select to scroll or view other pages of the list. The user may also rerun the analysis by changing the desired configuration or by manually excluding specific items from the menu if he or she does not like any of the proposed combinations. By displaying the menu combinations along with the predicted index impact, the systems and methods described herein provide more information than a binary recommendation system, which simply tells a user which food items are acceptable or unacceptable. In particular, a binary recommendation system might simply provide a user with one of two options—consume this item or do not consume this item. By providing the user with a personalized score for each combination of menu options, the user may make an informed choice when deciding which menu options to order. In some implementations, only combinations associated with index impacts that exceed a threshold are displayed to the user.

The optimization process is described above in relation to selecting combinations of menu options. However, the optimization process may also be extended to single menu option optimization. In this case, the user input provided at step 448 may include that the user wishes to consume a single menu option of a particular type, such as an entrée. In this case, the optimization is performed over single entrée menu options. The processor 105 iterates over each of the entrées that remain after filtering and identifies a predicted impact on the user's index if the user consumes the entrée. In particular, the processor 105 may assume that the user would consume one serving size of the entrée, or the entire entrée. In general, the optimization process may be used for optimizing over any number of menu options in any combination.

In some implementations, the optimization process may include sequentially performing multiple single menu option optimizations. For example, the user may indicate that the user wishes to select an entrée first, followed by an appetizer, and followed by selection of a beverage. In this case, the processor 105 may perform the single menu option optimization for an entrée and provide several entrée recommendations to the user. Upon receiving a selection from the user of one of the recommended entrees, the processor 105 then performs the single menu option optimization for the appetizer, after updating the user's index to account for the selected entree. This second optimization process then provides several appetizer recommendations to the user, who makes a selection of one of the appetizers. This process is repeated after the user's consumption profile is updated to include the nutrients from the selected appetizer, and the optimization process is repeated a third time to identify a suitable beverage. In general, the optimization process described herein may be performed using a combination approach or using a sequential approach, and either approach may be used based on user input or a default setting.

The steps of the method 330 are in the shown order for illustrative purposes only, and one of ordinary skill in the art will understand that any step may be omitted, the order of the steps may be modified, or any steps may be performed simultaneously, without departing from the disclosure.

Figure 5E:
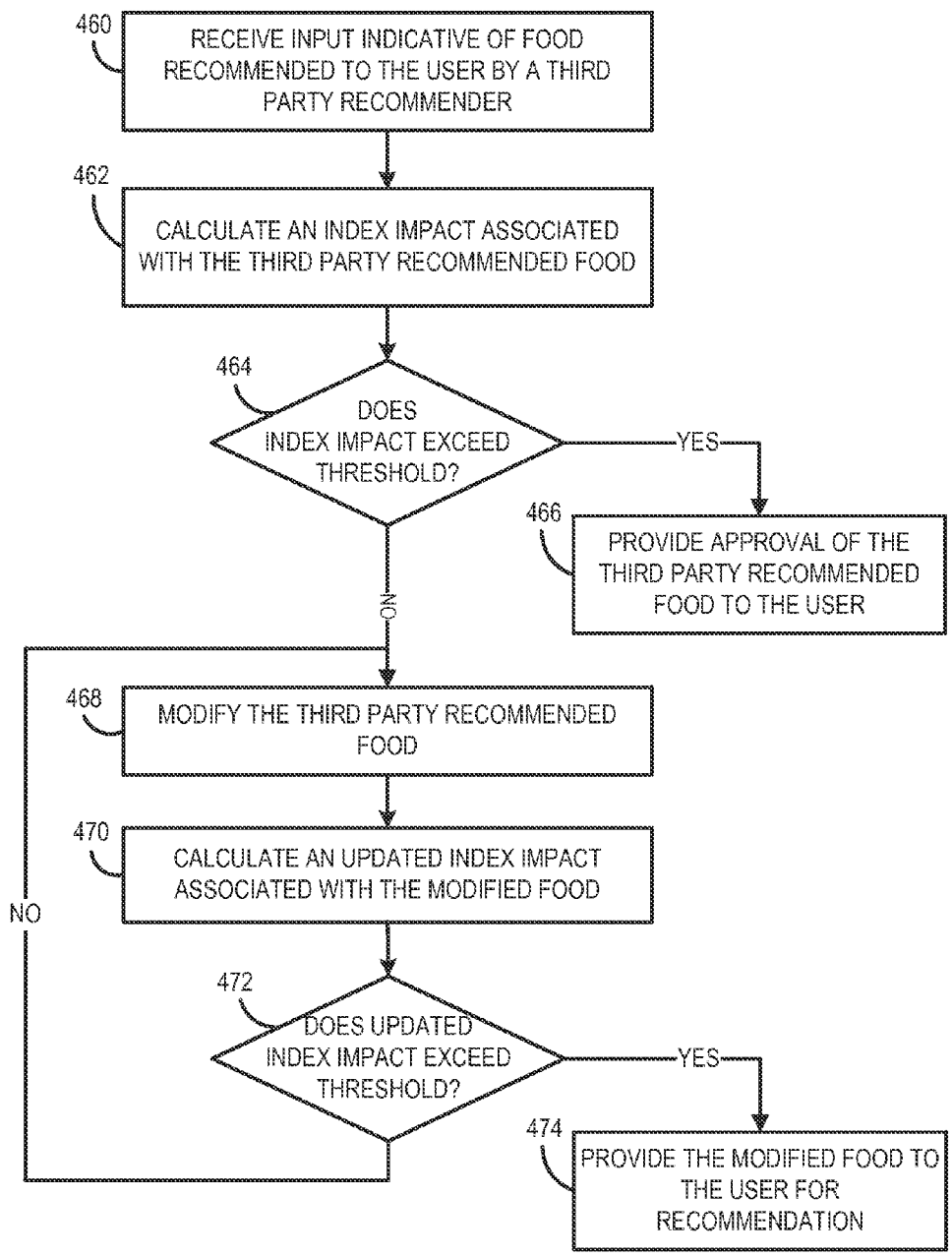
FIG. 5E is a flowchart of a method used by a computerized system to provide an assessment of a food recommendation by a third party for a person to consume, according to an illustrative implementation.

The method 340 of FIG. 5E may be used for assessing one or more foods that a third party recommender has suggested for consumption by the user. The third party recommendation may be based on a standardized meal program or a nutritional program customized for the user, and the recommended food(s) may include any number of ingredients, dishes, or meals. According to this aspect, the user can obtain an independent assessment of whether consuming the food recommended by the third party (in its original or modified form) would improve the alignment between the user's nutrient consumption and the user's desires goals. The assessment of the third party recommended foods may be provided in any suitable form, including as a numerical index impact, a score, a letter grade, or other symbol.

Process 340 begins at step 460, prior to which the user would have been suitably identified to the system via an authentication or other means. At step 460, the processor 105 receives an input indicative of one or more foods recommended to the user by the third party recommender. The input may be provided by the user or directly from the third party recommender (e.g., through a linked account for the user that permits the third party systems to share information about the user with the system 120). The shared information may include user data such as the user's goals, favorite foods, recently consumed foods, index, or any other suitable data related to the user. The recommended food(s) may be proprietary foods associated with the third party recommender, or meals specifically tailored to the user. The recommendation may be based on any information, such as the user's nutritional goals, demographic information, dietary restrictions, or any other suitable data.

At step 462, the processor 105 provides an assessment of the third party recommendation using any of the methods described herein. In this example, the processor 105 calculates an index impact associated with the third party recommended food. However, the processor 105 can also rate the food for its stand-alone nutritional value without reference to the user's historical nutrient consumption. As described above, the index impact associated with a food represents a change to the user's nutritional index if the food is consumed by the user and is computed based on a comparison between the user's target profile, the user's consumption profile, and a nutritional profile of the food. The nutritional profile of the food may be received at step 460 (from the user or from the third party recommender, for example), or the processor 105 may identify the nutritional profile of the food based on a list of ingredients in the food. A positive index impact indicates that if the user were to consume the food, the user's index would increase, thereby causing the user's consumption profile to approach the user's target profile. Similarly, a negative index impact indicates that consuming the food would cause the user's consumption profile to deviate from the target profile.

In some implementations, the user selects an option to only view a score associated with a food recommendation provided by the third party recommender. In this case, the method 340 may end at step 462, and the index impact associated with the third party recommended food is provided to the user. In other implementations, the user selects an option to determine whether the system 120 would also recommend the third party recommended food in its original or modified form. In this case, the method 340 continues past step 462 to determine whether to approve the food recommendation or to determine whether a modified version of the food recommendation is more appropriate.

At decision block 464, the processor 105 determines whether the index impact exceeds a threshold. The threshold may be a predetermined threshold (e.g., a change of 0.01 or more for an index that ranges from zero to one) or a dynamically determined threshold. For example, the processor 105 may compare the index impact of the third party recommended food to the index impacts of one or more other foods. The one or more foods may be candidate foods previously consumed by user or previously recommended to the user, and may include foods stored in the known foods database 106a and/or the consumed foods database 106b. In this case, the processor 105 may iterate over a set of candidate foods in a database and compare the food(s) with the highest index impact(s) to the index impact associated with the third party recommended food. If the index impact of the third party recommended food exceeds the threshold, the method 340 proceeds to step 466 to provide approval of the third party recommended food in its original form to the user.

Alternatively, if the processor 105 determines that the index impact calculated in step 462 does not exceed a threshold, the method 340 proceeds to step 468. At step 468, the processor 105 can recommend a modified version of the third party recommended food (e.g., by adjusting the serving size), or may recommend a different food altogether if such a modified version does not significantly improve the index. In an example, modifying the third party recommended food may include adjusting one or more portion sizes of the foods in the third party recommendation, removing one or more foods in the recommendation, or adding one or more foods to the recommendation. At step 470, the processor 105 calculates an updated index impact associated with the modified food.

At decision block 472, the processor 105 determines whether the updated index impact exceeds a threshold. The threshold used at decision block 472 may be the same as or different from the threshold used at decision block 464. As described above, the threshold may be a predetermined threshold or a dynamically determined threshold. If the index impact of the modified food exceeds the threshold, the method 340 proceeds to step 474 to provide recommendation of the modified food for consumption by the user. Otherwise, if the criterion in decision block 472 is not met, the processor 105 returns to the step 468 to modify the third party recommended food in another way. The steps 468, 470, and 472 may be repeated any number of times until a modified version of the third party recommended food is identified that is appropriate for recommendation. Alternatively, a threshold may be set such that if the steps 468, 470, and 472 are repeated the threshold number of times, without having found an appropriate modified version for recommendation, an output may be provided to the user indicating that the third party recommended food is not suitable for consumption, and/or that no modified version of the third party recommended food was found to be suitable.

The steps of the method 340 are in the shown order for illustrative purposes only, and one of ordinary skill in the art will understand that any step may be omitted, the order of the steps may be modified, or any steps may be performed simultaneously, without departing from the disclosure.

Figure 5F:
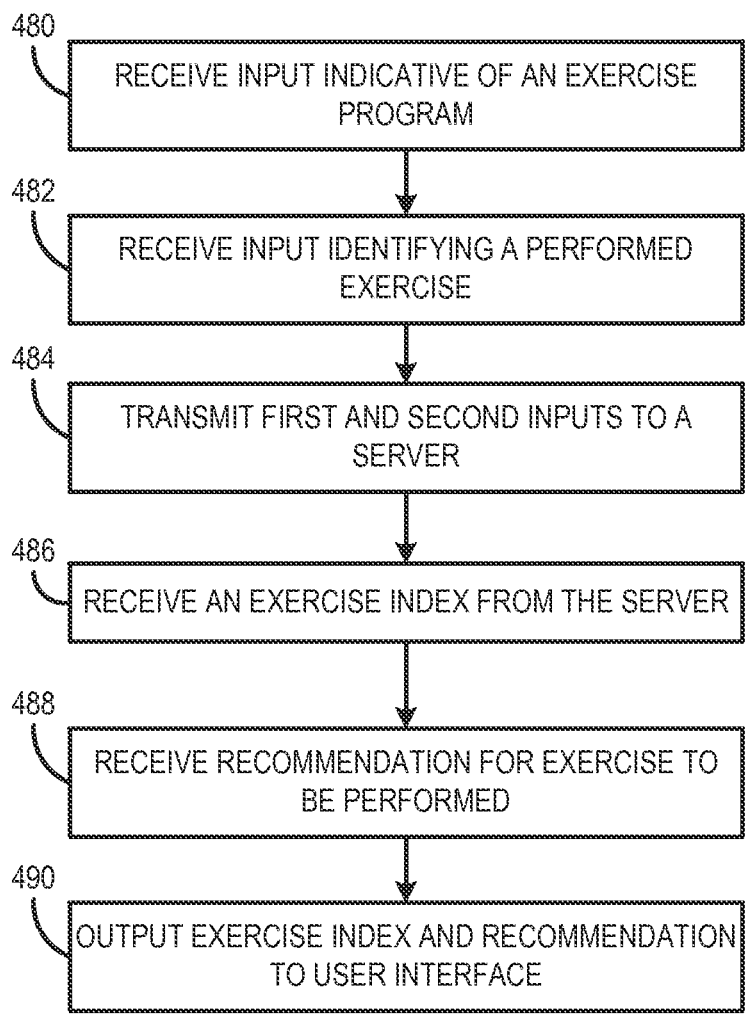
FIG. 5F is a flowchart of a method used by a computerized system to provide an assessment of a person's exercise regimen, according to an illustrative implementation.

FIG. 5F is a flowchart of a method 350 that may be implemented by the system 100 to modulate a person's exercise regimen with specific exercise needs. In general, the method 350 provides an analysis of an exercise program performed by the user in comparison to target levels of exercise recommended for or specified by the user, according to the user's health-related goals. Determining an exercise recommendation may include determining an exercise index representative of an alignment between the user's exercise regimen and the user's exercise goals. In this case, the exercise index may be computed as a weighted sum of deviations between the user's target exercise levels and the user's performed exercise levels. Identifying an exercise suitable for recommendation may include determining modified target exercise levels by subtracting previously performed exercise levels from the user's original target exercise levels. Exercises may be iteratively considered from a database of exercises, and data associated with each exercise may be compared to the modified target exercise levels to identify an exercise that, if performed by the user, would bring the user's exercise regimen in better alignment with the user's goals. As an example, the exercises in the database may be each associated with different types of data, such as a type of exercise (e.g., swimming, running, playing a sport such as baseball or basketball, walking, climbing stairs, yoga, pilates, calisthenics, etc.), an intensity level of the exercise (e.g., low level, medium level, high level), a number of calories burnt per unit time (which may be different for different users, depending on the user's weight and height, for example), or any other suitable data associated with exercise. This data may be provided by the user over the user interface 112, for example. Each exercise associated with a different type or intensity level may be associated with a target exercise level specific for the person, and the exercise index may be computed based on a deviation between the performed exercise levels and the target exercise levels for each exercise of a different type or intensity level.

As shown, the method 350 generally includes the steps of receiving an input indicative of an exercise program and an input identifying a performed exercise. The exercise program may be selected by the user from a plurality of exercise programs, or by the system 100 from the plurality of exercise programs based on user-specific information (such as a medical condition, an exercise goal, a weight goal, etc.). In certain implementations, the inputs are received at the user interface 112, with the first input indicating a exercise program selected from a menu (step 480) and the second input identifying a performed exercise (step 482). The method further includes transmitting one or both inputs to the server 104 (step 484) and, in response, receiving an exercise index from the server 104 (step 486). The exercise index is calculated by identifying a deviation between the amounts of performed exercise and target amounts. The processor 110 also receives from the server 104 a recommendation for an exercise to be performed (step 488), and then outputs the exercise index and the recommendation to the user interface 112 (step 490). The steps of the method 350 may be performed in any suitable order, and may be performed simultaneously, in reverse order, or have some steps omitted. For example, the step of receiving an exercise index from the server (step 486) may be omitted such that at step 490, the method 350 outputs a recommendation without an exercise index. Similarly, the step of receiving a recommendation (step 488) may be omitted so that at step 490, the method 350 outputs an only exercise index.

At step 480, the user provides input indicative of an exercise program, selected from a menu of exercise programs. The menu of exercise programs may include a variety of common exercise programs, such as circuit training, weightlifting, cardiovascular training, cross-training, martial arts, calisthenics, yoga, pilates, etc. An exercise program may also include a range of intensity levels and recommended durations. In addition, the user can also provide other health-related goals, constraints or comments to the user interface 112. For example, the user may input in a free-form answer field certain exercise preferences, constraints, or injuries.

At step 482, the processor 105 receives an input identifying a performed exercise from the user. For example, the input may include a description of the exercise, an activity level associated with the exercise, and a length of time that the exercise was performed. An example set of displays that may be shown to the user on the user interface 112 for logging performed exercise is shown in FIGS. 31-32.

At step 484, the processor 105 transmits the first and second inputs to the server 104 over the network 102, and at step 486, the processor 105 receives (from the server 104 over the network 102) an exercise index calculated based on an alignment between a set of performed exercises associated with the user and the user's exercise program. The exercise index is preferably a single marker that represents, in a cumulative fashion, how far the user's exercise profile deviates from a target exercise profile derived from exercise program selected at step 480. In some implementations, a deviation from the user's target exercise level is calculated for each of a variety of exercises contained within the exercise program and then summed or further processed to provide the overall exercise index. A target exercise level is an amount or range of amounts of the specific exercise that a user desires to perform within a specified time period and is based on the selected exercise program. For example, target exercise levels may include three hours of medium intensity weight training a week, two hours of high intensity cardiovascular training a week, half an hour of low intensity cardiovascular training a day, one hour of yoga a week, etc. The specified time period may include any suitable time period, including a portion of a day, a day, a 5-day period, a 7-day period, etc. The target exercise levels may be compared to amounts of exercise performed by the user during the corresponding time periods to derive the exercise index.

At step 488, the processor 105 also receives (from the server 104 over the network 102) a recommendation for an exercise to be performed. Methods for determining the exercise recommendation may be similar to the methods for determining meal recommendations as described above, and may be based on minimizing a deviation between the user's target exercise levels and the user's performed exercise levels. In particular, the user may be associated with a set of favorite exercise, and an appropriate exercise may be selected from this set for recommendation to better align the user's exercise levels to the user's goals. In an example, the exercise recommendation may be an exercise not previously performed by the user, but may be selected based on similarity to other types of exercise that the user enjoys or availability of exercise classes or equipment near the user. In particular, the recommended exercise may be based on one or more constraints. In an example, to ensure that the user gets a variety of different types of exercise, the recommended exercise may be restricted to be of an exercise type that the user has not performed in the last day, week, month, or any other suitable time period. At step 490, the processor 105 outputs the exercise index and the recommendation to the user interface 112 for display to the user.

The method 350 is described in relation to determining an exercise index and identifying an exercise recommendation for the user. The nutritional index described in relation to FIGS. 3-5E is generally representative of an alignment between the target nutrient levels and actual consumed nutrient levels for the user. Moreover, other indices may be similarly calculated, such as a sleep adherence index, a weight index, a medication adherence index, or a wellness index that combines two or more of the indices described herein. The sleep index may indicate an alignment between target levels of sleep and actual amounts of sleep for a user. Similarly, the weight index may indicate an alignment between a target weight and an actual weight for a user, and the medication adherence index may indicate an alignment between target times and amounts of medication and actual times and amounts for the user. In general, any other index associated with the user's health may be computed, the index being representative of an alignment between a goal and the user's actual behavior. Any number of the indexes described herein may be then combined to derive a general wellness index. For example, the indexes may each be assigned a weight, and the weighted indexes may be summed to derive the aggregate index. The general wellness index may then be used to indicate an overall wellness of the user and can indicate any number of factors contributing to the user's health, such as the user's diet, exercise regimen, sleep, medication adherence, and/or weight.

In some implementations, one or more of the components of the systems of FIGS. 1A-1C are used in a system for purchasing items at a grocery store. In particular, the known foods database 106A may include a list of food items from the grocery store and the corresponding nutritional content of the food items. The systems and methods described herein may be used to recommend one or more items from the grocery store for the user to purchase. As an example, upon entering the grocery store, the user device 108 may display a list of food items specifically recommended for the user and available for purchase at the grocery store. The user device 108 may be equipped with GPS technology such that the user device 108 receives a signal when the user enters a grocery store, for example. The list may be sorted according to a calculated index impact associated with each food item, such that the items with the most positive index impacts are displayed near the top of the screen of the user device 108. In addition, the process for identifying the recommended food items may include applying constraints, such as the cost of each food item, what food items are discounted at the grocery store, what food items the user may have at home, a number of people the user is shopping for, other special requests or any other suitable constraint for identifying a food item for recommendation to a user. As an example, the systems described herein may receive information from the grocery store such that coupons or discount codes may be provided to the user for the user's recommended food items. In some implementations, the user device 108 is equipped with GPS technology such that the user device 108 is configured to automatically display the food item recommendations without requiring the user to enter the grocery store's information.

In some implementations, the user device 108 is configured to scan a bar code of a product. For example, a user may use the barcode scanner to indicate that the user has consumed or plans to consume a food product associated with the bar code. Using the barcode scanner allows for efficient logging of food entries because it avoids the need for the user to search through a list of foods to locate the consumed food. Barcode scanning also avoids the need for the user to enter a time or date that the food was consumed because the time of scanning may be used a default time (though the user may later update the time and/or date of the entry). Instead, the user may use a mobile device to quickly scan the barcode, and the system 120 may use the barcode data to quickly locate the scanned item in a database. In particular, the database may be sorted according to barcode identifiers to make locating the scanned item more efficient. Alternatively, the user may use the bar code scanner to indicate that the user is considering purchasing the product. In this case, upon scanning the bar code of the food product, the user device 108 may display an index impact for the user if the user consumes an amount of the food product. A default setting on the user device 108 may be to assume that the user would consume one serving of the food product to determine the index impact for one serving (though the user may also update the number of servings if the user desires to see the index impact for a different amount of the food product). Similarly, the user device 108 may display an index impact for another consumer (such as the shopper's child or other family member, for example), so that an effect of consuming the food product is displayed to the shopper to help the shopper decide whether to purchase the product.

In some implementations, the server 104 keeps track of food products in the user's home. In this case, the server 104 may maintain an electronic database of food data corresponding to an inventory of food products in the user's possession. This database may be updated appropriately when the user or someone else consumes the user's food products, and when the user purchase food products. In some implementations, the recommendation systems described herein provide one or more food or meal recommendations based on the inventory of food products in the user's possession. By providing recommendations of foods or meals that the user already has in the user's home, the systems and methods described herein provide an efficient way for the user to make use of the ingredients he or she already has, while aligning the user's diet with his or her dietary goals.

In some implementations, the system 120 provides test or simulation cases to provide the user with a preview of changes to the user's health or physiology that may result from meeting the goals. In one example, the user interface 112 displays a picture or a diagram of the user that depicts changes to the user's physique as the user follows an exercise and/or nutritional program using the assessments provided herein. The user may provide a picture of the user's body or physical measurements (with or without other physiological data such as blood pressure, glucose levels, and cholesterol levels). The system 120 may then generate an image or other indicator based on predicted improvements to the user's physique or other physiological parameters as the user's nutritional index improves. Using this simulator, the user may be able to determine in advance (or after the user has began following the program) if the selected dietary program or other goal results in improvements to the simulated parameter(s). Thus, as the user's index changes, the system 120 may update the diagram of the user to reflect any predicted changes to the user's body.

Figure 5G:
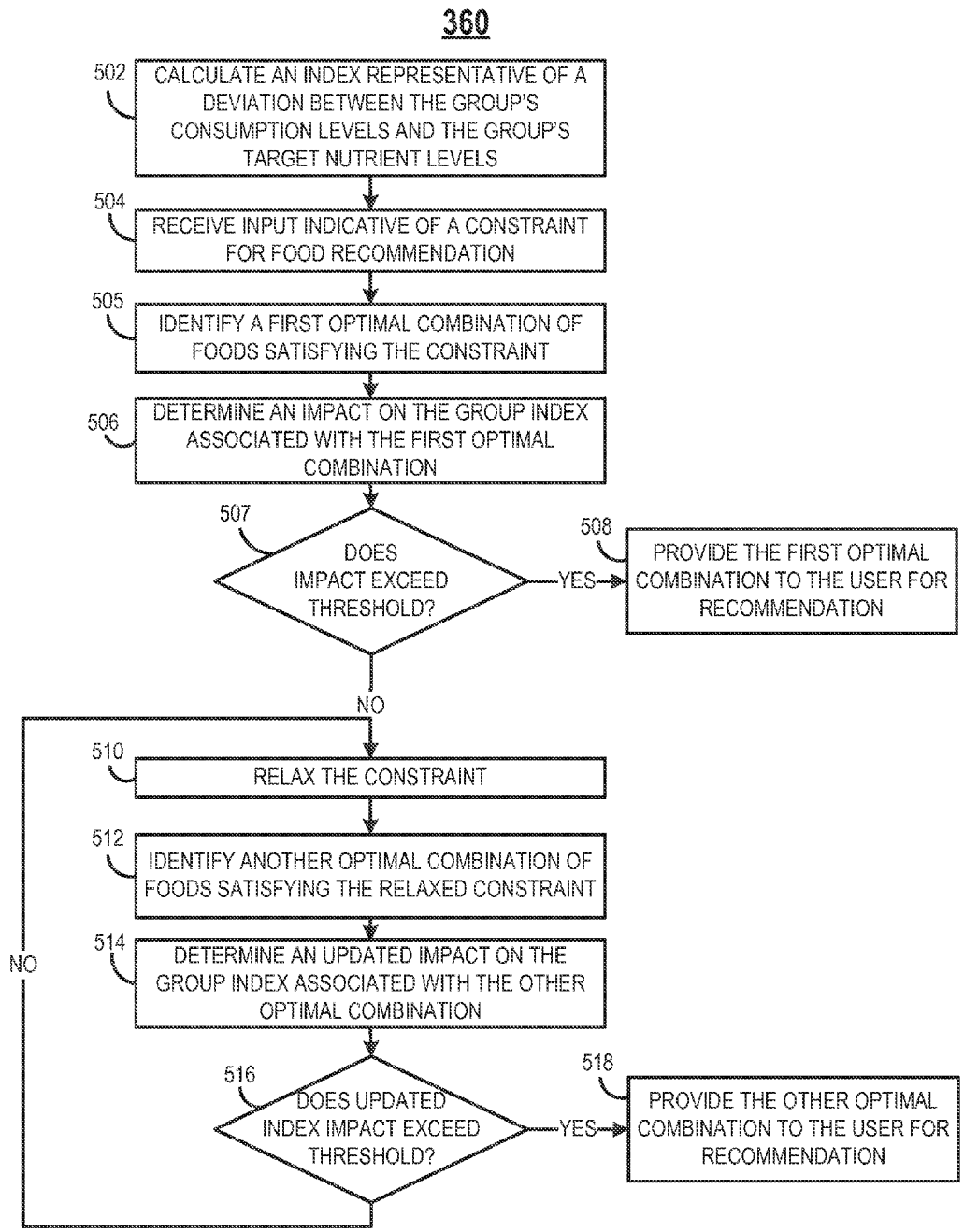
FIG. 5G is a flowchart of a method used by a computerized system to provide a food recommendation for a group of individuals, according to an illustrative implementation.

In some implementations, it may be desirable to assess and/or recommend meals to a group of people that improves the alignment of each individual's nutrition intake with the individual's health goal(s) while ensuring manageable number of separate meals. For example, in a family that includes both parents, grandparents and several children, it is particularly convenient if a minimum number of separate meals can be shared while meeting the nutritional goals and tastes of the individual members. FIG. 5G is a flowchart of a method 360 that may be implemented by the system 100 to modulate a group's diet with the specific nutritional needs of the group. In general, the method 360 provides an analysis of a diet consumed by individuals in the group and compares the consumed diet to target levels of nutrients recommended for the group members. The method 360 may be used to generate an aggregate assessment of the group's diet in relation to nutritional goals specified for the group. In addition, the method 360 may also be used to generate one or more recommendations for one or more foods to be consumed by the members in the group.

In an example, the group includes members of a household, and the user is a head of the household who provides for one or more other members of the group. As another example, the user may be a meal planner for a cafeteria in a school or in an office building. In group-based meal recommendation, the optimization processes described herein are performed to minimize an aggregate deviation between the population's diet and the population's dietary goals. Furthermore, in an example, when the members are a family, the optimization process for the meal recommendation for the adult(s) in the family may be performed separately from the optimization process for the children, such that one meal including a set of food(s) may be recommended to be consumed by the adult(s) while a different meal including a different set of food(s) may be recommended to be consumed by the children. In addition, the group-based meal recommendation process may take into account special dietary restrictions such as certain allergies or preferred (or non-preferred) foods specified by members of the population. The result of the group-based meal recommendation may include one or more food items recommended for all members to consume, and/or one or more custom variations of the food items recommended for specific members to consume.

At step 502, the processor 105 calculates an index representative of a deviation between the group's consumption levels and the group's target nutrient levels. In this case, the index is a group index indicative of an aggregate deviation between the group's diet and the group's nutritional goals. In particular, the calculation of the index may be based on previously received inputs including a set of foods previously consumed by the members of the group and one or more dietary programs or nutritional goals selected for the group members. In this case, each member of the group may be associated with a consumption profile (based on a set of foods previously consumed) and a target nutritional profile specific to the member. The set of nutrients used in the consumption and/or target nutritional profile of one member may be identical to or different from that of another member of the same group. In an example, one or more individuals in the group may be assigned a priority weight. The priority weight may be representative of a relative importance of the nutritional goals of the individual compared to those of the other group members. For example, when the group is a family, a child's nutritional goals or needs may have priority over a father's nutritional goals. In this case, the child may be assigned a numeric priority weight that is larger than the priority weight of the father, such that the optimization process results in a food or meal recommendation that may be more optimal for the child than for the father. In an example, the weights $w_n$ used to weight the deviations between target levels and consumed levels may be determined based on the priority weight for each individual in the group. In particular, the applied weights may be scaled by a number associated with the priority weight. For example, if the child is assigned a priority weight of 3, and the father is assigned a priority weight of 1, the weights applied to the deviations between the child's target nutrient levels and consumed nutrient levels may be on average three times the weights applied to the father's. Because the child's nutritional needs are assigned with more weight than the father's, the recommendation resulting from the optimization process described below are more likely to meet the child's nutritional needs than to meet the father's nutritional needs.

In addition, certain nutrients may be assigned different priority weights for different individuals in the group. For example, it may be important for a mother to consume a certain amount of a nutrient (such as vitamin K). In particular, the user may specify that the mother's requirement for vitamin K is four times as important as the child's need for vitamin K. In this case, the weight applied to the mother's deviation between the target level of vitamin K and consumed level of vitamin K may be scaled four times more than the weight applied to the child's deviation. By allowing for individuals to have global priority weights as well as nutrient specific priority weights, the system 120 allows for the user to customize the optimization process to best meet the needs and goals of the members of a group.

At step 504, the processor 105 receives an input indicative of a constraint for the group-based food recommendation. As an example, it may be desirable to identify the minimum number of dishes or food products that will meet the nutritional needs and goals of the members of the group. In this case, the user (a head of household or meal planner for a cafeteria or restaurant, for example) may provide a constraint such as an amount of time that is available for food preparation, or a target number or maximum number of dishes that should be included in the recommendation. While it may be ideal for each member of the group to have a meal that optimally meets the individual's specific needs, it may also be desirable to have the members of the group consume one or more of the same foods to reduce the meal preparation complexity and time. In this case, while the recommended foods may not be the optimal food for each member of the group, the group's general nutritional needs may still be met while considering the convenience and feasibility of the meal preparation. In an example, when the group includes a small family, it may be desirable to recommend a single dish including one meat, one carbohydrate, and one vegetable. Thus, the user (or the head of the household) may provide input at step 504 indicating that the desired constraint is to view a recommendation including one meat, one carbohydrate, and one vegetable.

Each individual in the group may be associated with a consumption profile and a target profile, which may be compared to each other to form a deviation profile. In some implementations, the processor 105 detects an incompatibility between two or more deviation profiles of members in the same group. As an example, one member of the group may have a strong preference to consume peanuts, while another member may be allergic to peanuts. In this case, a minimum number of distinct foods, meals, or ingredients may be used as a constraint, such that the incompatibility between the two members can be resolved by allowing for different foods to be recommended to the different members.

At step 505, the processor 105 identifies a first optimal combination of foods satisfying the constraint. In particular, the optimization process described herein may be performed by iterating over various combinations of foods, computing a predicted impact on the group index with each combination, and selecting an optimal combination. In some implementations, any combination that includes prohibited foods or ingredients for one or more members of the group (such as any allergies or other dietary restrictions) may be automatically eliminated from consideration.

In an example, for a candidate combination of foods, the processor 105 computes an index impact specific to each member of the group. In this case, for each member of the group, a deviation profile may be generated based on a comparison between the member's consumption profile and the member's target nutritional profile. The deviation profile may be used to determine an individual index impact associated with each member of the group. An aggregate deviation (or an aggregate index impact) may be formed by weighting the individual index impacts of the members (by the priority weights of the members, for example) and combining the weighted impacts. The aggregate deviation may thus reflect a relative importance of the deviation profiles in accordance with the priority weights of the members. The aggregate deviation for each candidate combination may be compared to the other aggregate deviations of other candidate combinations, and the combination with an aggregate deviation exceeding a threshold may be selected. In an example, the threshold may be specified such that the candidate combination with the minimal aggregate deviation is selected.

In another example, an optimal combination may be identified for each member of the group. In this case, the optimal combination may correspond to the combination that results in a maximal index impact for the individual. When each member's individual optimal combination is identified (resulting in N individual optimal combinations for M members in a group, where N may be less than M if at least two members of the group have the same individual optimal combination), an individual index impact may be computed for each individual optimal combination for each member (resulting in N×M individual index impacts). For each individual optimal combination, the corresponding individual index impacts may be weighted (by the priority weights of the members, for example) and combined to determining an aggregate index impact.

As an example, the optimal combination may be the combination with the maximum predicted impact, or the optimal combination may be the first combination with a predicted impact that exceeds a predetermined threshold. In an example, the predetermined threshold may be provided by the user. For example, the predetermined threshold may be set to zero such that any combination with a positive index impact may be appropriate for recommendation. In another example, the threshold may include a number of individual thresholds associated with each member of the group. In this case, using individual thresholds may be desirable to ensure that no member's individual nutritional index will decrease by more than a fixed amount after consuming the meal. Furthermore, the individual thresholds may be set independently from one another. For example, it may be desirable to specify that the child's individual nutritional index should not decrease at all, while it is acceptable for the father's nutritional index to decrease by at most one point. At step 506, the predicted impact on the group index associated with the first optimal combination of foods is determined.

The recommendation for a combination of one or more foods to be consumed by the group may include a meal recommendation. In this case, the recommendation may include different portion sizes for the different members of the group. For example, the different portion sizes may include different relative serving sizes of various components of the meal, such as recommending six ounces of steak and three ounces of potatoes for one member and recommending four ounces of steak and four ounces of potatoes for another member. In another example, the different portion sizes may include the proportional serving sizes for the various members of the group, such as recommending six ounces of steak and three ounces of potatoes for one member and recommending four ounces of steak and two ounces of potatoes for another member. The examples described herein may be used individually or combined in any suitable fashion to identify a suitable recommendation of one or more foods for a group to consume. These approaches may also be applied to identify a suitable recommendation of one or more exercises for the group to perform.

At decision block 507, the processor 105 determines whether the impact exceeds a threshold. For example, the impact may be compared to a predetermined number indicative of a threshold, such that if the impact is greater than the threshold, the method 360 proceeds to step 508 to provide the first combination of foods to the user for recommendation. In some implementations, the user may provide user input indicating that only recommendations satisfying the constraint specified at step 504 will be considered. In this case, the method 360 may automatically proceed to step 508 after identifying the first combination of foods, and end after the first optimal combination is provided for recommendation.

In other implementations, the user may provide user input indicating that it would be acceptable to relax the constraint specified at step 504 if doing so would increase the group's aggregate index or the individual nutritional indexes. In this case, if the processor 105 determines at decision block 507 that the impact does not exceed the threshold, the method 360 proceeds to step 510 to relax the constraint. In an example, when the constraint is to view a recommendation including one meat, one carbohydrate, and one vegetable, relaxing the constraint may include any number of additional food products (e.g., to include two vegetables). By relaxing the constraint, the set of possible food combinations is considerably expanded such that it is likely that the processor 105 will identify another combination of foods that would give rise to a better impact than the impact associated with the first optimal combination. In general, relaxing the constraint may be performed in any number of ways, such as by including another food product, dish, or ingredient or by including a food that is associated with more complexity, higher cost, more preparation time, cost of ingredients, availability of ingredients, or any suitable combination thereof.

At step 512, the processor 105 identifies another optimal combination of foods satisfying the relaxed constraint. In particular, the optimization process is repeated with the relaxed constraint to identify the other optimal combination. As described in relation to step 505, the optimization process may be performed by iterating over various combinations of foods, computing a predicted impact on the group index with each combination, and selecting an optimal combination. The same parameters (such as the thresholds, set of foods, whether individual nutritional indexes are considered, etc.) may be used for the optimization process at step 512 as at step 505, or the parameters may be different. At step 514, an updated impact on the group index associated with the other optimal combination of foods is determined.

At decision block 516, the processor 105 determines whether the updated impact exceeds a threshold. For example, the updated impact may be compared to a predetermined number such that if the impact is greater than the threshold, the method 360 proceeds to step 518 to provide the other combination of foods to the user for recommendation. The threshold used at the decision block 516 may be the same or different from the threshold used at the decision block 507.

In some implementations, the user may provide user input indicating specified levels of acceptable constraints and relaxed constraints. For example, the user may provide an input indicating that one dish including one meat, one carbohydrate, and one vegetable is preferred, but if such a dish does not meet certain nutritional requirements, the user will so also consider a dish including one meat, one carbohydrate, and two vegetables. If such a dish again does not meet certain nutritional requirements, the user may be willing to consider a dish including one meat, two carbohydrates, and two vegetables, for example. In general, the user may specify any number of levels of constraints, such that if the optimization process fails to identify a suitable combination of foods satisfying one level of constraints, the system 120 may relax the constraints a specified number of times to identify a combination of foods appropriate for recommendation. Thus, if, at decision block 516, the processor 105 determines that the updated index impact does not exceed a threshold, the method 360 returns to step 510 to further relax the constraint and repeat the optimization process with the further relaxed constraint.

By initially identifying a meal recommendation satisfying a constraint, and then later relaxing the constraint to include other types of meal recommendations, the systems and methods described herein allow for multiple levels of meal recommendation, with each level possibly increasing in preparation time and/or complexity. In general, one of ordinary skill in the art will understand that the systems and methods described herein may be applied to any number of levels, and the optimization process may be repeated any number of times to suit the group's needs.

Figure 6:
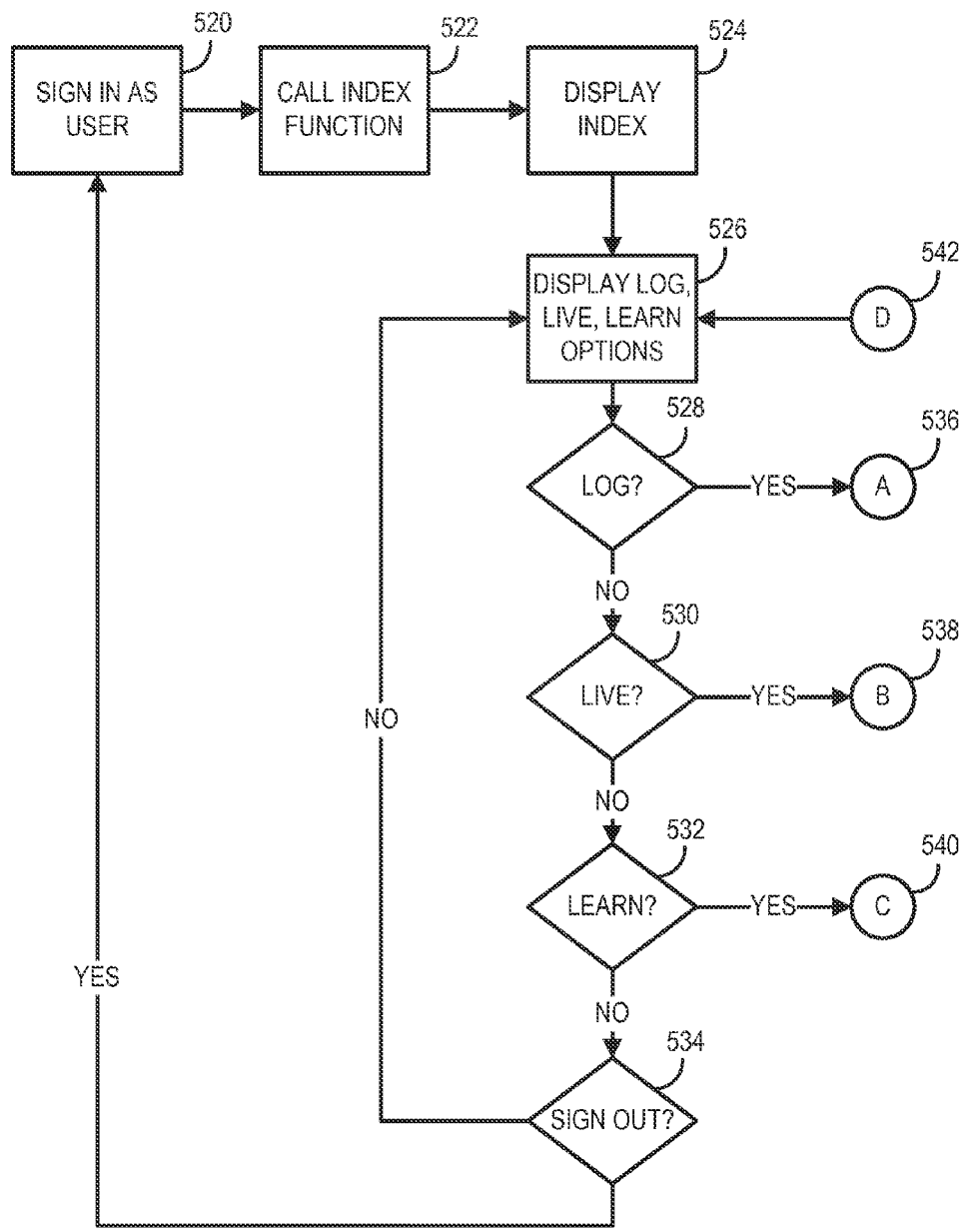
FIG. 6 is a flowchart of a method used by a computerized system to display objects on a display of a user interface, according to an illustrative implementation.
Figure 14:
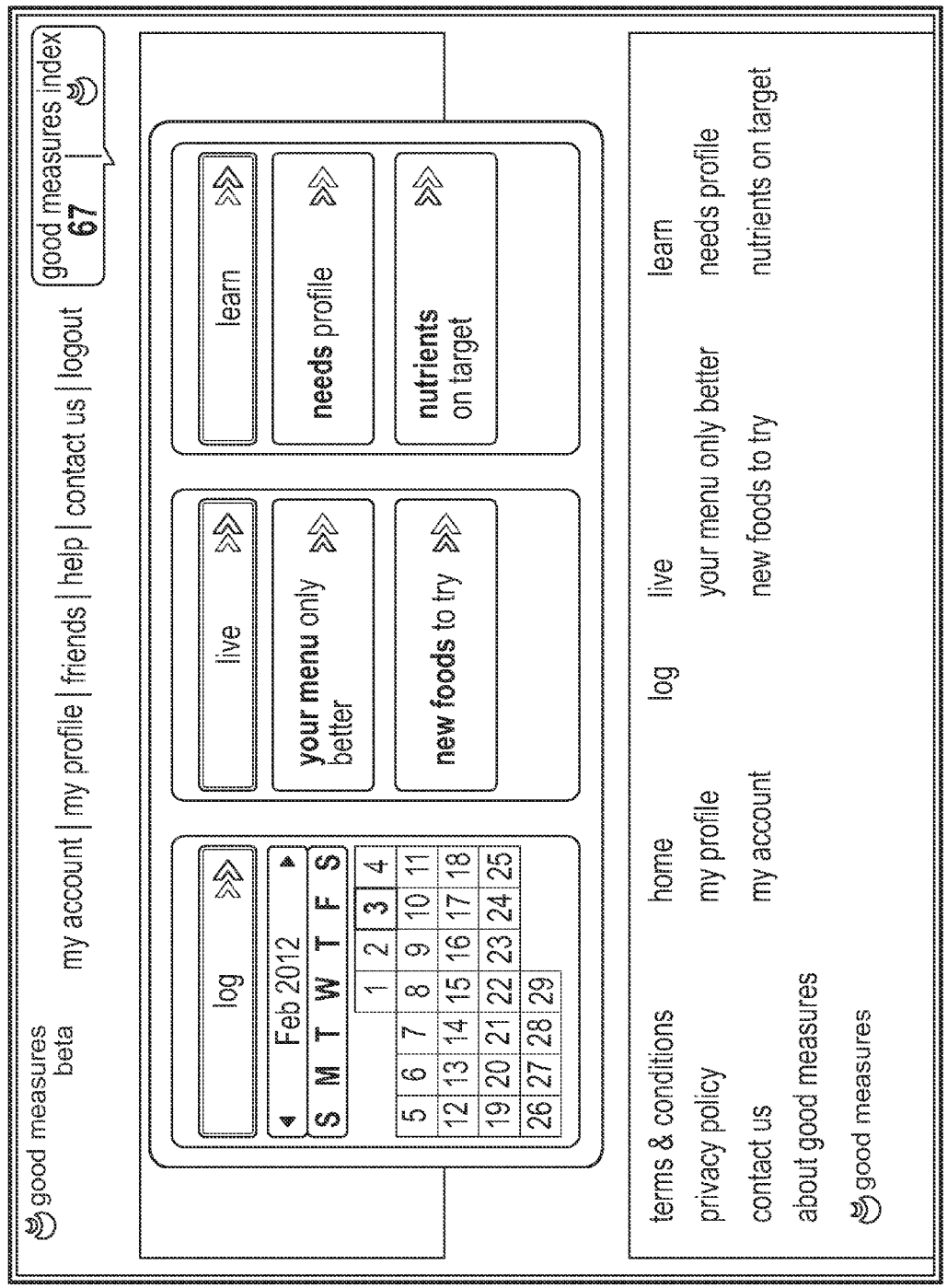
FIG. 14 is an example display of a home screen, according to an illustrative implementation.

FIG. 6 is a flowchart of a method 600 used by the processor 105 to display objects on the display of the user interface 112, according to an illustrative implementation. The method includes the steps of displaying a sign in screen, where a user signs in (step 520), calling an index function (step 522), and displaying the index (step 524). The method further includes displaying a home screen including "log," "live," and "learn" navigation options (step 526, discussed in detail below), a home screen for the log option (decision block 528 and step 536), a home screen for the live option (decision block 530 and step 538), and a home screen for the learn option (decision block 532 and step 540). The user can select to sign out (step 534). An example of the home screen is shown in FIG. 14.

Figure 7:
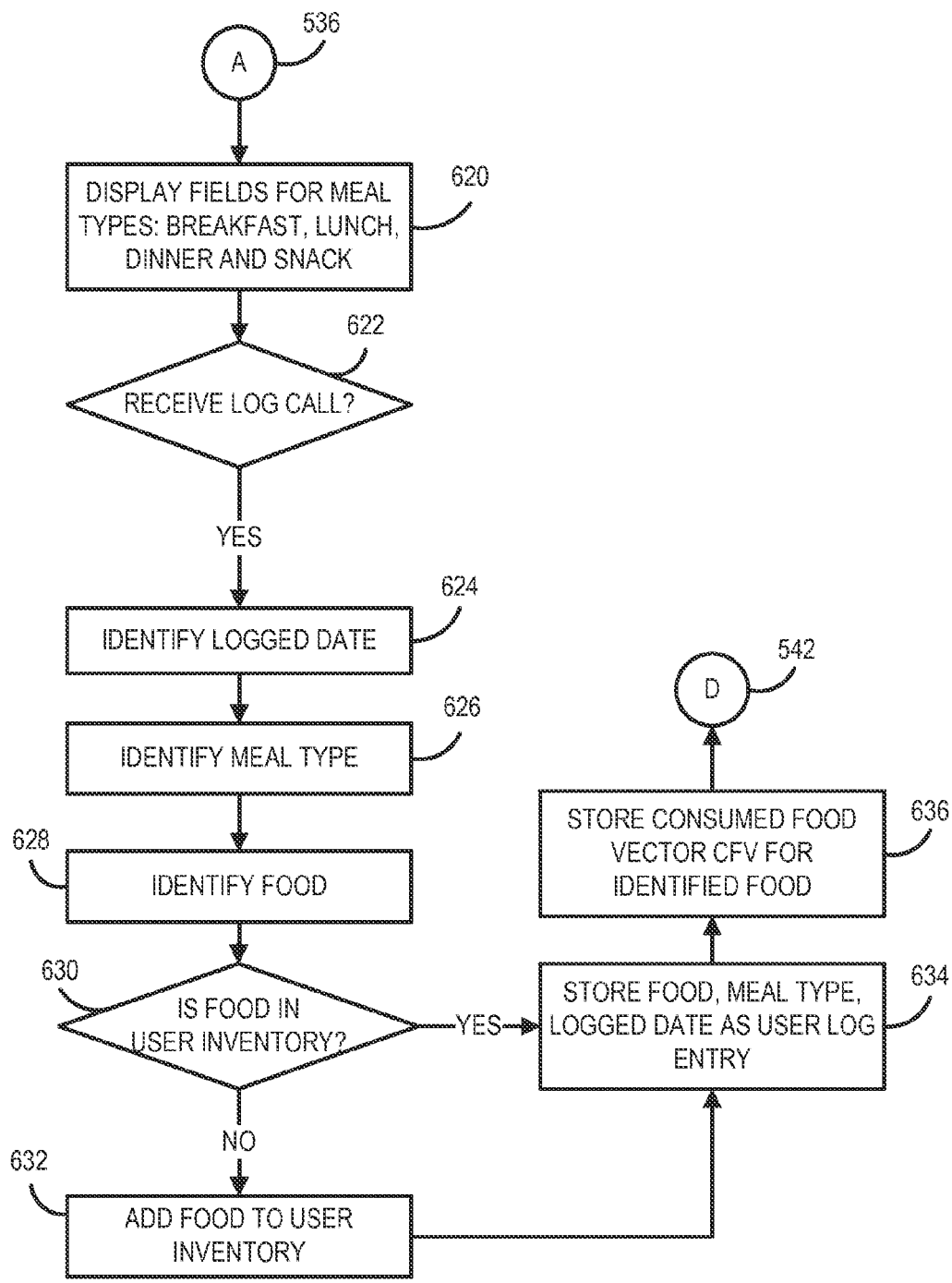
FIG. 7 is a flowchart of a method used by a computerized system to display options for logging consumed foods on a display of a user interface, according to an illustrative implementation.

FIG. 7 is a flowchart of a method 700 used by the processor 105 to display "log" options on the display of the user interface 112, according to an illustrative implementation. The method 700 begins with displaying the home screen for the log option including fields for different meal types such as breakfast, lunch, dinner, and snack (steps 536 and 620). An example of the home screen for the log option is shown in FIG. 23.

Figure 17:
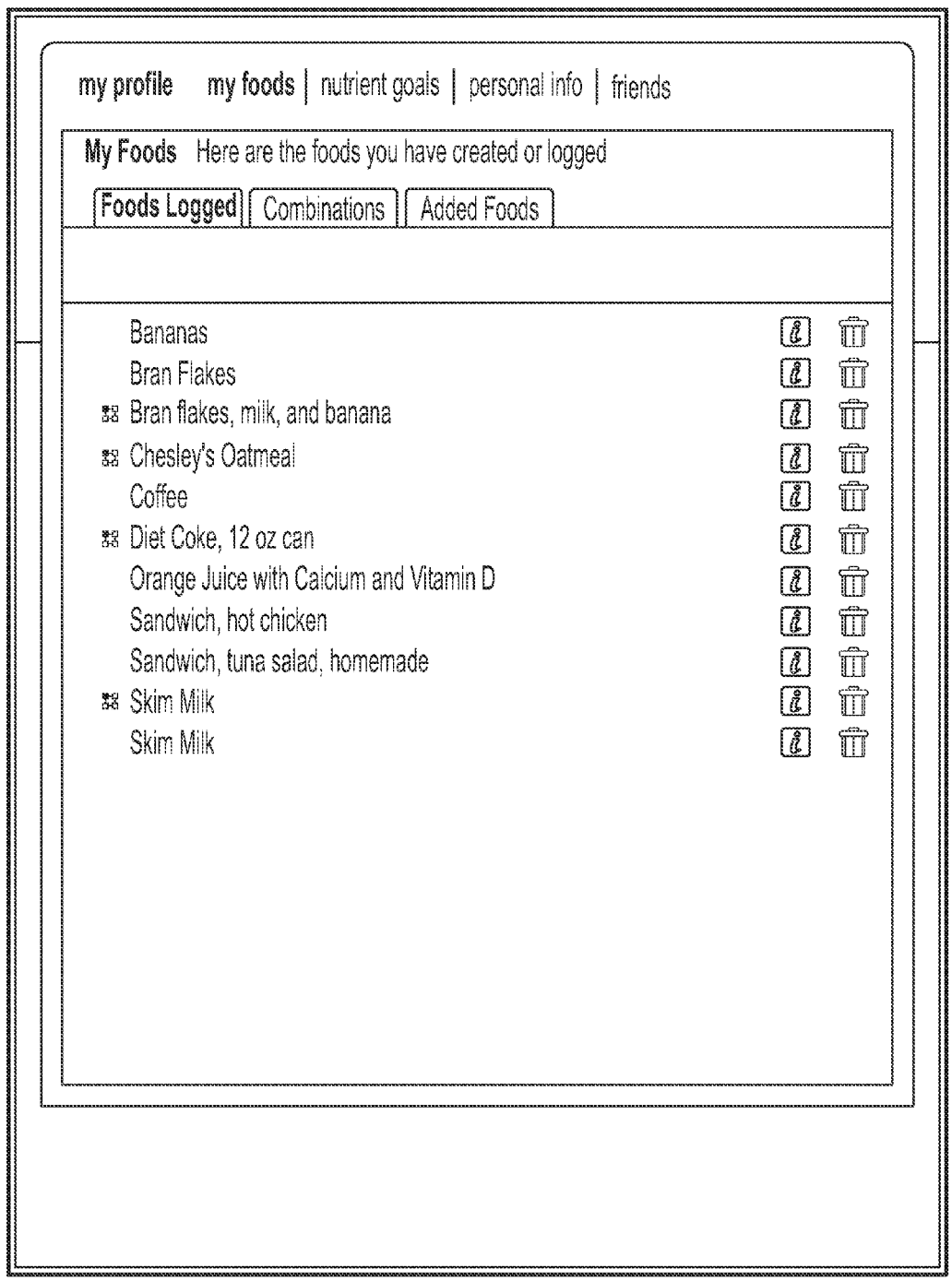
FIG. 17 is an example screen that displays a list of consumed and logged foods specific to the user, according to an illustrative implementation.
Figure 24:
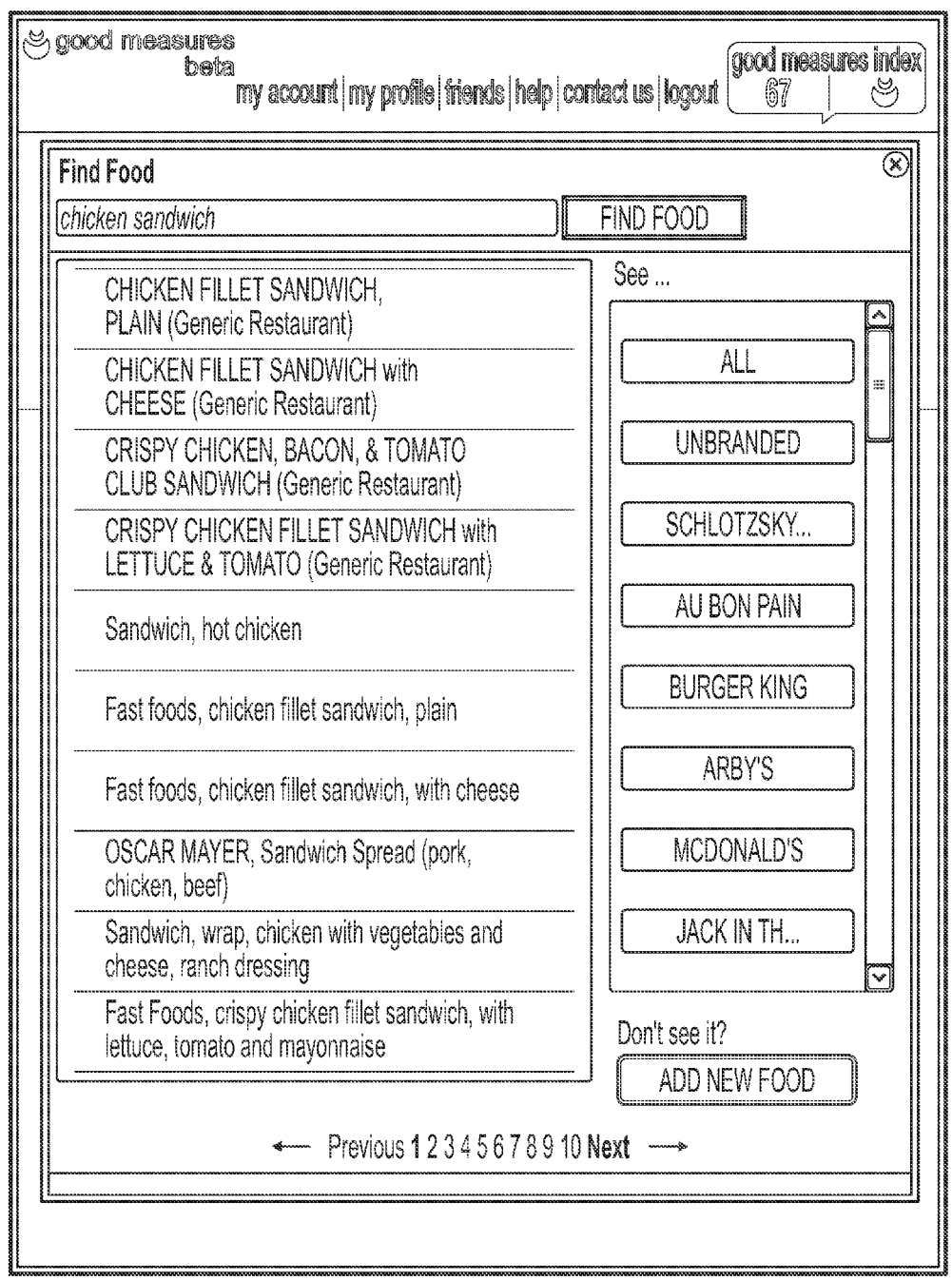
Figure 25:
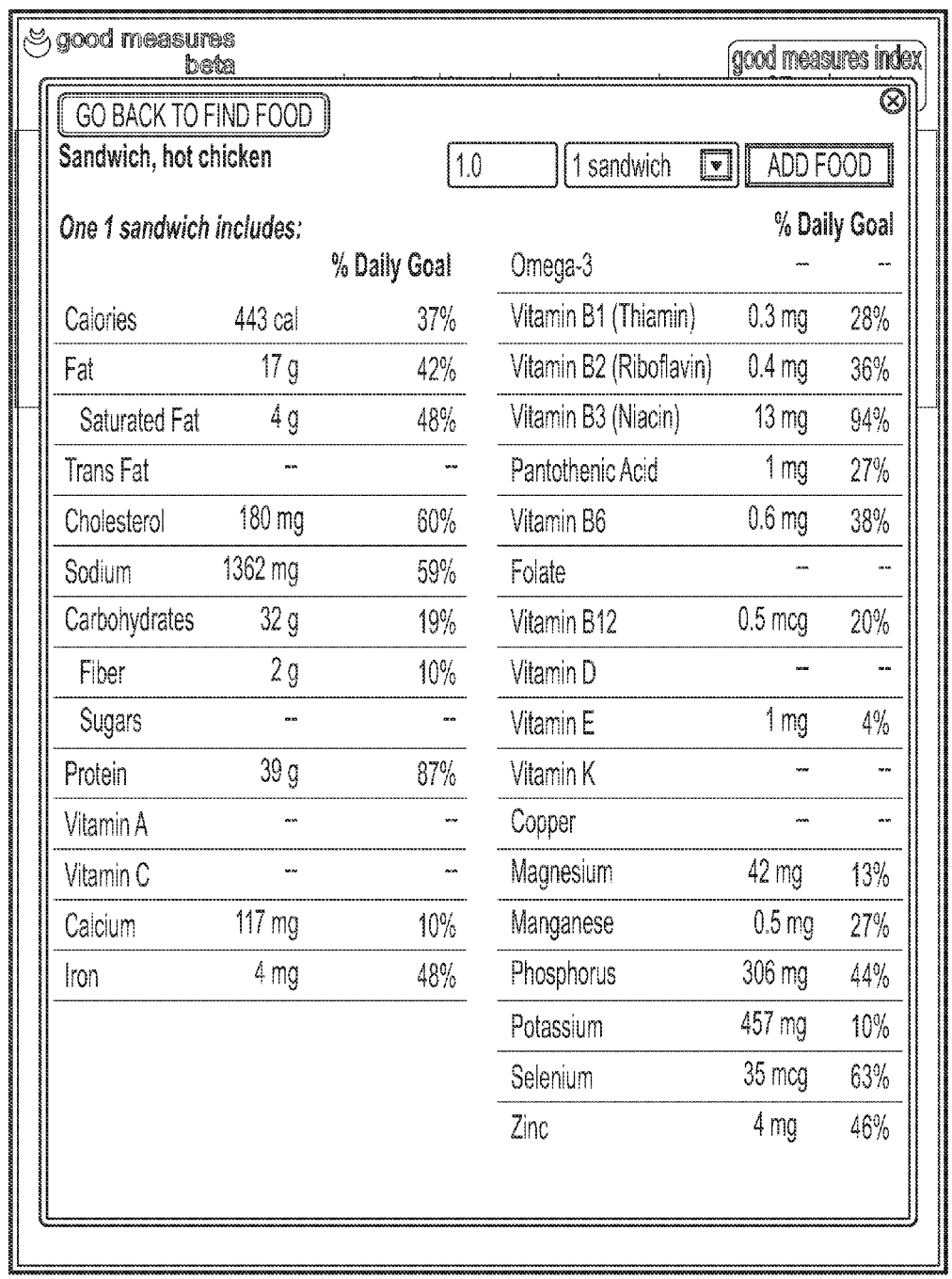

Referring back to FIG. 7, the processor 105 receives a log call, indicating that the user wishes to enter a consumed food to the user interface (step 622). The processor 105 then identifies the logged date, corresponding to the date that the user indicates the food was consumed (step 624) and identifies the meal type, which, in this implementation, is specified by the user when choosing which field to enter the food in FIG. 23 (step 626). When the user begins typing in the consumed food in the field, auto-fill entries appear on the display, and the user may select from one of the auto-fill entries. Alternatively, the user may search the database for the consumed food and select a food in the database. An example of a search screen with a query for "chicken sandwich" is shown in FIG. 24. The processor 105 identifies the food (step 628) and checks if the food is in the user inventory (step 630). The user inventory is a list of foods that the user has previously logged and may be stored on consumed foods database 106B in FIG. 1B. An example of a user inventory is shown in FIG. 17. If the food is not in the user inventory, the processor 105 adds the food to the user inventory (step 632). Otherwise, the processor 105 stores the food, meal type, and logged date as a user log entry (step 634) and stores a consumed food vector for the identified food (step 636). The consumed food vector corresponds to the contribution of various nutrients that the identified food makes to the user's consumption profile, and the elements of the consumed food vector correspond to the consumed nutrient levels as described earlier. An example consumed food vector for a hot chicken sandwich is shown in FIG. 25. Then the method returns to the home screen to display the log, live, and learn options (step 542).

Figure 8:
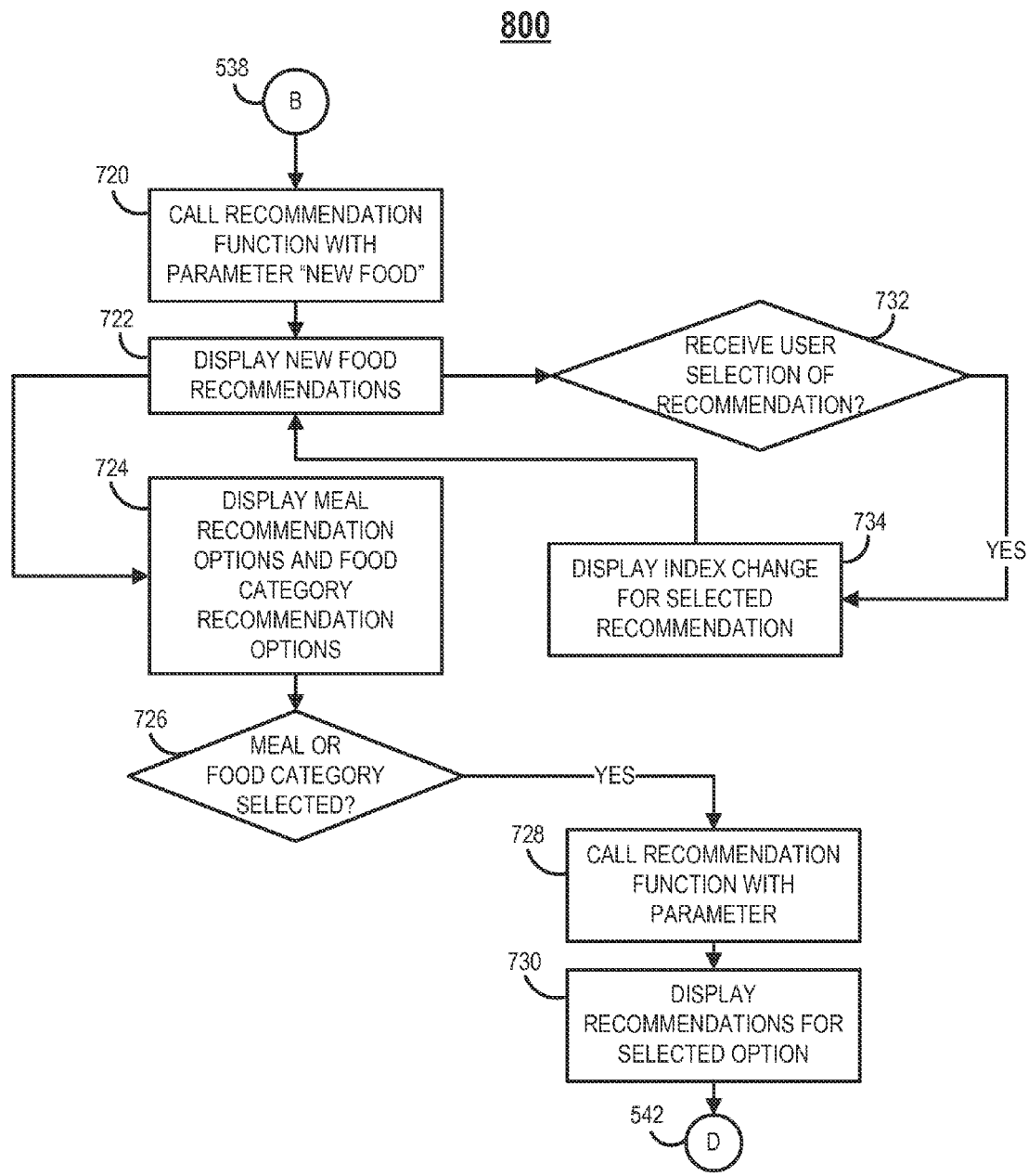
FIG. 8 is a flowchart of a method used by a computerized system to display a recommendation for a food to be consumed by a user on a display of a user interface, according to an illustrative implementation.

FIG. 8 is a flowchart of a method 800 used by the processor 105 to display "live" objects on the display of the user interface 112, according to an illustrative implementation. The method 800 begins with calling a recommendation function with a parameter, e.g., "new food" (step 720), that indicates to processor 105 that a food recommendation is requested. The processor 105 receives the new food recommendations from processor 105 and displays the new food recommendations (step 722). If a user selects a recommendation (step 732), then the index impact is displayed for the selected recommendation (step 734). The processor then displays meal recommendation options and food category recommendation options (step 724), and determines whether an optional meal type or food category is selected (step 726). If so, the processor 105 calls the recommendation function with a parameter corresponding to the selected meal type or food category (step 728) and displays the recommendations for the selected option (step 730) before returning to the home screen (step 542).

Figure 9:
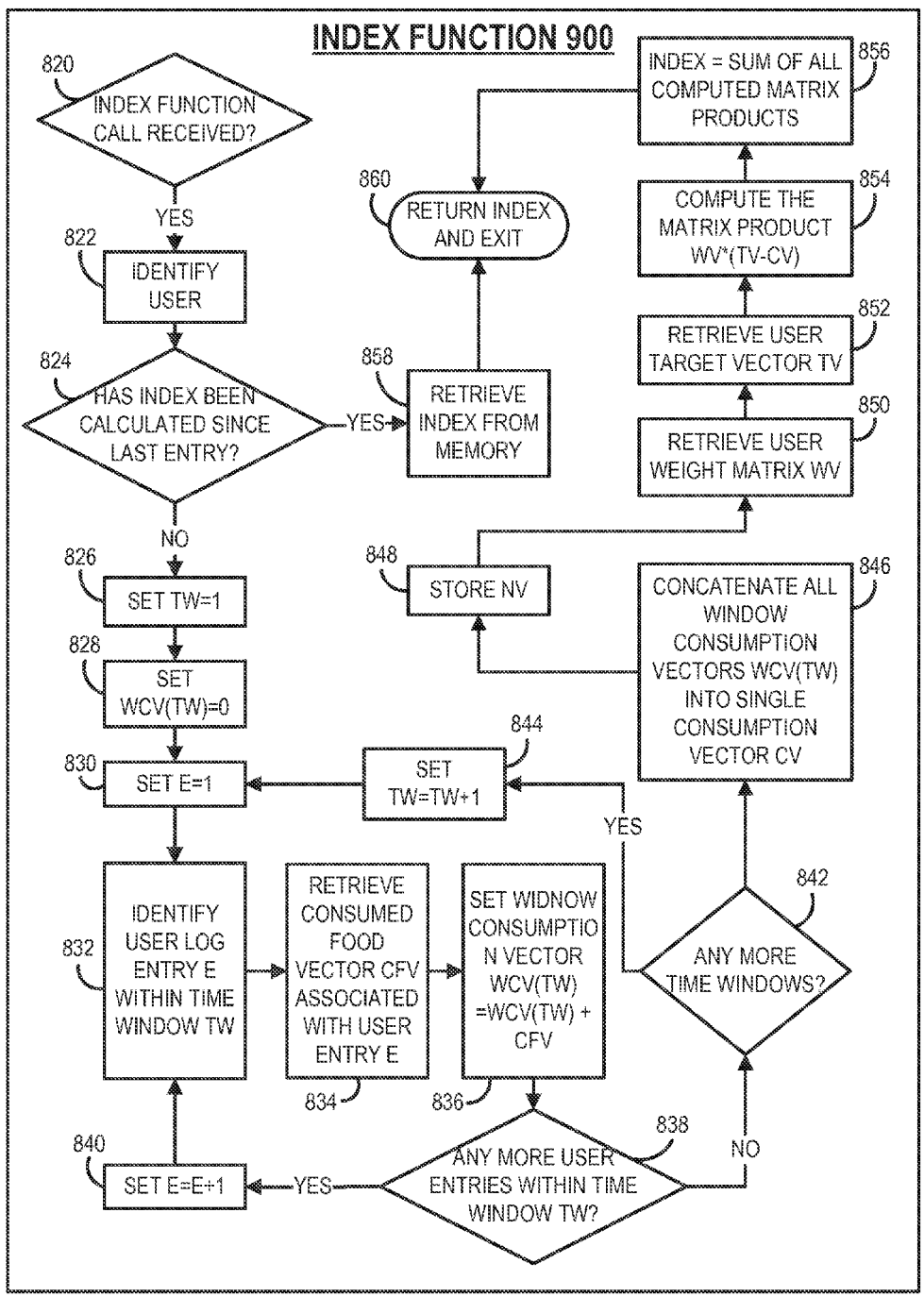
FIG. 9 is a flowchart of a method used by a computerized system to determine an index associated with an alignment between a user's consumed foods and the user's nutritional goals, according to an illustrative implementation.

FIG. 9 is a flowchart of a method 900 used by the processor 105 to compute an index function, according to an illustrative implementation. The method begins with receiving a call to the index function (step 820), identifying the user (step 822), and determining whether the index has been calculated since the last entry (decision block 824). If so, this means that the user has not created any entries corresponding to consumed foods since the last time the index was calculated, thereby precluding the need to update the index. In this case, the index is retrieved from memory (step 858) and returned before exiting (step 860). If the index has not been calculated since the last entry, the method proceeds to initialize to 1 a time window parameter (corresponding to a period of time since the last time the index was calculated to the present time) (step 826), initialize a window consumption vector (step 828), and initialize the index representing the number E of user log entries since the last time the index was calculated to 1 (step 830).

The processor 105 then identifies a user log entry (corresponding to a consumed food) within the time window (step 832), retrieves the consumed food vector corresponding to the identified user log entry (step 834), and adds the consumed food vector to the window consumption vector (step 836). If there are remaining user log entries within the time window (step 838), steps 832, 834, and 836 are repeated by incrementing E by 1 (step 840). When there are no remaining user log entries within the time window, the processor 105 determines whether there are any other time windows (decision block 842). If so, the method increments the time window (step 844) and returns to step 830 to add consumed food vectors corresponding to all user log entries in remaining time windows to the window consumption vector.

When there are no remaining time windows to consider, the processor 105 proceeds to concatenate all window consumption vectors into a single total consumption vector (step 846), stores the resulting total consumption vector (step 848), and retrieves the user weight matrix (step 850) and the user target vector (step 852). The processor 105 then computes the matrix product between the weight matrix and the difference between the user target vector and the total consumption vector (step 854). The index is the sum of all elements in the resulting product (step 856), and the index is returned (step 860).

Figure 10:
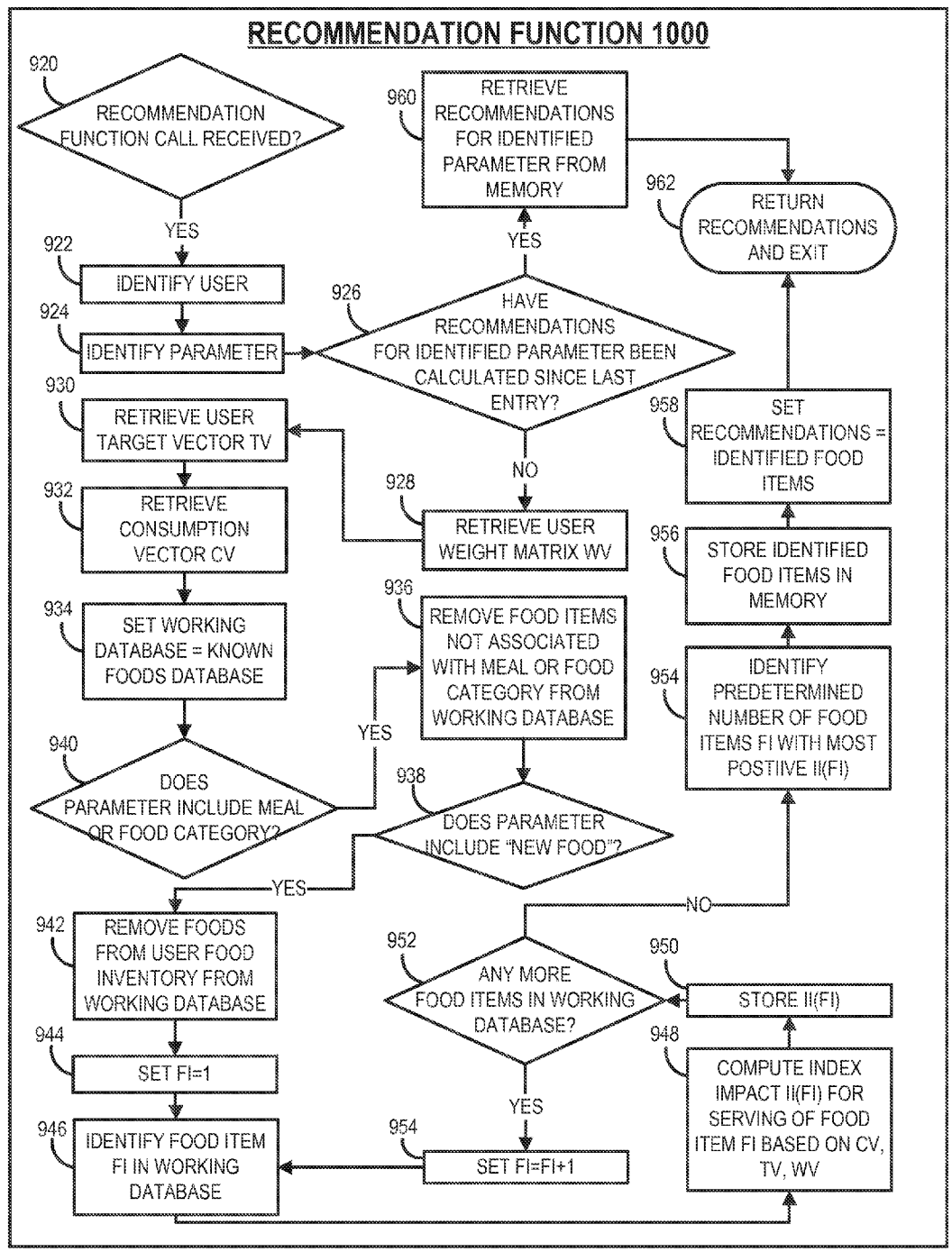
FIG. 10 is a flowchart of a method used by a computerized system to determine one or more food items suitable for recommendation to be consumed by a person, according to an illustrative implementation.

FIG. 10 is a flowchart of a method 1000 used by the processor 105 to determine a food appropriate for recommendation, according to an illustrative implementation. The method 1000 begins with receiving a call to the recommendation function (step 920) and identifying the user (step 922) and a parameter (step 924). For example, the parameter may be a specific meal type or a specific category of foods for which the user wishes to view recommendations.

The processor 105 determines whether recommendations for the parameter have been previously calculated since the last user log entry (step 926), and if so, the recommendations for the parameter are retrieved from memory (step 960) and are returned before exiting (step 962). If not, the processor 105 retrieves the user weight matrix (step 928), the user's target vector (step 930), and the user's total consumption vector (932).

A set of foods considered for the recommendation is selected based on the parameter to the recommendation function (steps 936 and 938). For example, if the parameter refers to a specific meal type or food category, the set of foods considered may include only foods associated with the meal type or the food category. Similarly, if the parameter indicates that the user wishes to view recommendations for new foods, or foods not already included in the user's logged entries (step 940), the foods in the user food inventory are removed from the set of foods under consideration (step 942). The parameter may be indicative of other considerations. For example, it may be desired to consider only foods that are available to the user. In particular, it may be undesirable to recommend an expensive food for a user with limited economic means that would preclude the user from obtaining the food. The parameter can also restrict the set of foods to those that are grown or harvested at a location near the user, or foods that are on sale at a supermarket near the user. In this case, certain foods are favored over others, and the order of food items to be considered may be sorted to consider favored foods earlier in the optimization than non-favored foods. After the set of foods to be considered is determined, an index impact is calculated for each food item in the set, based on the total consumption vector (corresponding to the consumption profile), the target vector (corresponding to the user's identified dietary programs or health-related goals), and the weight vector (step 948). The index impact is stored (step 950).

When an index impact for each food item in the set of foods has been calculated, a predetermined number of food items with the most positive index impacts are identified (step 954) and stored in memory (step 956). The identified food items are set as recommendations (step 958) and are returned (step 962). Alternatively, the method may return the first set of a predetermined number of food items with index impacts that exceed a threshold.

Figure 11:
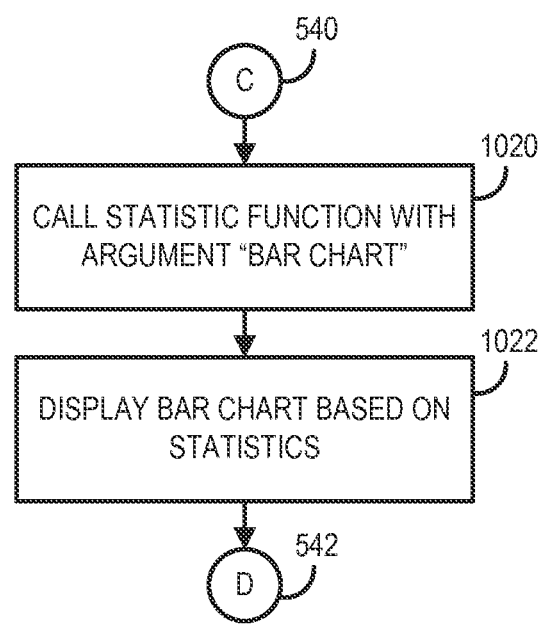
FIG. 11 is a flowchart of a method used by a computerized system to display options for educating a user regarding an alignment between the user's consumed foods and the user's nutritional goals, according to an illustrative implementation.

FIG. 11 is a flowchart of a method 1100 used by the processor 105 to display "learn" objects on the display of the user interface 112, according to an illustrative implementation. The "learn" option provides a detailed view of the user's target profile, including whether there is a deficit or excess for each nutrient in the target profile, with respect to the target level. The method begins with calling a statistic function (step 1020). Then the processor 105 displays a bar chart based on the statistics (step 1022) and returns to the home screen to display the log, live, and learn options (step 542).

Figure 12:
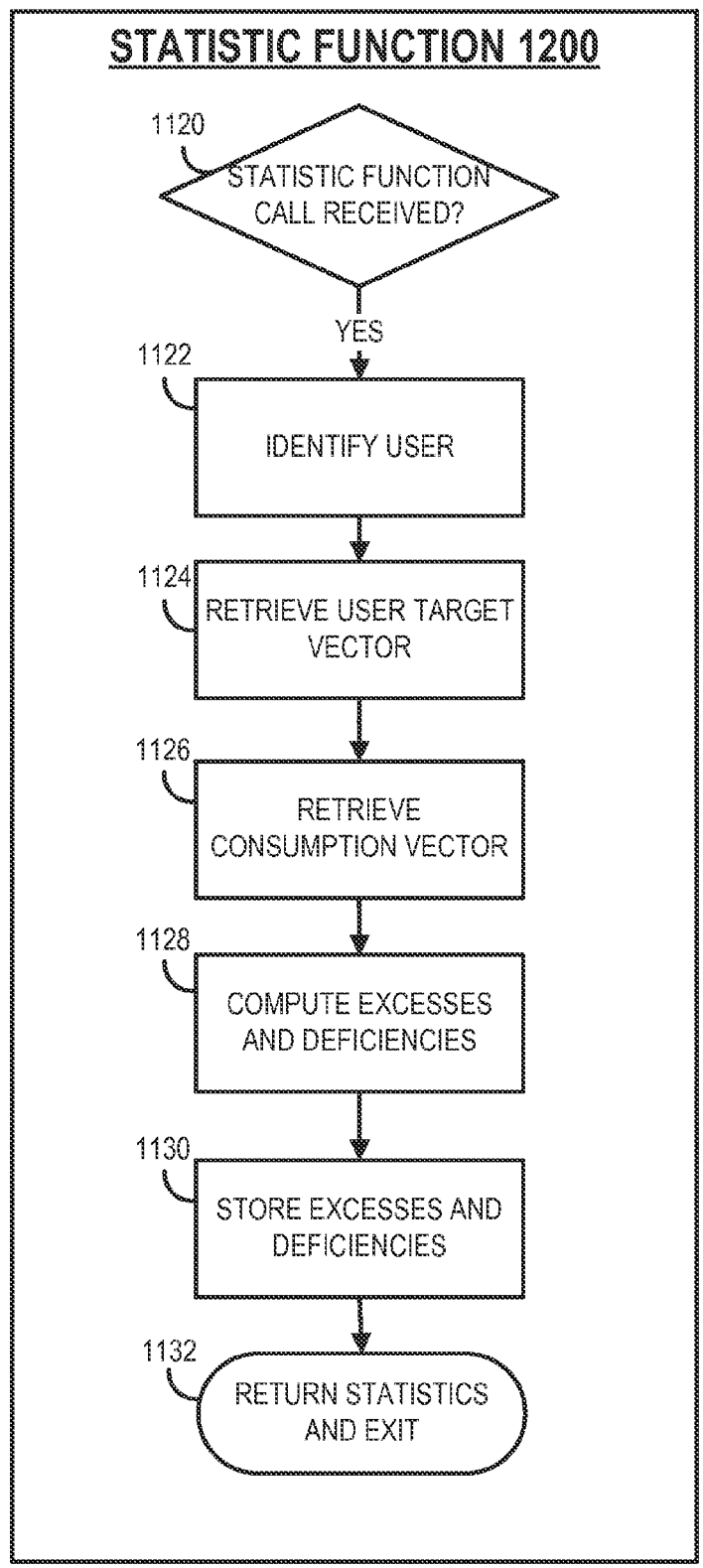
FIG. 12 is a flowchart of a method used by a computerized system to determine an alignment between a user's consumed foods and the user's nutritional goals, according to an illustrative implementation.

FIG. 12 is a flowchart of a method 1200 used by the processor 105 to determine the statistics for a user, according to an illustrative implementation. The method 1200 begins with receiving a call to the statistic function (step 1120) and identifying the user (step 1122). The processor 105 then retrieves a target vector corresponding to a target nutrient profile for the user (step 1124) and the user's consumption vector corresponding to a consumed nutrient profile for the user (step 1126). For each nutrient in the profiles, the processor 105 computes and stores either an excess or a deficiency depending on whether an element in the consumption vector exceeds a corresponding element in the target vector (steps 1128 and 1130). For example, if the consumption element exceeds the target element, the processor 105 labels the nutrient as "excess," and may further compute a percentage difference by normalizing the difference between the elements by the target element. Similarly, if the target element exceeds the consumption element, the corresponding nutrient is labeled as "deficient," and the corresponding percentage difference may be computed. In some implementations, further processing may be performed. For example, there may be an acceptable range of percentage differences (or differences or any other metric suitable for representing a difference between two values). In particular, it may be undesirable to label nutrients with small percentage differences as either "excess" or "deficient." In this case, some thresholding or other processing may be performed on the percentage differences to remove "excess" or "deficient" labels from nutrients which are within the acceptable range. In addition, different nutrients may have different acceptable ranges. These labels and optionally the percentage differences are returned as the statistics (step 1132).

In some implementations, a "bar chart" that includes a bar for each nutrient in the target profile is displayed on the user interface 112. The length of the bar for each nutrient may extend in a first direction (e.g., to the right) if the nutrient is in excess, and in another direction (e.g., to the left) if the nutrient is in deficit. In some cases, different colors may be used to indicate deficits and excesses, e.g., with bars for nutrients with deficits being displayed in one color and those of nutrients with excess being displayed in another color. A combination of these approaches may also be used.

Figure 12A:
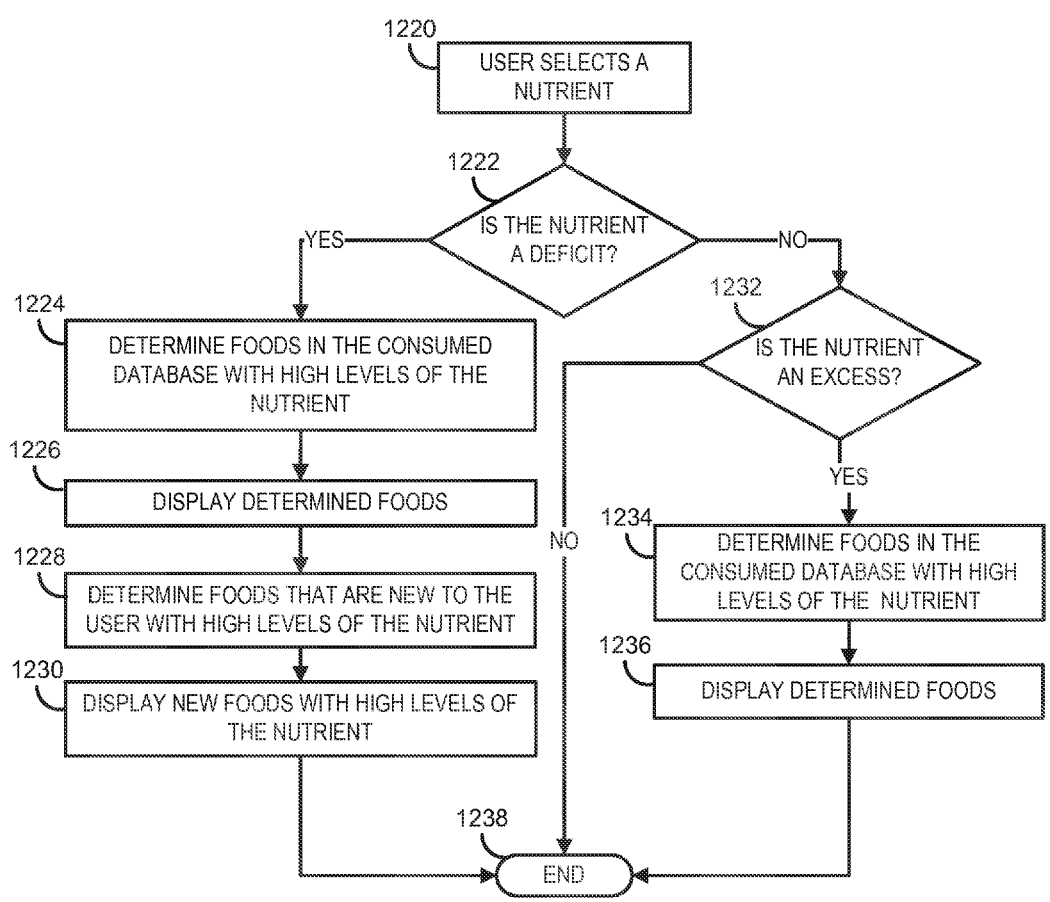
FIG. 12A is a flowchart of a method used by a computerized system to display options for educating a user regarding foods to resolve deviations between the user's consumed foods and the user's nutritional goals, according to an illustrative implementation.

FIG. 12A is a flowchart of a method 1210 used by the processor 105 to display nutrient details for a user, according to an illustrative implementation. The method 1210 begins with the user selecting a nutrient (step 1220) and determining whether the current user consumption level for the nutrient is below the target range for the nutrient (step 1222). If so, the processor 105 determines which foods in the consumed foods database for the user have high levels of the nutrient (step 1224) and displays these foods (1226). The processor 105 also determines foods that have not been consumed and logged by the user with high levels of the nutrient (step 1228) and displays these foods (step 1230). Alternatively, if the current user consumption level for the nutrient is above the target range for the nutrient (step 1232), the processor 105 determines foods in the consumed database with high levels of the nutrient (step 1234) and displays the determined foods (step 1236). Example displays of the user interface are shown in FIGS. 36B-D.

In particular, for a deficient nutrient, when the processor 105 determines which foods in a database have high levels of the selected nutrient (such as in steps 1224 and 1228), the processor 105 may additionally calculate the index impact, corresponding to the change in index if the user were to consume the food. The processor 105 only displays the foods (such as in steps 1226, 1230) that have a positive index impact, meaning only foods that would cause the user's index to increase are displayed. Furthermore, the foods may be listed in order of their levels of the selected nutrient or in order of their index impacts. In this way, the foods that are displayed to the user are those that would help the user to reach the user's goals.

In addition, for an excessive nutrient, it may be desirable to suggest foods to the user to avoid, such that the user may be discouraged from consuming previously consumed foods that contribute to the excess level of the nutrient. As in the case for a deficient nutrient, the processor 105 may calculate an index impact for each food in the consumed database, but this time, select those foods with the most negative index impacts to display. The processor 105 may display (in step 1236) the foods in order of their levels of the selected nutrients or in order of their index impacts such that the user. Displaying data in this way allows the user to view what foods the user currently consumes that may negatively affect the user's index.

Figure 13:
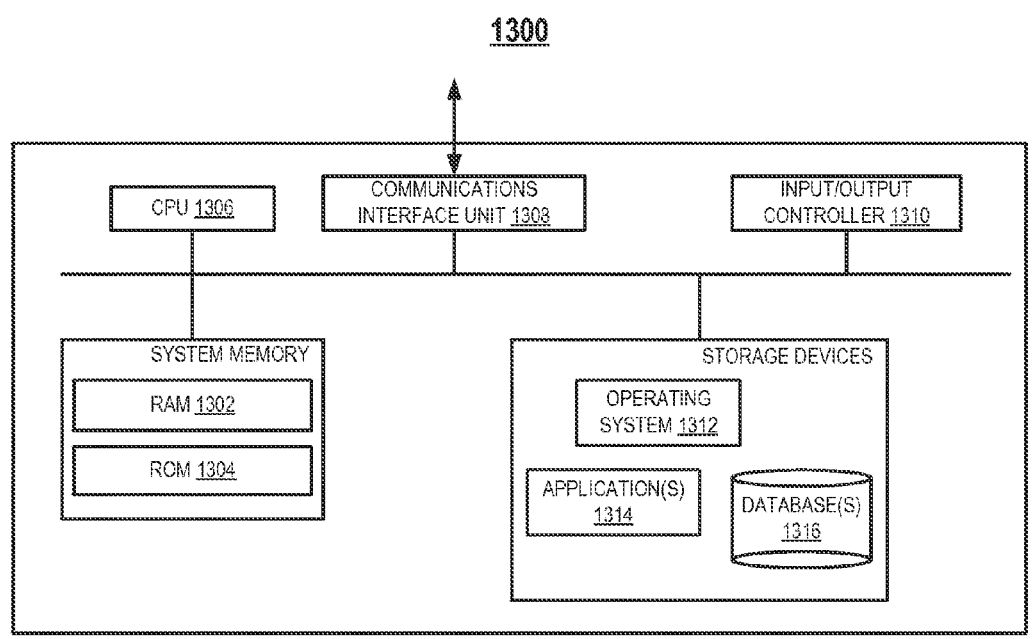
FIG. 13 is a block diagram of a computing device for performing any of the processes described herein, according to an illustrative implementation.

FIG. 13 is a block diagram of a computing device, such as any of the components of the systems of FIGS. 1A-1C, for performing any of the processes described herein. Each of the components of these systems may be implemented on one or more computing devices 1300. In certain aspects, a plurality of the components of these systems may be included within one computing device 1300. In certain implementations, a component and a storage device may be implemented across several computing devices 1300.

The computing device 1300 includes at least one communications interface unit, an input/output controller 1310, system memory, and one or more data storage devices. The system memory includes at least one random access memory (RAM 1302) and at least one read-only memory (ROM 1304). All of these elements are in communication with a central processing unit (CPU 1306) to facilitate the operation of the computing device 1300. The computing device 1300 may be configured in many different ways. For example, the computing device 1300 may be a conventional standalone computer or alternatively, the functions of computing device 1300 may be distributed across multiple computer systems and architectures. In FIG. 13, the computing device 1300 is linked, via network or local network, to other servers or systems.

The computing device 1300 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 1308 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 1306 includes a processor, such as one or more conventional microprocessors and one or more supplementary co-processors such as math co-processors for offloading workload from the CPU 1306. The CPU 1306 is in communication with the communications interface unit 1308 and the input/output controller 1310, through which the CPU 1306 communicates with other devices such as other servers, user terminals, or devices. The communications interface unit 1308 and the input/output controller 1310 may include multiple communication channels for simultaneous communication with, for example, other processors, servers or client terminals.

The CPU 1306 is also in communication with the data storage device. The data storage device may include an appropriate combination of magnetic, optical or semiconductor memory, and may include, for example, RAM 1302, ROM 1304, flash drive, an optical disc such as a compact disc or a hard disk or drive. The CPU 1306 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 1306 may be connected to the data storage device via the communications interface unit 1308. The CPU 1306 may be configured to perform one or more particular processing functions.

The data storage device may store, for example, (i) an operating system 1312 for the computing device 1300; (ii) one or more applications 1314 (e.g., computer program code or a computer program product) adapted to direct the CPU 1306 in accordance with the systems and methods described here, and particularly in accordance with the processes described in detail with regard to the CPU 1306; or (iii) database(s) 1316 adapted to store information that may be utilized to store information required by the program.

The operating system 1312 and applications 1314 may be stored, for example, in a compressed, an uncompiled and an encrypted format, and may include computer program code. The instructions of the program may be read into a main memory of the processor from a computer-readable medium other than the data storage device, such as from the ROM 1304 or from the RAM 1302. While execution of sequences of instructions in the program causes the CPU 1306 to perform the process steps described herein, hard-wired circuitry may be used in place of, or in combination with, software instructions for implementation of the processes of the present invention. Thus, the systems and methods described are not limited to any specific combination of hardware and software.

Suitable computer program code may be provided for performing one or more functions in relation to aligning dietary behavior as described herein. The program also may include program elements such as an operating system 1312, a database management system and "device drivers" that allow the processor to interface with computer peripheral devices (e.g., a video display, a keyboard, a computer mouse, etc.) via the input/output controller 1310.

The term "computer-readable medium" as used herein refers to any non-transitory medium that provides or participates in providing instructions to the processor of the computing device 1300 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EE-PROM, any other memory chip or cartridge, or any other non-transitory medium from which a computer can read.

Various forms of computer readable media may be involved in carrying one or more sequences of one or more instructions to the CPU 1306 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 1300 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

FIGS. 14-37 are various example displays of the user interface 112 on a computer screen, according to illustrative implementations.

FIG. 14 is a home screen that a user views upon providing the user's username and password. At the top right of the screen is the user's index (a score from 0 to 100 in this implementation), and the log, live, and learn options are displayed.

FIG. 15 is a personal information screen that the user uses to select from a list of dietary programs or goals. In addition, the user may add additional goals or comments in a free-form answer field, and may provide any demographic features towards the bottom of the screen. The information that the user selects or adds to this screen may be stored in the dietary programs database 106C in FIG. 1B or in any other database.

FIG. 16 is a screen that displays the user's target profile, based on the user inputs provided on the screen in FIG. 15. The calculation of a user's target profile is described in more detail in relation to FIG. 4.

FIG. 17 is a screen that displays a list of consumed and logged foods specific to the user. Data corresponding to the user-specific foods may be stored in the consumed foods database 106B in FIG. 1B or in any other database.

Figure 20:
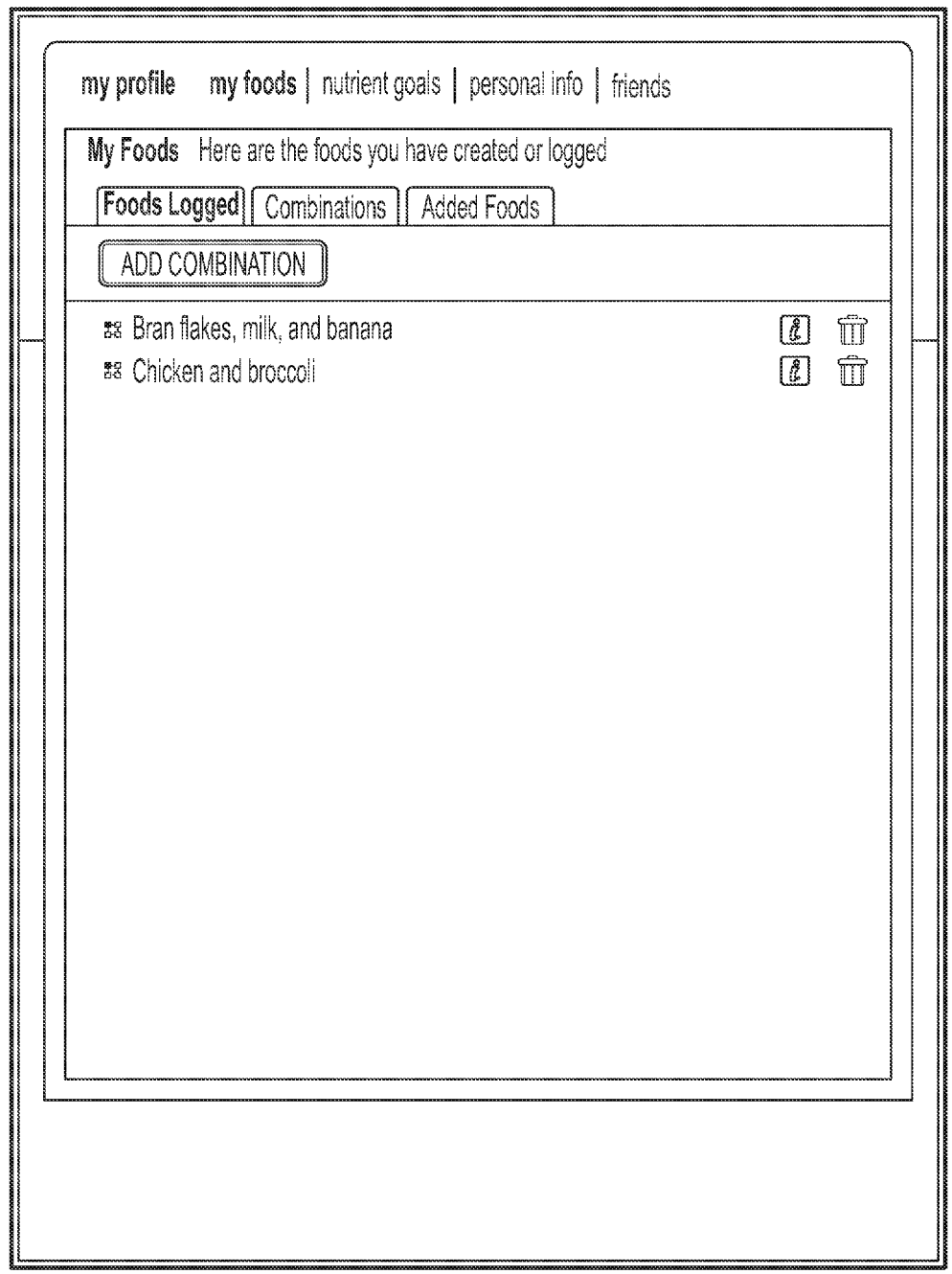

FIGS. 18-20 are screens that display how the user may create combinations of multiple foods. For example, if a user often eats chicken and broccoli together, the user may create a combination including chicken and broccoli. By adding the combination to the user-specific consumed foods database, the user can select the combination when logging the foods in the future, rather than having to add each food item individually.

Figure 21:
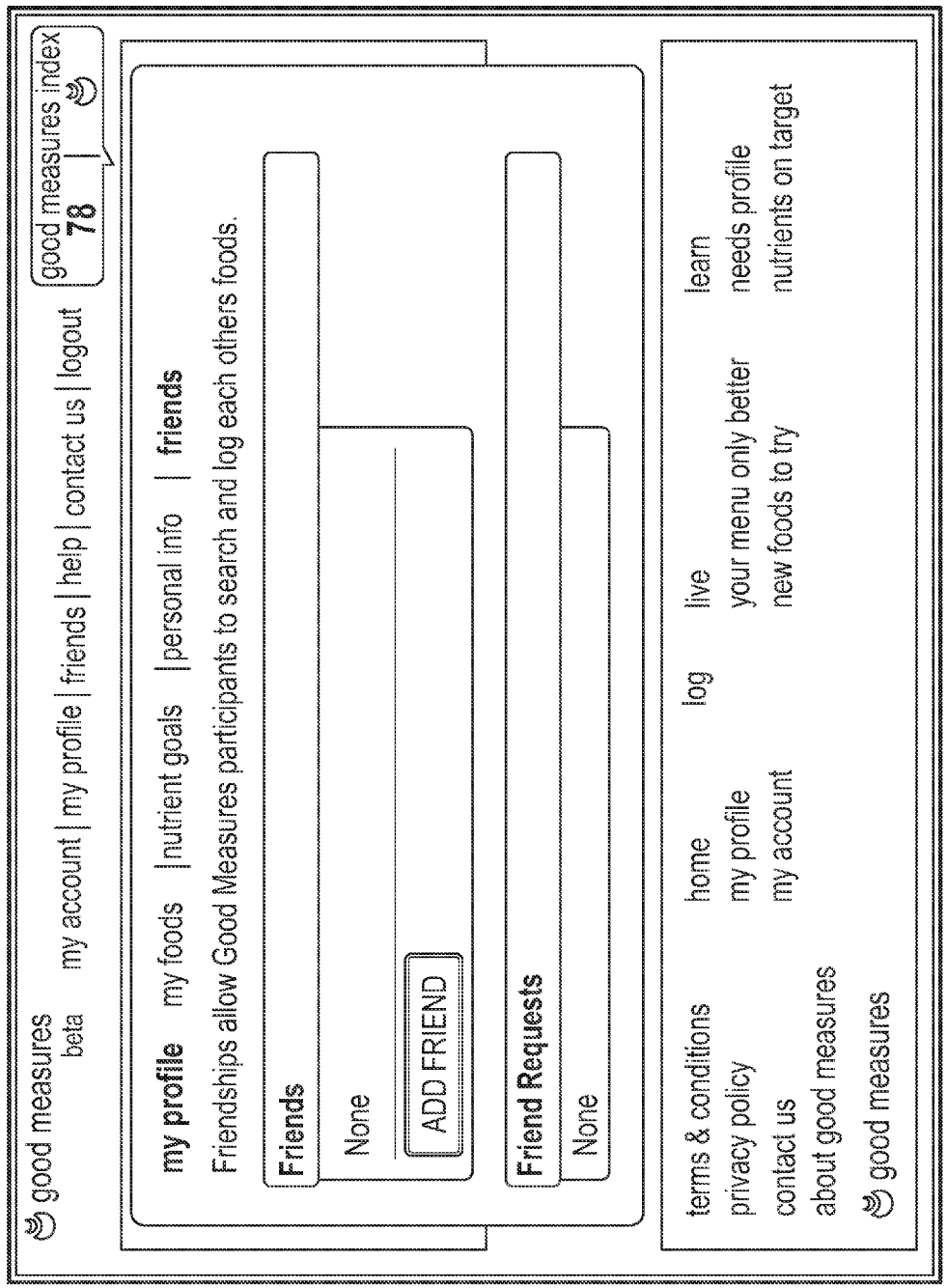
FIGS. 21-22 are example screens that display how the user may transmit a friend request, according to an illustrative implementation.
Figure 22:
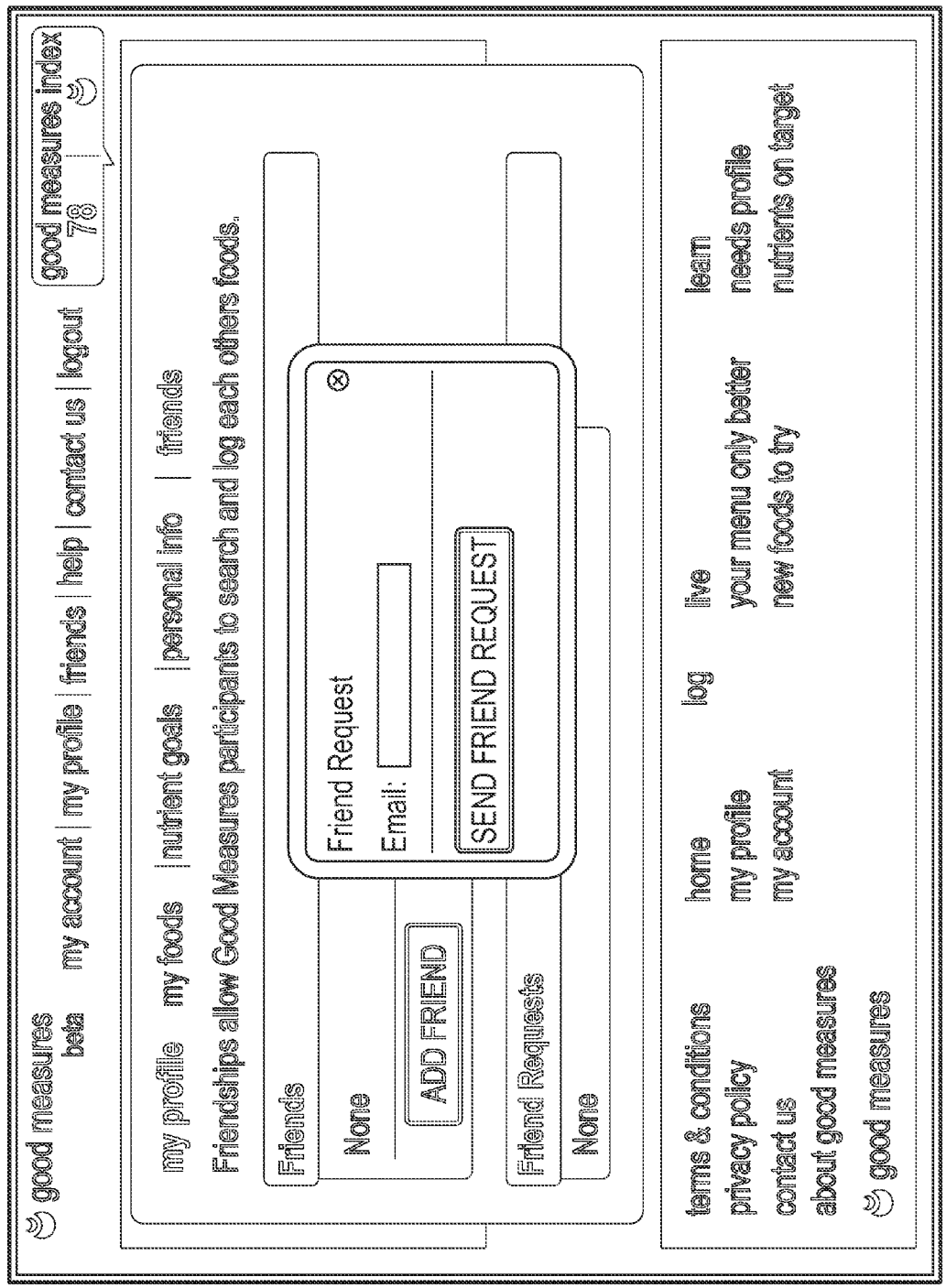

FIGS. 21-22 are screens that display how the user may transmit a friend request. The user may know another user and may wish to track the other user's progress. For example, a contest may be formed among a group of users, such that each user in the group may view the index of another user in the group. The user with the highest index at the end of some time period, or the user with the biggest improvement in index over some time period may receive some prize. In addition, the user may wish to view or log foods previously logged by the other user.

FIGS. 23-26 are screens that display how a user may create a log entry to indicate that a hot chicken sandwich was consumed for lunch. Details of how the data resulting from this log entry are described in relation to FIGS. 3, 4, and 5A-5C.

Figure 28:
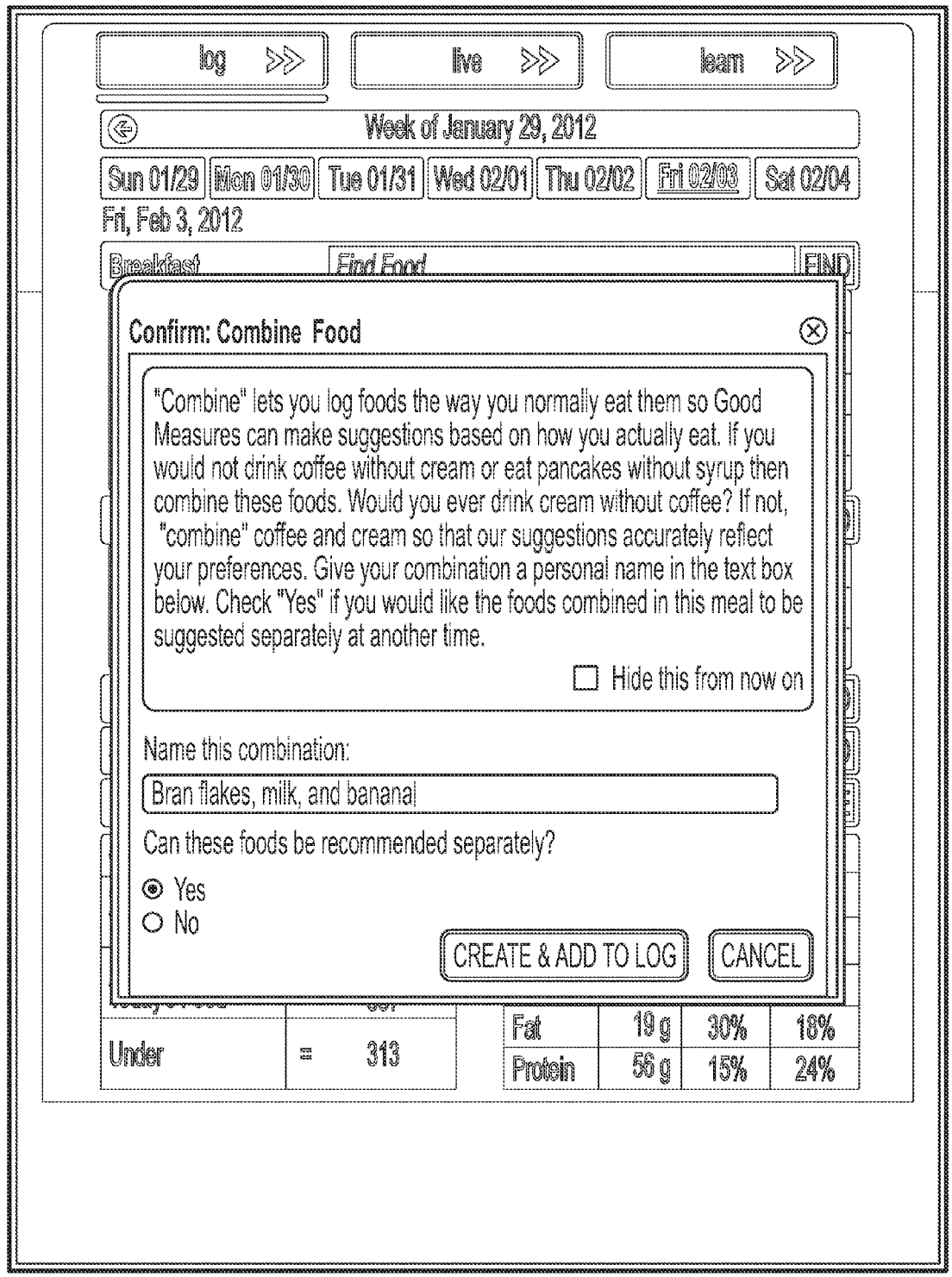

FIGS. 27-29 are screens that display how a user may create a combination of foods already logged. The combination is added to the user's consumed foods database.

Figure 30:
FIG. 30 is an example screen that displays how a user may add a new food to the database, according to an illustrative implementation.

FIG. 30 is a screen that displays how a user may add a new food to the database. For example, the user may wish to log a particular food that is not in the database. In this case, the user may provide the food name and nutritional information, and the food is added to the database.

FIGS. 31-33 are screens that display how a user may log exercise. For example, the user may input freestyle swimming for 60 minutes, and a processor calculates a number of calories corresponding to the exercise for the user. The user may also directly provide a number of calories corresponding to an exercise. The net number of calories (calories consumed by the user minus the calories burnt through exercise) may be an element in the nutrient vectors described above.

FIG. 34 is a screen that displays a new food suggestion for the user, corresponding to a food that is not in the consumed foods database for the user. The recommendation screen also displays nutritional information corresponding to the new food suggestion. Details of how the recommendation is determined are described in relation to FIG. 5C.

FIG. 35 is a screen that displays meal suggestions for the user, corresponding to meals in the consumed foods database for the user. The displayed dinner suggestions correspond to the meals that resulted in the highest index impact scores (shown on the right of the display). Details of how the meal recommendations are determined are described in relation to FIG. 5B.

Figure 36A:
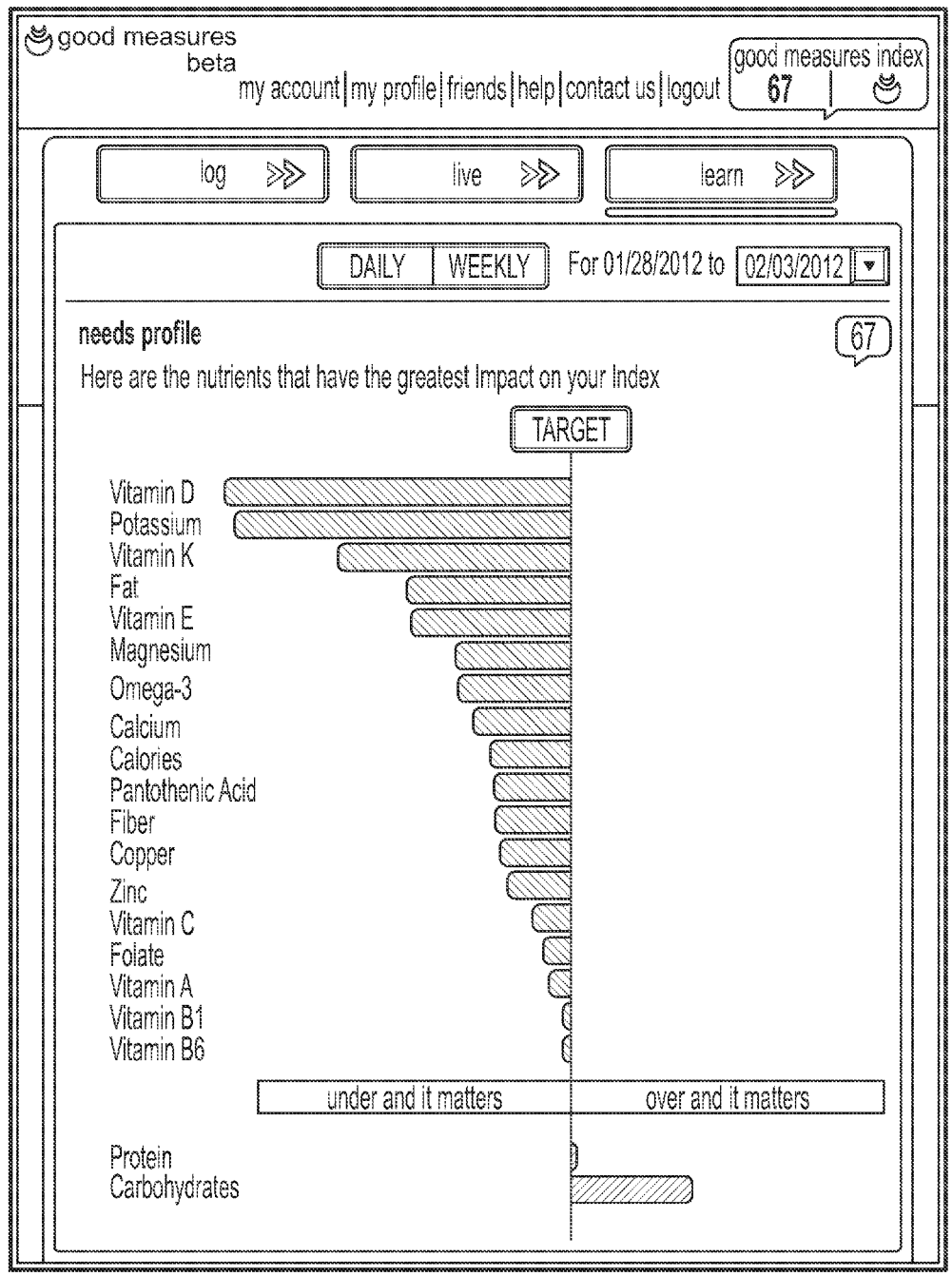
FIG. 36A is an example screen that displays a bar chart corresponding to a set of nutrients for which the user consumption levels are below or above levels corresponding to the target profile, according to an illustrative implementation.
Figure 36B:
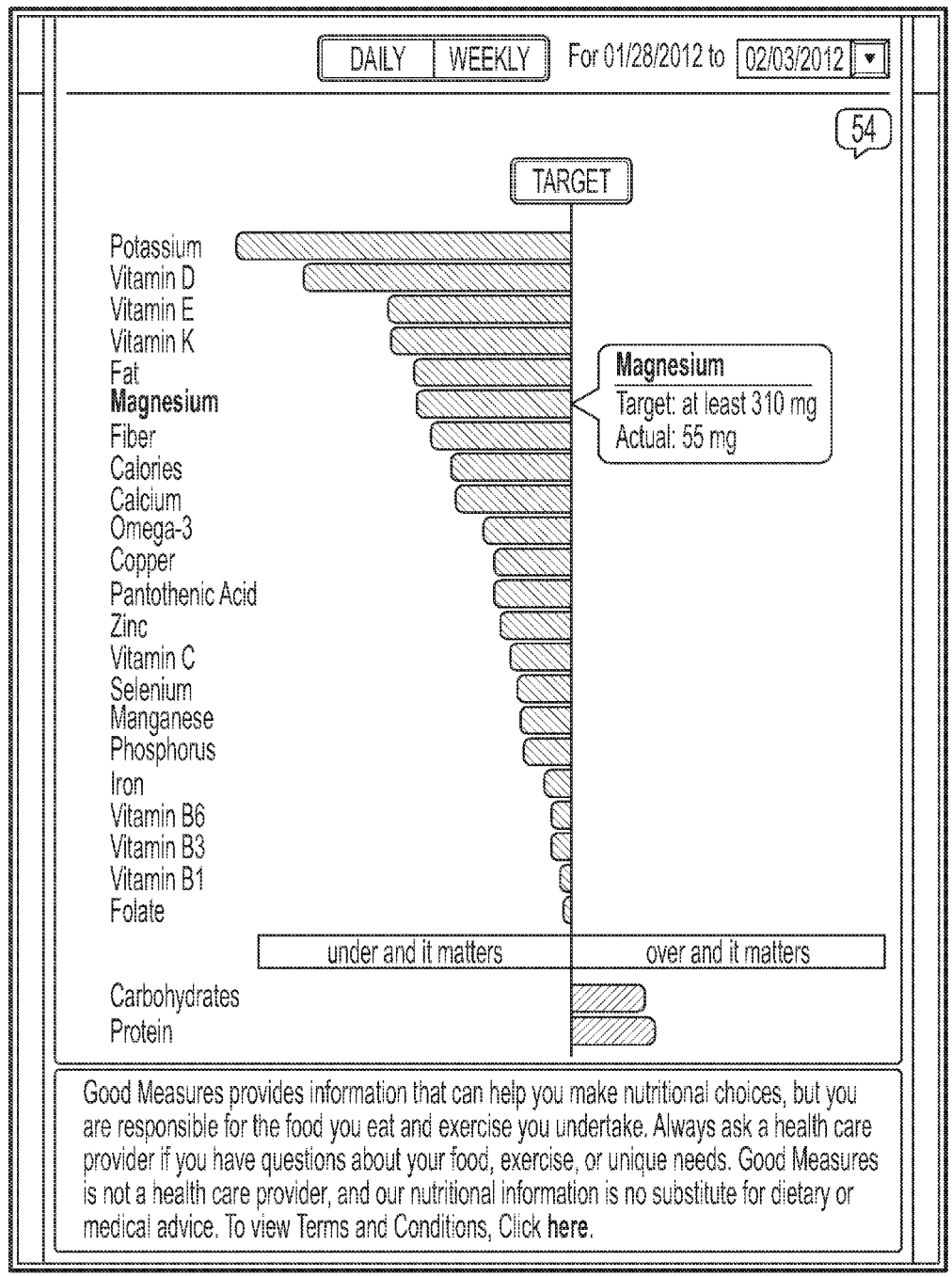
FIG. 36B is an example screen that displays details of a bar chart including a target level and a consumed level of a nutrient for a user, according to an illustrative implementation.
Figure 36D:
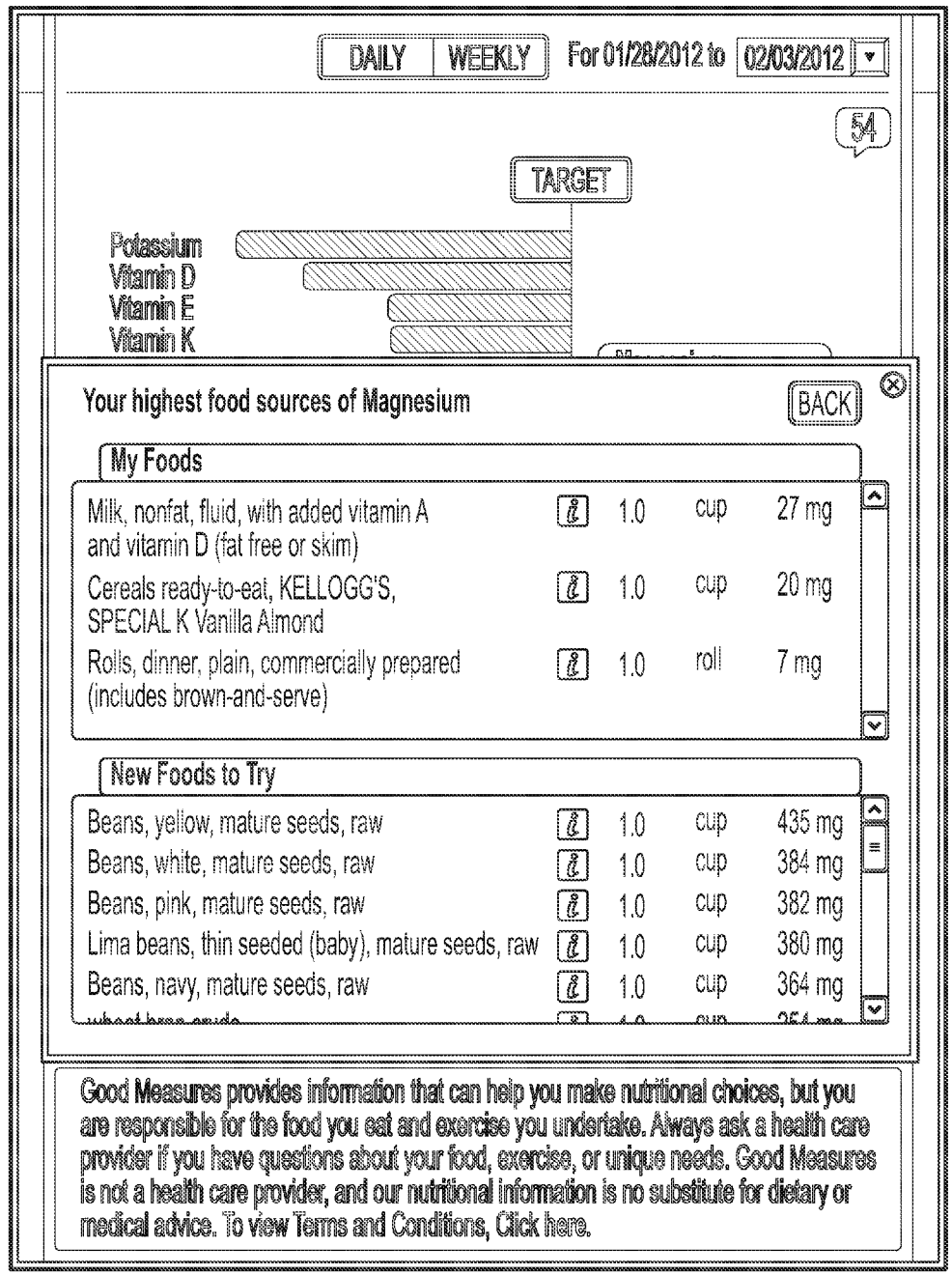
FIG. 36D is an example screen that displayed new food recommendations with high amounts of a selected nutrient, according to an illustrative implementation.

FIG. 36A is a screen that displays a bar chart corresponding to a set of nutrients for which the user consumption levels are below or above levels corresponding to the target profile. Details of how these statistics are generated are described in relation to FIGS. 11 and 12. FIG. 36B is a screen that displays the same information as in FIG. 36A, but further showing that when the user hovers a control device (such as a mouse) over the bar on the chart corresponding to a nutrient (magnesium), details are displayed. These details include the target and actual levels for the user. The user may select the bar, resulting in a display that shows the user which foods the user has consumed that contribute to the nutrient level. FIG. 36C shows an example of this display and shows a list of foods consumed by the user that include the nutrient (magnesium), sorted by the amount of the nutrient contained in the consumed food. If the user then selects the "try this" button on the top right of the screen in FIG. 36C, and the screen of FIG. 36D is displayed. FIG. 36D shows an example screen of new food recommendations with high amounts of the selected nutrient. Importantly, the new food recommendations include only those that would be beneficial to the user's index.

FIG. 37 is a screen that displays a list of nutrients for which the user consumption levels are within a range close to the target profile. Details of how these statistics are generated are described in relation to FIG. 12.

FIGS. 38-46 are various example displays of the user interface 112 on a mobile device, according to illustrative implementations.

Figure 38:
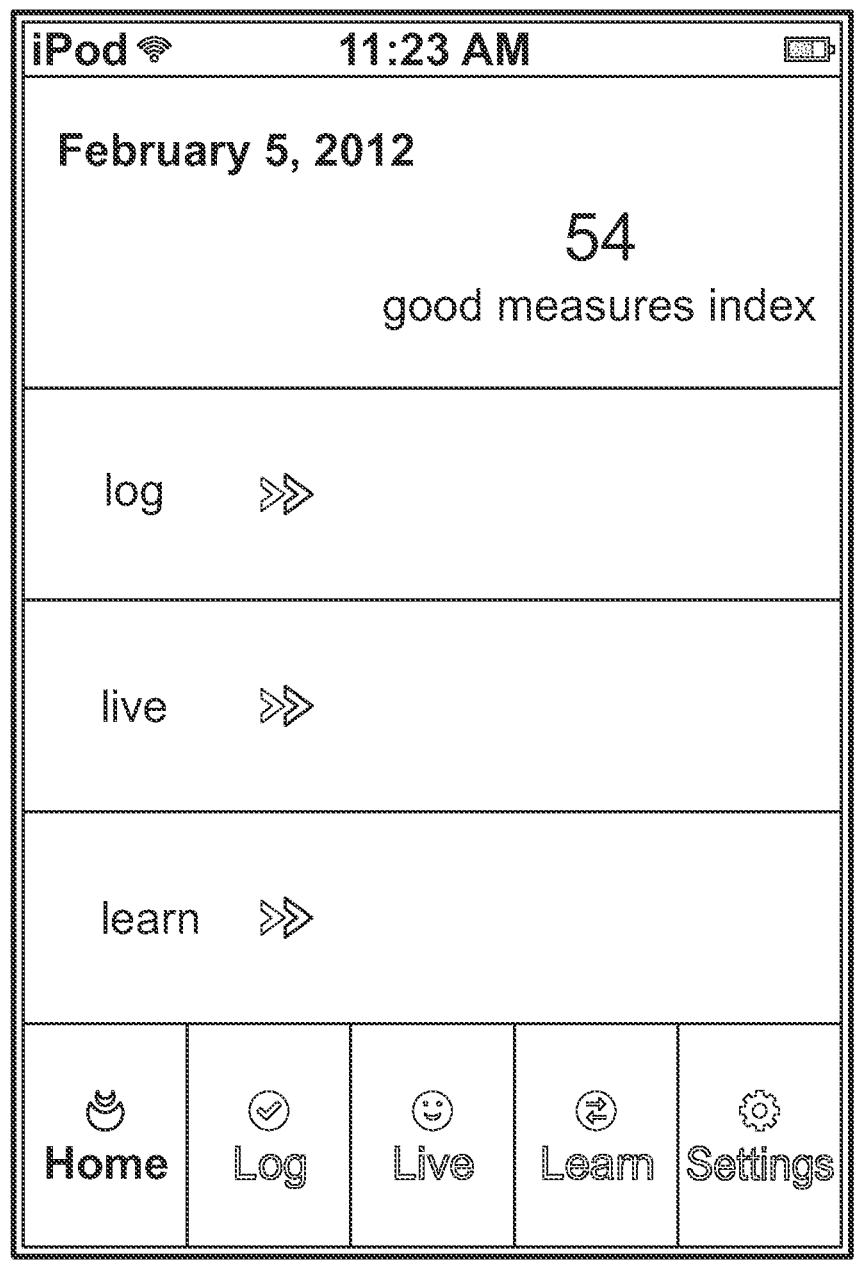
FIG. 38 is a home screen on a mobile device that is displayed to a user upon opening an application, according to an illustrative implementation.
Figure 39:
FIGS. 39-42 are example screens that display suggested new foods for the user, according to an illustrative implementation.

FIG. 38 is a home screen that a user views upon opening the application on a mobile device. At the top right of the screen is the user's index (a score out of 100), and the log, live, and learn options are displayed.

FIGS. 39-42 are screens that display suggested new foods for the user. The user may select a particular food category to view recommendations, or the user may select the "surprise me" option, which returns a number of recommendations in different categories.

FIGS. 43-46 are screens that display the needs profile and on target list for the user. The needs profile may be viewed as a bar chart or as a table. The user may also select the time period over which to consider the logged consumed foods.

It is to be understood that while various illustrative implementations have been described, the forgoing description is merely illustrative and does not limit the scope of the invention. While several examples have been provided in the present disclosure, it should be understood that the disclosed systems, components and methods of manufacture may be embodied in many other specific forms without departing from the scope of the present disclosure.

The examples disclosed can be implemented in combinations or sub-combinations with one or more other features described herein. A variety of apparatus, systems and methods may be implemented based on the disclosure and still fall within the scope of the invention. Also, the various features described or illustrated above may be combined or integrated in other systems or certain features may be omitted, or not implemented.

While various embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

All references cited herein are incorporated by reference in their entirety and made part of this application.

The invention claimed is:

1. A system for aligning a person's diet with specific dietary goals, the system comprising:
   an input port configured to receive (1) data representative of a dietary program comprising a user-designed or a user-selected dietary program for the person and (2) data representative of one or more foods consumed by the person, wherein the dietary program includes a nutrition-related goal for the person;
   at least one computer processor, in communication with the input port and an electronic database configured to store nutritional information related to a plurality of foods, the at least one computer processor configured to:
      generate, based on the dietary program, a target nutritional profile including a target level for each of a plurality of target nutrients associated with the dietary program, wherein the target nutrients include a plurality of micronutrients and a plurality of macronutrients;
      generate, based on the nutritional information in the electronic database, a consumed amount for each of a plurality of consumed nutrients associated with the one or more foods previously consumed by the person;
      compute a deviation for each of the target nutrients by comparing the target level of the target nutrient to the consumed amount of the respective target nutrient to obtain a plurality of deviations, wherein each deviation indicates a deficit for the respective target nutrient if the consumed amount of the target nutrient is below the target level of the target nutrient, and an excess for the respective target nutrient if the consumed amount of the target nutrient is above the target level of the target nutrient;
      determine a nutrient coefficient for each target nutrient based on the nutrition-related goal associated with the person, wherein the nutrient coefficient for each target nutrient is indicative of an importance of the respective target nutrient to the person relative to other target nutrients;

compute a nutritional index that represents an aggregate alignment between the consumed amounts of the plurality of consumed nutrients and the target nutritional profile, wherein the nutritional index is based on a weighted function that applies the nutrient coefficient for each target nutrient to the respective deviation for the target nutrient;

generate a plurality of food recommendations and a predicted index impact for each of the food recommendations, each food recommendation comprising a recommended food and a specified portion size of the recommended food that if consumed by the person improves an alignment of at least one of the target nutrients and simultaneously reduces a negative impact on an alignment of at least another one of the target nutrients, wherein the predicted index impact for each recommended food is indicative of a predicted change in the nutritional index if the person consumes the recommended food; and an output port configured to provide the nutritional index, the predicted index impact for each food recommendation, and the plurality of food recommendations for display by a user interface device, wherein the user interface device is configured to display the plurality of food recommendations in an order determined based at least in part on the predicted index impact associated with each food recommendation.

2. The system of claim 1, wherein the nutrition-related goal is selected from the group consisting of a diet goal, a weight goal, an exercise goal, and a medical condition.

3. The system of claim 1, wherein the data representative of the one or more foods previously consumed by the person comprise data representative of a plurality of consumed meals previously consumed by the person, each consumed meal comprising a specified portion for each of a plurality of foods in the consumed meal, and wherein the at least one computer processor is configured to generate the food recommendations by:

generating data indicative of a modified meal for each of the plurality of consumed meals, wherein each modified meal comprises a modified portion for at least one of the plurality of foods contained in the respective consumed meal;

computing a candidate index impact for each of the modified meals, the candidate index impact being indicative of a quantified change in the nutritional index if the modified meal is consumed by the person; and selecting as the food recommendations a subset of the modified meals based on the associated candidate index impact.

4. The system of claim 1, wherein the output port is further configured to provide data representative of the deviation for each of a subset of the plurality of target nutrients for display by the user interface device, and wherein the at least one computer processor is configured to receive from the user interface device a selected target nutrient from the subset of target nutrients, and in response to the receiving the selected target nutrient:

provide to the output port data indicative of a plurality of new foods not previously consumed by the person if the deviation for the selected target nutrient indicates a deficit; and provide to the output port data indicative of a plurality of previously consumed foods if the deviation for the selected target nutrient indicates an excess.

5. The system of claim 1, wherein the nutritional index is representative of the alignment between the person's diet and the dietary program over a predefined time period between 3 days to 10 days.

6. The system of claim 1, wherein the at least one computer processor, the input port, and the output port are housed in the user interface device.

7. The system of claim 6, wherein the user interface device comprises a GPS-enabled mobile device, and wherein the at least one computer processor is configured to determine that one or more locations detected using the GPS device correspond to a restaurant and to provide a prompt to the user interface device to identify foods consumed at the restaurant.

8. The system of claim 1, wherein the food recommendations comprise a plurality of recommended meals in a recommended meal plan for a plurality of days, wherein each recommended meal is associated with a recommended calendar date.

9. The system of claim 3, wherein the at least one computer processor is configured to select the subset of modified meals by selecting the modified meals having a candidate index impact that is equal to or greater than a threshold.

10. The system of claim 3, wherein each of the candidate modified meals is associated with a meal classification selected from the group consisting of breakfast, brunch, lunch, snack, and dinner, and wherein the at least one computer processor is further configured to associate each of the food recommendations with a recommended calendar date and a recommended meal classification identical to the meal classification of the corresponding candidate modified meal.

11. The system of claim 10, wherein each meal classification is associated with a predetermined caloric allowance, and wherein the at least one computer processor is configured to modify the one or more specified portion sizes based on the caloric allowance.

12. The system of claim 1, wherein the at least one computer processor is configured to select as the recommended food a candidate food from the plurality of foods not previously consumed by the person.

13. The system of claim 1, wherein the at least one computer processor is configured to assign a nutrient coefficient to each target nutrient by assigning a first numeric coefficient to the target nutrient if the target nutrient is in deficit and assigning a second numeric coefficient to the target nutrient if the target nutrient is in excess, wherein the nutrient coefficient assigned is indicative of a relative importance of an excess compared to a deficit of the target nutrient.

14. The system of claim 1, wherein the at least one computer processor is configured to determine the nutrient coefficient for each target nutrient based on a weight function associated with the target nutrient.

15. The system of claim 1, wherein the at least one computer processor is configured to provide the nutritional index as a number, an alphabetical grade, a color selected from a color gradient indicative of a range of the nutritional index, or a graphical icon.

16. A method for aligning a person's diet with specific dietary goals, the method comprising:

receiving in a computer system in communication with an electronic database (1) data representative of a dietary program comprising a user-designed or a user-selected dietary program for the person and (2) data representative of one or more foods consumed by the person, wherein the dietary program includes a nutrition-related goal for the person and the electronic database stores nutritional information related to a plurality of foods; said computer system performs the steps of:

generating, based on the dietary program, a target nutritional profile including a target level for each of a plurality of target nutrients associated with the dietary program, wherein the target nutrients include a plurality of micronutrients and a plurality of macronutrients;

generating, based on the nutritional information in the electronic database, a consumed amount for each of a plurality of consumed nutrients associated with the one or more foods previously consumed by the person;

computing a deviation for each of the target nutrients by comparing the target level of the target nutrient to the consumed amount of the respective target nutrient to obtain a plurality of deviations, wherein each deviation indicates a deficit for the respective target nutrient if the consumed amount of the target nutrient is below the target level of the target nutrient, and an excess for the respective target nutrient if the consumed amount of the target nutrient is above the target level of the target nutrient;

determining a nutrient coefficient for each target nutrient based on the nutrition-related goal associated with the person, wherein the nutrient coefficient for each target nutrient is indicative of an importance of the respective target nutrient to the person relative to other target nutrients;

computing a nutritional index that represents an aggregate alignment between the consumed amounts of the plurality of consumed nutrients and the target nutritional profile, wherein the nutritional index is based on a weighted function that applies the nutrient coefficient for each target nutrient to the respective deviation for the target nutrient;

generating a plurality of food recommendations and a predicted index impact for each of the food recommendations, each food recommendation comprising a recommended food and a specified portion size of the recommended food that if consumed by the person improves an alignment of at least one of the target nutrients and simultaneously reduces a negative impact on an alignment of at least another one of the target nutrients, wherein the predicted index impact for each recommended food is indicative of a predicted change in the nutritional index if the person consumes the recommended food; and providing, for display by a user interface device, the nutritional index, the predicted index impact for each food recommendation, and the plurality of food recommendations, wherein the user interface device is configured to display the plurality of food recommendations in an order determined based at least in part on the predicted index impact associated with each food recommendation.

17. The method of claim 16, wherein the nutrition-related goal is selected from the group consisting of a diet goal, a weight goal, an exercise goal, and a medical condition.

18. The method of claim 16, wherein the data representative of the one or more foods previously consumed by the person comprise data representative of a plurality of consumed meals previously consumed by the person, each consumed meal comprising a specified portion for each of a plurality of foods in the consumed meal, and generating the food recommendations comprises:
generating data indicative of a modified meal for each of the plurality of consumed meals, wherein each modified meal comprises a modified portion for at least one of the plurality of foods contained in the respective consumed meal;

computing a candidate index impact for each of the modified meals, the candidate index impact being indicative of a quantified change in the nutritional index if the modified meal is consumed by the person; and selecting as the food recommendations a subset of the modified meals based on the associated candidate index impact.

19. The method of claim 16, further comprising
providing data representative of the deviation for each of a subset of the plurality of target nutrients for display by the user interface device; and in response to receiving a selected target nutrient from the subset of target nutrients:
providing, for display by the user interface device, data indicative of a plurality of new foods not previously consumed by the person if the deviation for the selected target nutrient indicates a deficit; and providing, for display by the user interface device, data indicative of a plurality of previously consumed foods if the deviation for the selected target nutrient indicates an excess.

20. The method of claim 16, wherein the nutritional index is representative of the alignment between the person's diet and the dietary program over a predefined time period between 3 days to 10 days.

21. The method of claim 16, wherein the user interface device comprises a mobile user device, and wherein the receiving and the computing are performed by the mobile user device.

22. The method of claim 21, wherein the user interface device comprises a GPS-enabled mobile device, the method further comprising:
determining that one or more locations detected using the GPS device correspond to a restaurant; and
providing a prompt to the user interface device to identify foods consumed at the restaurant.

23. The method of claim 16, wherein the food recommendations comprise a plurality of recommended meals in a recommended meal plan for a plurality of days, wherein each recommended meal is associated with a recommended calendar date.

24. The method of claim 18, further comprising selecting, by the computer system, the subset of modified meals by selecting the modified meals having a candidate index impact that is equal to or greater than a threshold.

25. The method of claim 18, wherein each of the candidate modified meals is associated with a meal classification selected from the group consisting of breakfast, brunch, lunch, snack, and dinner, the method further comprising associating each of the food recommendations with a recommended calendar date and a recommended meal classification identical to the meal classification of the corresponding candidate modified meal.

26. The method of claim 25, wherein each meal classification is associated with a predetermined caloric allowance, the method further comprising modifying the one or more specified portion sizes based on the caloric allowance.

27. The method of claim 16, further comprising selecting as the recommended food a candidate food from the plurality of foods not previously consumed by the person.

28. The method of claim 16, further comprising assigning a nutrient coefficient to each target nutrient by assigning a first numeric coefficient to the target nutrient if the target nutrient is in deficit and assigning a second numeric coefficient to the target nutrient if the target nutrient is in excess, wherein the nutrient coefficient assigned is indicative of a relative importance of an excess compared to a deficit of the target nutrient.

29. The method of claim 16, further comprising determining the nutrient coefficient for each target nutrient based on a weight function associated with the target nutrient.

30. The method of claim 16, further comprising displaying the nutritional index as a number, an alphabetical grade, a color selected from a color gradient indicative of a range of the nutritional index, or a graphical icon.

* * * * *